US012098162B2

(12) United States Patent
Lourenço et al.

(10) Patent No.: US 12,098,162 B2
(45) Date of Patent: Sep. 24, 2024

(54) NEUTRAL GLYCOSYLATED AMIDES AND DIANIONIC GLUCURONIDATED ACIDS AS STABILIZERS FOR BIOLOGICAL MOLECULES

(71) Applicant: Extremochem, LDA, Lisbon (PT)

(72) Inventors: Eva Correia Lourenço, Lisbon (PT); Osvaldo Ascenso, Juncal (PT)

(73) Assignee: EXTREMOCHEM, LDA, Lisbon (PT)

( * ) Notice: Subject to any disclaimer, the term of this patent is extended or adjusted under 35 U.S.C. 154(b) by 0 days.

(21) Appl. No.: 16/763,259

(22) PCT Filed: Nov. 13, 2018

(86) PCT No.: PCT/IB2018/001411
§ 371 (c)(1),
(2) Date: May 12, 2020

(87) PCT Pub. No.: WO2019/092504
PCT Pub. Date: May 16, 2019

(65) Prior Publication Data
US 2022/0033427 A1    Feb. 3, 2022

Related U.S. Application Data

(60) Provisional application No. 62/585,341, filed on Nov. 13, 2017.

(51) Int. Cl.
*C07H 15/04* (2006.01)
*A61K 45/06* (2006.01)
*A61K 47/26* (2006.01)

(52) U.S. Cl.
CPC ............. *C07H 15/04* (2013.01); *A61K 45/06* (2013.01); *A61K 47/26* (2013.01)

(58) Field of Classification Search
None
See application file for complete search history.

(56) References Cited

U.S. PATENT DOCUMENTS 4,464,469 A * 8/1984 Parr ............... C12Y 305/02006
435/207

FOREIGN PATENT DOCUMENTS

| EP | 0 233 837 A2 | 8/1987 |
|---|---|---|
| FR | 3 022 458 A1 | 12/2015 |
| JP | 2016 113578 A | 6/2016 |
| WO | WO 95/18971 A1 | 7/1995 |
| WO | WO 2007/097652 A2 | 8/2007 |
| WO | WO 2014/202416 A1 | 12/2014 |
| WO | WO 2015/137838 A1 | 9/2015 |

OTHER PUBLICATIONS

Moynihan, Carbohydrate Research 374 (2013) 29-39. (Year: 2013).*
Amachi, Methods in Enzymology (1979), 62, 227-36. (Year: 1979).*
Kawai, Methods in Enzymology, vol. 62, 1979. (Year: 1979).*
Registry No. 26234-56-0, which entered STN on Nov. 16, 1984. (Year: 1984).*
Silva, Extremophiles (1999) 3: 163-172. (Year: 1999).*
Collins, J. Chem. Soc. Perkin Trans. I, 1984, pp. 1525-1530. (Year: 1984).*
Sheen, Carbohydrate Research, 23 (1972) 87-102. (Year: 1972).*
Astill, et al., "The toxicology and fate of 2,2,4-trimethyl-1,3-pentanediol diisobutyrate", Toxicology and Applied Pharmacology, Academic Press, Amsterdam, NL, Jul. 1, 1972, vol. 22, No. 3, pp. 387-399.
Faria, et al., "Design of new enzyme stabilizers inspired by glycosides of hyperthermophilic microorganisms", Carbohydrate Research, Pergamon, GB, Dec. 8, 2008, vol. 343, No. 18, pp. 3025-3033.
Hamon, et al., "Synthesis of Mannosylglycerate Derivatives as Immunostimulating Agents: Synthesis of Mannosylglycerate Derivatives as Immunostimulating Agents", European Journal of Organic Chemistry, Sep. 1, 2017, vol. 2017, No. 32, pp. 4803-4891.
Hermansson, et al., "Isolation and Characterization of 2-0-beta-D-glucopyranosyl-L-malic acid from Synadenium Pereskiifolium", Phytochemistry, Pergamon Press, GB, Jan. 1, 1990, vol. 29, No. 2, pp. 513-515.
Kanapathipillai, et al., "Small stress molecules inhibit aggregation and neurotoxicity of prion peptide 106-126", Biochemical and Biophysical Research Communications, Elsevier, Amsterdam, NL, Nov. 26, 2007, vol. 365, No. 4, pp. 808-813.
Le Dang, et al., "Antimicrobial Activities of Novel Mannosyl Lipids Isolated from the Biocontrol Fungus *Simplicillium lamellicola* BCP against Phytopathogenic Bacteria", Journal of Agricultural and Food Chemistry, Apr. 16, 2014, vol. 62, No. 15, pp. 3363-3370.
Li, et al., "Antioxidant and Quinone Reductase-Inducing Constituents of Black Chokeberry (*Aronia melanocarpa*) Fruits", Journal of Agricultural and Food Chemistry, Nov. 21, 2012, vol. 60, No. 46, pp. 11551-11559.
Listkowski, et al., "Carboxymethylglycoside lactones (CMGLs) : structural variations on the carbohydrate moiety", Tetrahedron Asymmetry, Pergamon Press LTD, Oxford, GB, Oct. 12, 2007, vol. 18, No. 18, pp. 2201-2210.
Picmanová, et al., "A recycling pathway for cyanogenic glycosides evidenced by the comparative metabolic profiling in three cyanogenic plant species", Biochemical Journal, Jun. 11, 2015, vol. 469, No. 3, pp. 375-389.
Roling, et al., "Layer-by-Layer Deposition of Vesicles Mediated by Supramolecular Interactions", Langmuir, Aug. 13, 2013, vol. 29, No. 32, pp. 10174-10182.
Russa, et al., "Characterization of Lipopolysaccharides from Rhizobium meliloti strain 102F51 and its nonnodulating mutant WL113", Archives of Microbiology, Springer Berlin, Heidelberg, Jan. 1, 1996, vol. 165, No. 1, pp. 26-33.
Saunders, et al., "The acid hydrolysis of glycosides", Carbohydrate Research, Dec. 1, 1967, vol. 5, No. 4, pp. 453-460.
Suzuki, et al., "3-O-beta-D-Glucopyranosyl-(3S)-hydroxybutanolide (Goodyeroside A) ", Journal of Carbohydrate Chemistry, Jan. 1, 2005, vol. 24, No. 1, pp. 83-84.

(Continued)

*Primary Examiner* — Layla D Berry
(74) *Attorney, Agent, or Firm* — Gary J. Gershik

(57) ABSTRACT

The compounds of the present invention are useful for stabilizing biological molecules, particularly in the presence of pH and thermal stress.

20 Claims, 5 Drawing Sheets

(56) References Cited

OTHER PUBLICATIONS

Vuorinen, "2-C-carboxyaldoses and aldonic acids from cellobiose, maltose, and 4-0-methyl-D-glucose with 2-anthraquinone-sulfonic acid", Carbohydrate Research, Sep. 1, 1985, vol. 141, No. 2, pp. 307-317.
Wang Xin, et al., "Development of a UPLC-MS/MS method for determining gamma-hydroxybutyric acid (GHB) and GHB glucuronide concentrations in hair and application to forensic cases", Forensic Toxiciology, Tokyo: Springer, Tokyo, Jul. 24, 2015, vol. 34, No. 1, pp. 51-60.
International Search Report issued in connection with PCT International Application No. PCT/IB2018/001411.
Written Opinion (form PCT/ISA/237) issued in connection with PCT International Application No. PCT/IB2018/001411.
International Preliminary Report on Patentability issued May 19, 2020 in connection with PCT/IB2018/001411.
First Examination Report issued on Dec. 27, 2021 in connection with Indian Patent Application No. 202017020956.
Oyetayo, O. et al., "Diversity selection, screening and quantitative structure-activity relationships of somolyte-like additive effects on the thermal stability of a monoclonal antibody", *Institute of Applied Biotechnology*, Jul. 28, 2016 pp. 151-157.
Canepa, J. et al., "Characterizing osmolytes chemical class hierarchies and functional group requirements for thermal stabilization of proteins", *Department of Chemistry & Biochemistry, California Polytech State University*, Jun. 12, 2020.
Pucci, F. et al., "Protein Thermostability Prediction within Homologous Families Using Temperature-Dependent Statistical Potentials", vol. 9. Mar. 19, 2014.
Office Action issued Jan. 28, 2023 in connection with corresponding Chinese Patent Application No. 2104022021.6, including English language translation.
Office Action issued Feb. 27, 2023 in connection with corresponding Brazilian Patent Application No. BR112020009453-6, including English language translation.
Communication pursuant to Article 94(3)EPC issued Mar. 2, 2023 in connection with European Patent Application No. 18 833 997. 2-1110.
Decision of Rejection issued Oct. 3, 2023 in connection with corresponding Japanese Patent Application No. 2020-544996, including English language translation.
Intellectual Property of India Hearing letter dispatched Jan. 11, 2023 in connection with corresponding Indian Application No. 202017020956.
Nymann Petersen, I.; Langgaard Kristensen, J.; Tortzen, C.; Breindahl, T.; Sejer Pedersen, D. Beilstein J. Org. Chem. 2013, 9, 641-646. doi:10.3762/bjoc.9.72.
Ping Zhou, Tong An, Chuan Zhao, Yuan Li, Rongshan Li, Rui Yang, Yinsong Wang, Xiujun Gao, Lactosylated PLGA nanoparticles containing $\epsilon$-polylysine for the sustained release and liver-targeted delivery of the negatively charged proteins, International Journal of Pharmaceutics, vol. 478, Issue 2, 2015, pp. 633-643, ISSN 0378-5173, https://doi.org/10.1016/j.ijpharm.2014.12.017.
Cho HR, Lee Y, Doble P, Bishop D, Hare D, Kim YJ, Kim KG, Jung HS, Park KS, Choi SH, Moon WK. Magnetic resonance imaging of the pancreas in streptozotocin-induced diabetic rats: Gadofluorine P and Gd-DOTA. World J Gastroenterol 2015; 21(19): 5831-5842.
Tadashi Ishii, Junji Ichita, Hajime Matsue, Hiroshi Ono, Ikuko Maeda, Fluorescent labeling of pectic oligosaccharides with 2-aminobenzamide and enzyme assay for pectin, Carbohydrate Research, vol. 337, Issue 11, 2002, pp. 1023-1032, ISSN 0008-6215, https://doi.org/10.1016/80008-6215(02)00087-3.
Yu F, Jiang T, Zhang J, Cheng L, Wang S. Galactosylated liposomes as oligodeoxynucleotides carrier for hepatocyte-selective targeting. Pharmazie. Jul. 2007;62(7):528-33. PMID: 17718195.

\* cited by examiner

NEUTRAL GLYCOSYLATED AMIDES AND DIANIONIC GLUCURONIDATED ACIDS AS STABILIZERS FOR BIOLOGICAL MOLECULES

CROSS-REFERENCE TO RELATED APPLICATIONS

This application is a §371 national stage of PCT International Application No. PCT/IB2018/001411, filed Nov. 13, 2018, claiming the benefit U.S. Provisional Application No. 62/585,341, filed Nov. 18, 2017, the contents of which is hereby incorporated by reference into the application.

Throughout this application, certain publications are referenced in parentheses. Full citations for these publications may be found immediately preceding the claims. The disclosures of these publications in their entireties are hereby incorporated by reference into this application in order to describe more fully the state of the art to which this invention relates.

BACKGROUND OF THE INVENTION

Proteins and other biological molecules suffer degradation when exposed to pH and thermal stresses due to denaturation, aggregation and other adverse chemical and physical modifications (Chang et al. 2010; Ueda et al. 2001). Such pH and thermal stresses can occur during processing, formulation or storage of biological molecules. For biological molecules having therapeutic applications, degradation results in lower yield and loss of activity.

Physical stresses such as heating or freeze drying can result in loss of native structure and thus activity of biological molecules. Chemical stresses such as low or high pH also degrade the structure of biological molecules, resulting aggregation, misfolding or precipitation of the biological molecules (Chang et al. 2010). For therapeutic biological molecules, some formulations require low or high pH for specific drug release needs, but such pH conditions can also adversely effect stability and thus shelf life of the therapeutic molecule. Stabilization of biological molecules is particularly important when the biological molecules have therapeutic activity so that said activity does not diminish over time.

Certain carbohydrates have been shown to stabilize biological molecules exposed to adverse temperatures and other stresses (Ueda et al. 2001; Kaushik et al. 2003; Singer at al. 1998; Lin et al. 1996; Jain et al. 2009; Andya et al. 2003; and Khan et al. 2010). One example is Trehalose, which is a disaccharide of glucose, linked by an alpha,alpha-1,1-glycosidic bond, that accumulates in many organisms, including bacteria, yeasts, fungi, plants and insects which withstand extended periods of dessication and inanimation. In several bacteria, trehalose is synthesised as a response to osmotic stress (Reed et al. 1986).

Trehalose has been used as an excipient in several biopharmaceuticals such as Avastin, Herceptin, Lucentis and Rituxan. (Ohtak et al. 2011). Addition of trehalose to several proteins and recombinant proteins increases their stability, as can be seen by the increase of their melting temperatures (Tm) (Kaushik et al. 2003; Lin et al. 1996; Singer et al. 1998; Ueda et al. 2001). One theory for the thermal stabilizing effect of trehalose is that when trehalose is added to a solution of protein it increases the surface tension of the medium leading to greater preferential hydration of the protein and thus increasing protein stability against degradation. Such compounds can be understood to shift equilibrium toward natively-folded conformations by raising the free energy of the unfolded state (Khan et al. 2010; Rajan et al. 2011).

Trehalose and saccharose have been studied as stabilizers in freeze-dried formulations of a recombinant monoclonal antibodies. (Andya et al. 2003) One theory for the stabilizing effect of trehalose in dried formulations is that the trehalose interacts with the protein surface and serves as a water substitute which maintains structure of the biological molecule while resisting chemical and physical modification (Kaushik et al. 2003). Saccharose has also been shown to stabilize proteins from thermal degradation (Lee et al. 1981). Poly-amido-saccharides (PASs) have been shown to stabilize lysozyme toward dehydration and freezing stresses (Stidham et al. 2014).

Stabilization of biological molecules under pH stress remains a challenge. A particular challenge is stabilization of biological molecules under combined thermal and pH stress. New stabilisers are need which prevent degradation of biological molecules at low pH or high pH including when thermal stress is present.

SUMMARY OF THE INVENTION

The subject invention provides a compound having the structure:

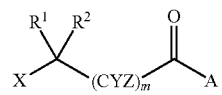

wherein
X is a hexosyl group selected from the group consisting of glucosyl, mannosyl, galactosyl, allosyl, altrosyl, gulosyl, idosyl and talosyl, or an uronic acid group selected from the group consisting of glucuronic acid, mannuronic acid, galacturonic acid, alluronic acid, altruronic acid, guluronic acid, iduronic acid and taluronic acid, or an uronic acid amide group selected from the group consisting of Glucuronamide, mannuronamide, galacturonamide, alluronamide, altruronamide, guluronamide, iduronamide and taluronamide;

each of $R^1$ and $R^2$ is independently H, halogen, OH, O-alkyl, $CONH_2$, $CO_2H$, $CO_2$-alkyl, or optionally substituted alkyl;

each of Y and Z is independently H, OH, O-alkyl or optionally substituted alkyl;

m is 0, 1 or 2; and $A=NR_3R_4$ or $OR_5$,
  wherein
  each of $R^3$ and $R^4$ is independently H, OH, O-alkyl or optionally substituted alkyl;
  $R^5$ is independently H or optionally substituted alkyl;
wherein
  when X is glucosyl, then $R^1$ is optionally substituted alkyl, and
  when each of $R^1$ and $R^2$ is H and m is 0, then X is other than glucuronic acid;
or a salt thereof.

The subject invention also provides a composition comprising a biological molecule and at least one compound of the present invention, and a method of stabilizing a biological molecule comprising treating the biological molecule with an effective amount of the compound of the present invention, so as to thereby stabilize the biological molecule.

DETAILED DESCRIPTION OF THE INVENTION

Figure 1:
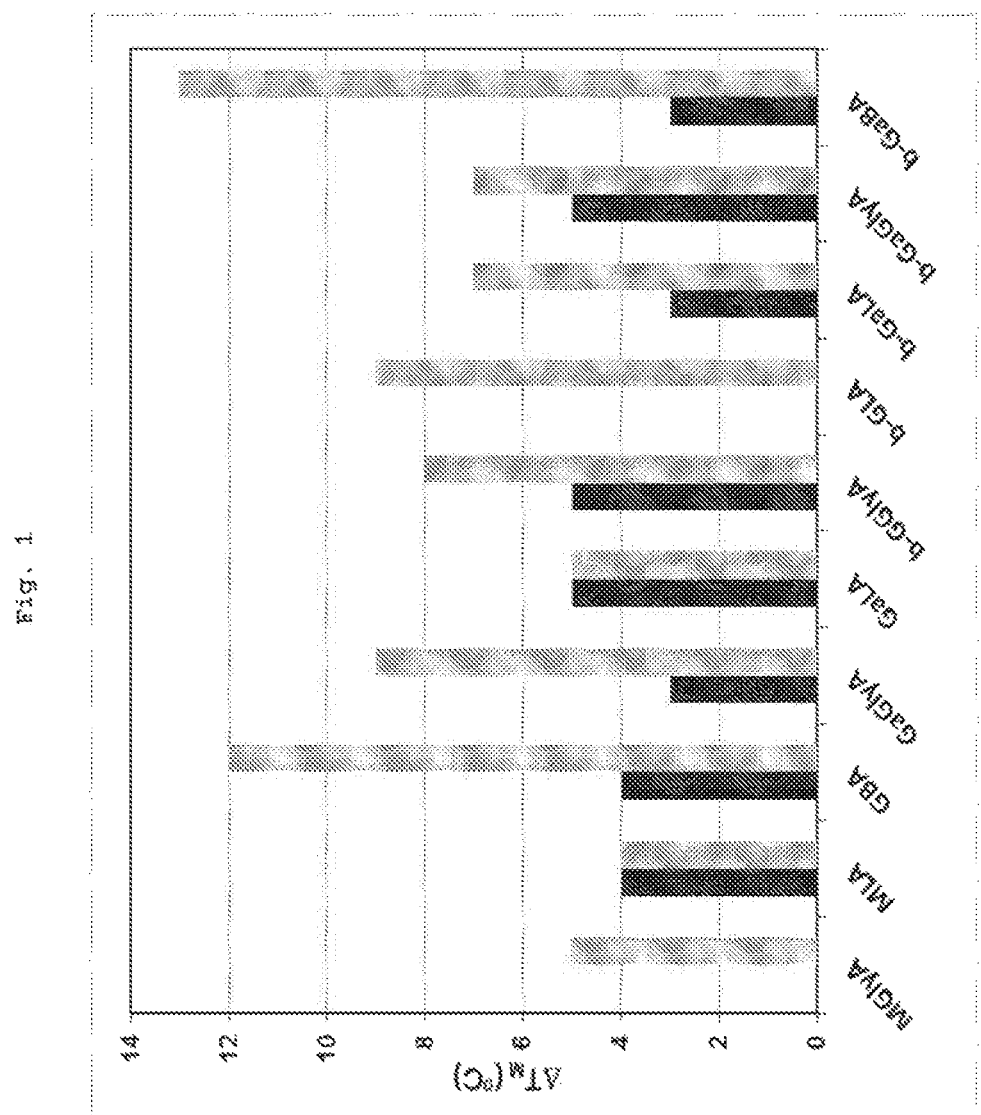
FIG. 1 shows the increase of the melting temperature (Tm) of lysozyme in the presence of 0.25 mM of various compounds (MGlyA, MLA, GBA, GaGlyA, GaLA, b-GGlyA, b-GLA, b-GaLA, b-GaGlyA, b-GaBA from left to right) in 25 mM sodium acetate buffer pH 3.6 (black bars) and in phosphate buffer at pH 12 (grey bars). The melting temperature (Tm) of Lysozyme in the absence of compounds was 71° C. in 25 mM sodium acetate buffer pH 3.6 and 55° C. in phosphate buffer at pH 12.

The present invention provides a compound having the structure:

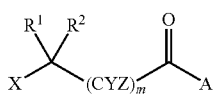

wherein
X is a hexosyl group selected from the group consisting of glucosyl, mannosyl, galactosyl, allosyl, altrosyl, gulosyl, idosyl and talosyl, or an uronic acid group selected from the group consisting of glucuronic acid, mannuronic acid, galacturonic acid, alluronic acid, altruronic acid, guluronic acid, iduronic acid and taluronic acid, or an uronic acid amide group selected from the group consisting of Glucuronamide, mannuronamide, galacturonamide, alluronamide, altruronamide, guluronamide, iduronamide and taluronamide;

each of $R^1$ and $R^2$ is independently H, halogen, OH, O-alkyl, $CONH_2$, $CO_2H$, $CO_2$-alkyl, or optionally substituted alkyl;
each of Y and Z is independently H, OH, O-alkyl or optionally substituted alkyl;
m is 0, 1 or 2; and
$A=NR_3R_4$ or $OR_5$,
wherein
each of $R^3$ and $R^4$ is independently H, OH, O-alkyl or optionally substituted alkyl;
$R^5$ is independently H or optionally substituted alkyl;
wherein
when X is glucosyl, then $R^1$ is optionally substituted alkyl, and
when each of $R^1$ and $R^2$ is H and m is 0, then X is other than glucuronic acid;
or a salt thereof.

The present invention provides a compound having the structure:

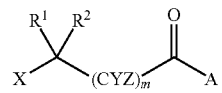

wherein
X is a hexosyl group selected from the group consisting of glucosyl, mannosyl, galactosyl, allosyl, altrosyl, gulosyl, idosyl and talosyl, or an uronic acid group selected from the group consisting of glucuronic acid, mannuronic acid, galacturonic acid, alluronic acid, altruronic acid, guluronic acid, iduronic acid and taluronic acid, or an uronic acid amide group selected from the group consisting of Glucuronamide, mannuronamide, galacturonamide, alluronamide, altruronamide, guluronamide, iduronamide and taluronamide;
each of $R^1$ and $R^2$ is independently H, halogen, OH, O-alkyl, $CONH_2$, $CO_2H$, $CO_2$-alkyl, or hydroxyalkyl;
each of Y and Z is independently H, OH, O-alkyl or hydroxyalkyl;
m is 0, 1 or 2; and
$A=NR_3R_4$ or $OR_5$,
wherein
each of $R^3$ and $R^4$ is independently H, OH, O-alkyl or optionally substituted alkyl;
$R^5$ is independently H or optionally substituted alkyl;
wherein
when X is glucosyl, then $R^1$ is optionally substituted alkyl, and
when each of $R^1$ and $R^2$ is H and m is 0, then X is other than glucuronic acid;
or a salt thereof.

In some embodiments, the compound having the structure:

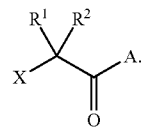

In some embodiments, wherein the optionally substituted alkyl is unsubstituted or substituted.
In some embodiments, wherein the optionally substituted alkyl is hydroxyalkyl.

In some embodiments, wherein the optionally substituted alkyl is alkyl-OH.

In some embodiments, wherein the optionally substituted alkyl is $C_1$-$C_4$ hydroxyalkyl.

In some embodiments, wherein the optionally substituted alkyl is $C_1$-$C_4$ alkyl-OH.

In some embodiments, wherein when X is glucosyl or mannosyl, m=0, one of $R^1$ or $R^2$ is -alkyl-OH and the other is —H, and A is —$NH_2$, then the compound is a beta-anomer.

In some embodiments, wherein
X is a hexosyl group selected from the group consisting of glucosyl, mannosyl, galactosyl, allosyl, altrosyl, gulosyl, idosyl and talosyl, or an uronic acid group selected from the group consisting of glucuronic acid, mannuronic acid, galacturonic acid, alluronic acid, altruronic acid, guluronic acid, iduronic acid and taluronic acid, or an uronic acid amide group selected from the group consisting of Glucuronamide, mannuronamide, galacturonamide, alluronamide, altruronamide, guluronamide, iduronamide and taluronamide;
each of $R^1$ and $R^2$ is independently H, $CONH_2$, $CO_2H$, $CO_2$-alkyl, or unsubstituted alkyl;
each of Y and Z is independently H;
m is 0, 1 or 2; and
A=$NR_3R_4$ or $OR_5$,
  wherein
    each of $R^3$ and $R^4$ is independently H, OH, O-alkyl or optionally substituted alkyl;
    $R^5$ is independently H or optionally substituted alkyl;
  wherein
    when X is glucosyl, then $R^1$ is unsubstituted alkyl, and
    when each of $R^1$ and $R^2$ is H and m is 0, then X is other than glucuronic acid;
or a salt thereof.

In some embodiments, wherein
X is a hexosyl group selected from the group consisting of glucosyl, mannosyl, galactosyl, allosyl, altrosyl, gulosyl, idosyl and talosyl, or an uronic acid group selected from the group consisting of glucuronic acid, mannuronic acid, galacturonic acid, alluronic acid, altruronic acid, guluronic acid, iduronic acid and taluronic acid, or an uronic acid amide group selected from the group consisting of Glucuronamide, mannuronamide, galacturonamide, alluronamide, altruronamide, guluronamide, iduronamide and taluronamide;
each of $R^1$ and $R^2$ is independently H, $CONH_2$, $CO_2H$, $CO_2$-alkyl, alkyl-OH, or unsubstituted alkyl;
each of Y and Z is independently H;
m is 0, 1 or 2; and
A=$NR_3R_4$ or $OR_5$,
  wherein
    each of $R^3$ and $R^4$ is independently H, OH, O-alkyl or optionally substituted alkyl;
    $R^5$ is independently H or optionally substituted alkyl;
  wherein
    when X is glucosyl, then $R^1$ is unsubstituted alkyl, and
    when each of $R^1$ and $R^2$ is H and m is 0, then X is other than glucuronic acid;
or a salt thereof.

The present invention provides compound having the structure:

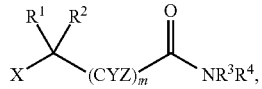

wherein
X is a hexosyl group selected from the group consisting of glucosyl, mannosyl, galactosyl, allosyl, altrosyl, gulosyl, idosyl and talosyl,
each of $R^1$ and $R^2$ is independently H, halogen, OH, O-alkyl, $CONH_2$, or optionally substituted alkyl,
each of $R^3$ and $R^4$ is independently H, OH, O-alkyl or optionally substituted alkyl,
each of Y and Z is independently H, OH, O-alkyl or optionally substituted alkyl,
m is 0, 1 or 2, and
when X is glucosyl, then $R^1$ is optionally substituted alkyl.

The present invention provides compound having the structure:

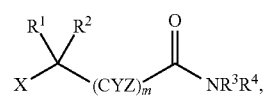

wherein
X is a hexosyl group selected from the group consisting of glucosyl, mannosyl, galactosyl, allosyl, altrosyl, gulosyl, idosyl and talosyl,
each of $R^1$ and $R^2$ is independently H, OH, O-alkyl or optionally substituted alkyl,
each of $R^3$ and $R^4$ is independently H, OH, O-alkyl or optionally substituted alkyl,
each of Y and Z is independently H, OH, O-alkyl or optionally substituted alkyl,
m is 0, 1 or 2, and
when X is glucosyl, then $R^1$ is optionally substituted alkyl.

In some embodiments, wherein X is glucosyl, mannosyl or galactosyl.

In some embodiments, wherein each of Y and Z is H.

In some embodiments, wherein each of $R^1$ and $R^2$ is H, or $R^1$ is $CH_3$ and $R^2$ is H, or $R^1$ is $CONH_2$ and $R^2$ is H, or R: is $CO_2CH_3$ and $R^2$ is H.

In some embodiments, wherein each of $R^3$ and $R^4$ is H.

In some embodiments, the compound having the structure:

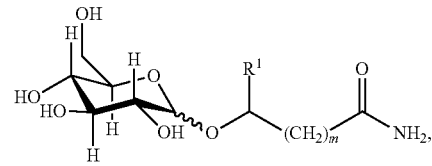

wherein $R^1$ is H, optionally substituted alkyl, or $CONH_2$ and m is 0, 1 or 2.

In some embodiments, the compound having the structure:

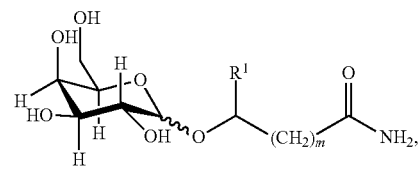

wherein R¹ is H, optionally substituted alkyl, or CONH₂ and m is 0, 1 or 2.

In some embodiments, the compound having the structure:

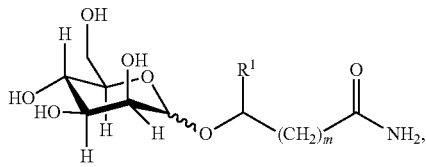

wherein R¹ is H, optionally substituted alkyl, or CONH₂ and m is 0, 1 or 2.

In some embodiments of the above compounds, R¹ is H, hydroxylalkyl, or CONH₂ and m is 0, 1 or 2.

In some embodiments, wherein m is 0. In some embodiments, wherein m is 1.

In some embodiments, wherein the hexosyl group is an alpha-anomer. In some embodiments, wherein the hexosyl group is a beta-anomer. In some embodiments, wherein the hexosyl group is a mix of alpha- and beta-anomers. In some embodiments, wherein the hexosyl group is a D-hexose. In some embodiments, wherein the hexosyl group is an L-hexose. In some embodiments, wherein the hexosyl group is a mix of D and L hexose.

In some embodiments, the compound having the structure:

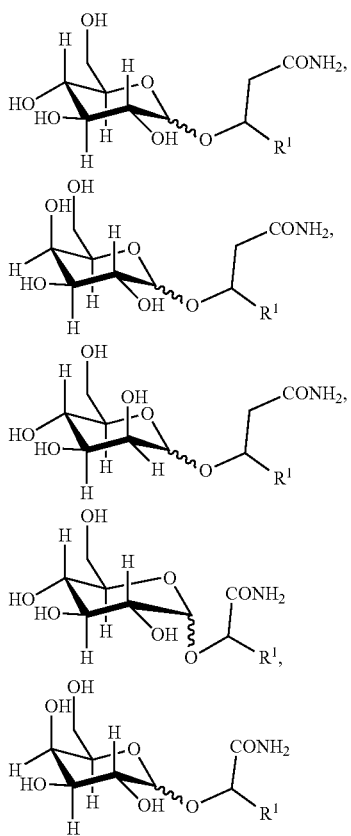

or

-continued

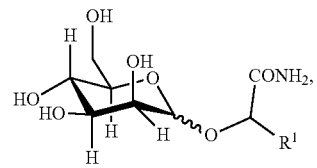

wherein R¹ is H, CONH₂ or optionally substituted alkyl.

In some embodiments of the above compounds, R¹ is hydroxyalkyl.

In some embodiments of the above compounds, R¹ is $C_1$-$C_4$ hydroxyalkyl.

In some embodiments, the compound having the structure:

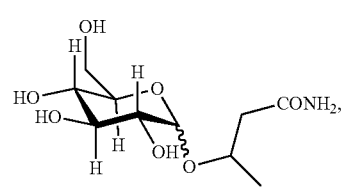

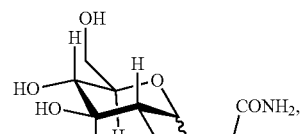

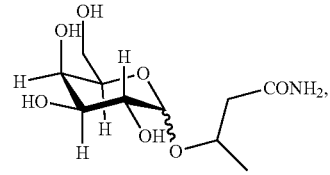

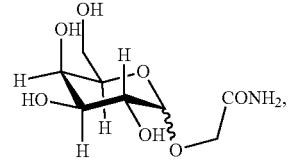

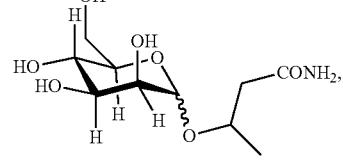

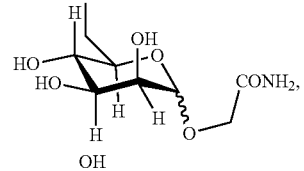

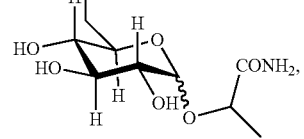

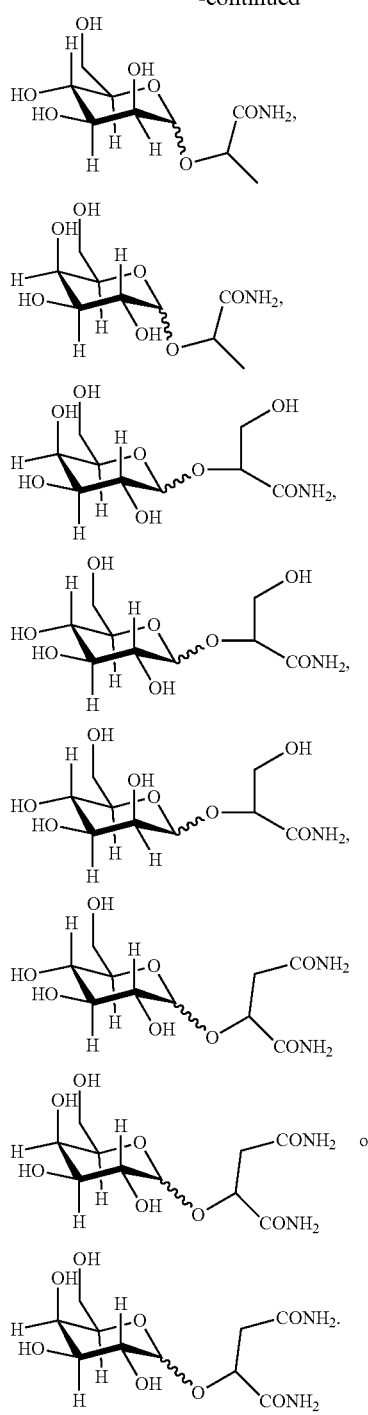
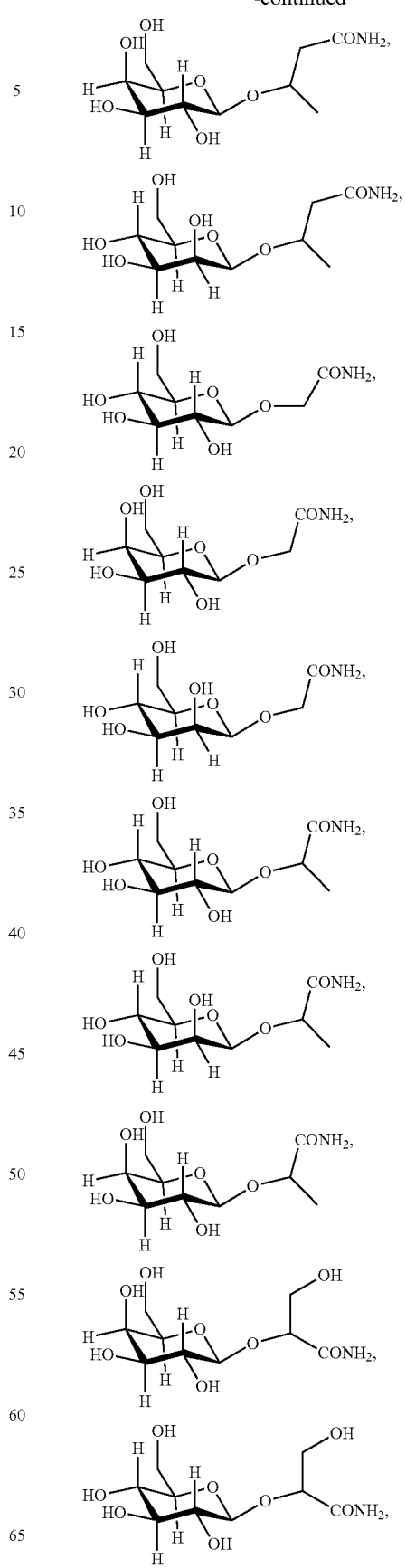
In some embodiments, the compound having the structure:
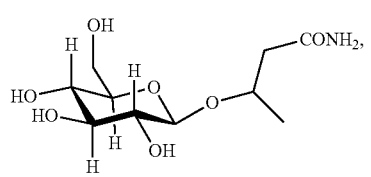

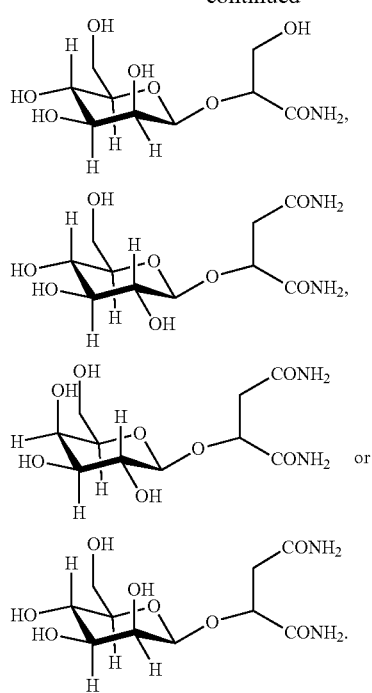
In some embodiments, the compound having the structure:
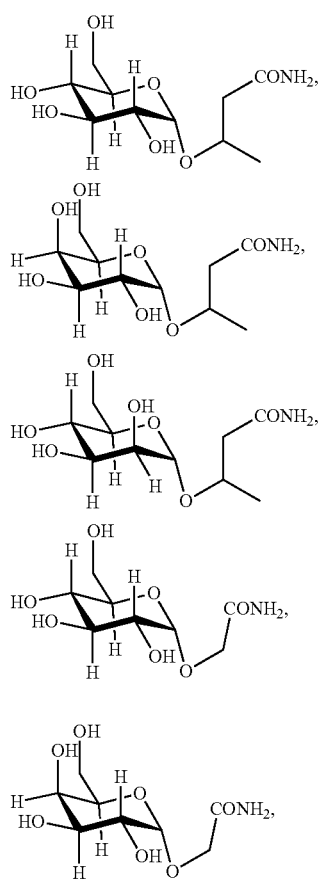
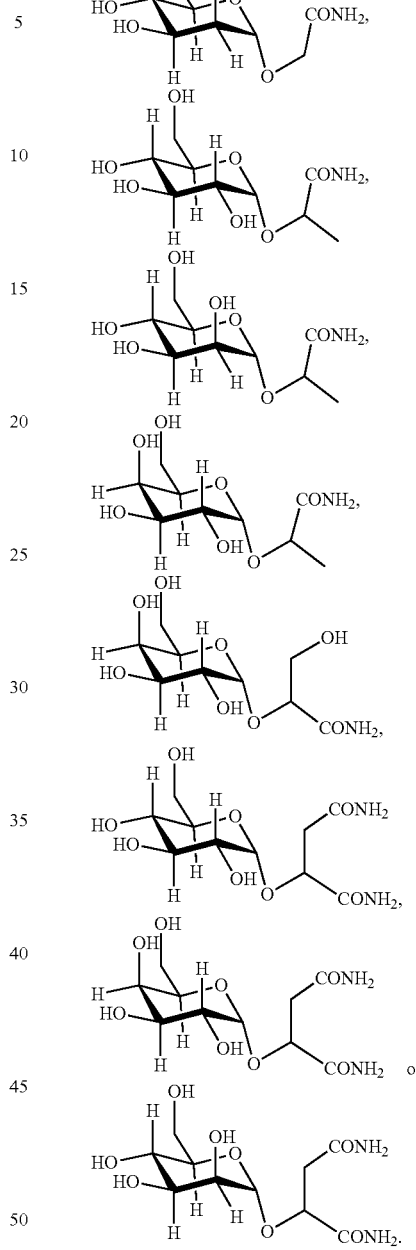
In some embodiments, the compound having the structure:
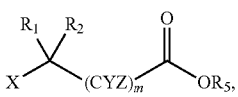
wherein
X is an uronic acid group selected from the group consisting of glucuronic acid, mannuronic acid, a galacturonic acid, alluronic acid, altruronic acid, guluronic acid, iduronic acid and taluronic acid, each of $R^1$ and $R^2$ is independently H, halogen, OH, O-alkyl, $CONH_2$, $CO_2H$, $CO_2$-alkyl, or optionally substituted alkyl;

each of Y and Z is independently H, OH, O-alkyl or optionally substituted alkyl, $R^5$ is independently H or optionally substituted alkyl, m is 0, 1 or 2, and when each of $R^1$ and $R^2$ is H and m is 0, then X is other than glucuronic acid;

or a salt thereof.

In some embodiments, the compound having the structure:

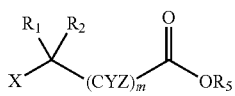

wherein

X is an uronic acid group selected from the group consisting of glucuronic acid, mannuronic acid, a galacturonic acid, alluronic acid, altruronic acid, guluronic acid, iduronic acid and taluronic acid, each of $R^1$ and $R^2$ is independently H, halogen, OH, O-alkyl, $CO_2H$, $CO_2$ (alkyl), or optionally substituted alkyl, each of Y and Z is independently H, OH, O-alkyl or optionally substituted alkyl, $R^5$ is independently H or optionally substituted alkyl, m is 0, 1 or 2, and when each of $R^1$ and $R^2$ is H and m is 0, then X is other than glucuronic acid;

or a salt thereof.

In some embodiments, the compound having the structure:

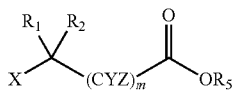

wherein

X is an uronic acid group selected from the group consisting of glucuronic acid, mannuronic acid, a galacturonic acid, alluronic acid, altruronic acid, guluronic acid, iduronic acid and taluronic acid, each of $R^1$ and $R^2$ is independently H, OH, O-alkyl or optionally substituted alkyl, each of Y and Z is independently H, OH, O-alkyl or optionally substituted alkyl, $R^5$ is independently H or optionally substituted alkyl, m is 0, 1 or 2, and when each of $R^1$ and $R^2$ is H and m is 0, then X is other than glucuronic acid;

or a salt thereof.

In some embodiments, the compound wherein

X is an uronic acid group selected from the group consisting of glucuronic acid, mannuronic acid, a galacturonic acid, alluronic acid, altruronic acid, guluronic acid, iduronic acid and taluronic acid, each of $R^1$ and $R^2$ is independently H, $CONH_2$, $CO_2H$, $CO_2$-alkyl, or unsubstituted alkyl;

each of Y and Z is H;

$R^5$ is independently H or optionally substituted alkyl, m is 0, 1 or 2, and when each of $R^1$ and $R^2$ is H and m is 0, then X is other than glucuronic acid;

or a salt thereof.

In some embodiments, wherein X is glucuronic acid, mannuronic acid or a galacturonic acid.

In some embodiments, wherein each of Y and Z is H.

In some embodiments, wherein each of $R^1$ and $R^2$ is H, or $R^1$ is $CH_3$ and $R^2$ is H, or $R^1$ is $CO_2CH_3$ and $R^2$ is H.

In some embodiments, wherein each of $R^5$ is H or $CH_3$.

In some embodiments, the compound having the structure:

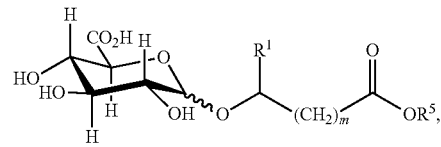

wherein $R^1$ is H, optionally substituted alkyl or $CO_2H$, $R^5$ is H, and m is 0, 1 or 2, or a salt thereof.

In some embodiments, the compound having the structure:

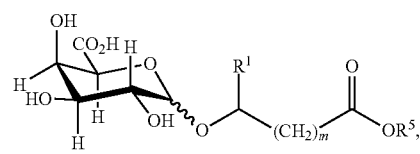

wherein $R^1$ is H, optionally substituted alkyl or $CO_2H$, $R^5$ is H, and m is 0, 1 or 2, or a salt thereof.

In some embodiments of the above compounds, $R^1$ is H, hydroxylalkyl, or $CO_2H$, $R^5$ is H and m is 0, 1 or 2.

In some embodiments, the compound having the structure:

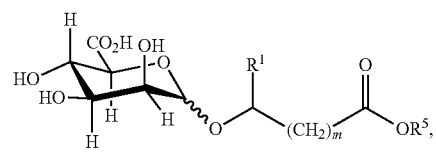

wherein $R^1$ is H, optionally substituted alkyl or $CO_2H$, $R^5$ is H, and m is 0, 1 or 2, or a salt thereof.

In some embodiments, wherein m is 0. In some embodiments, wherein m is 1.

In some embodiments, wherein the uronic acid group is an alpha-anomer. In some embodiments, wherein the uronic acid group is a beta-anomer. In some embodiments, wherein the uronic acid group is a D-uronic acid. In some embodiments, wherein the uronic acid group is an L-uronic acid. In some embodiments, wherein the uronic acid group is a mix of D and L.

In some embodiments the compound having the structure:
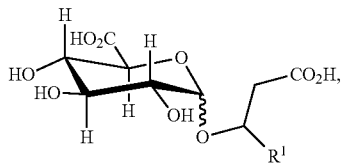
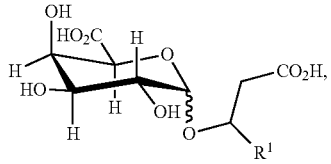
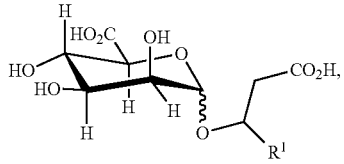
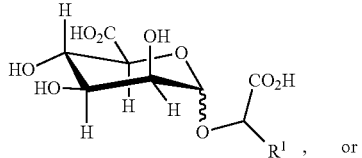
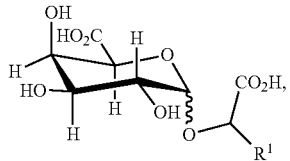, or
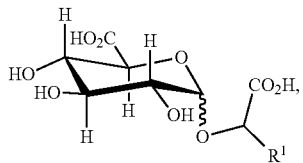
wherein R¹ is H, optionally substituted alkyl or CO₂H; or a salt thereof.
In some embodiments the compound having the structure:
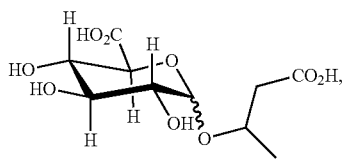
wherein R¹ is optionally substituted alkyl or CO₂H; or a salt thereof.
In some embodiments the compound having the structure:
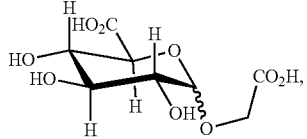
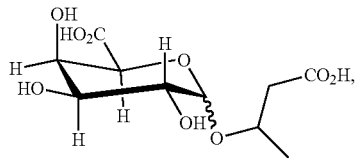
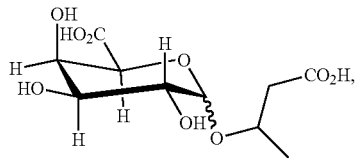
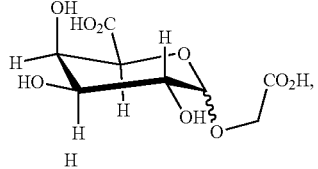
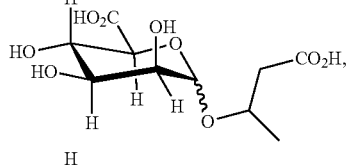
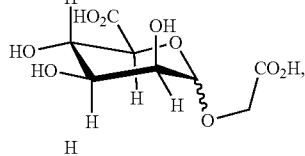
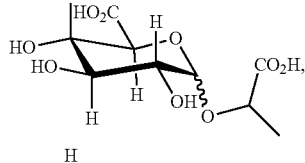
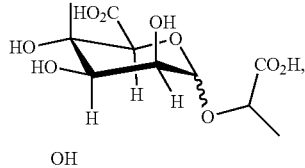
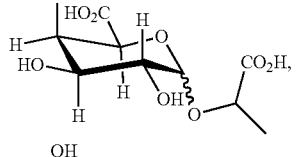
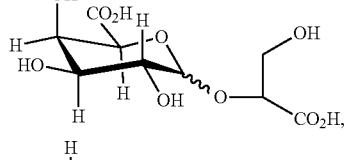
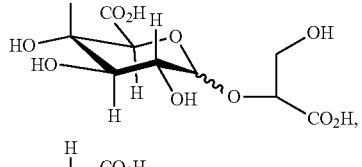
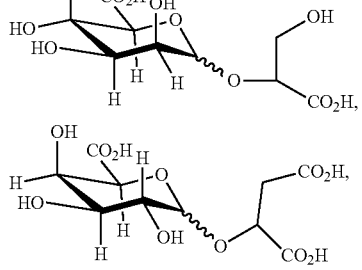

-continued
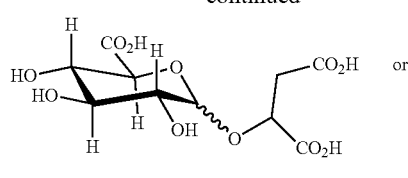 or
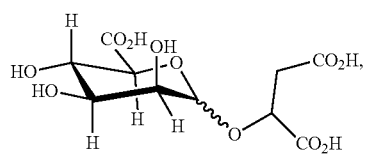
or a salt thereof.
In some embodiments the compound having the structure:
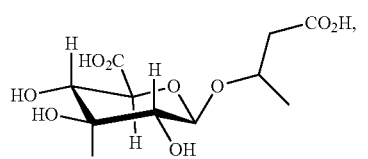
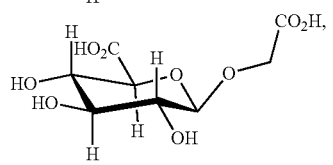
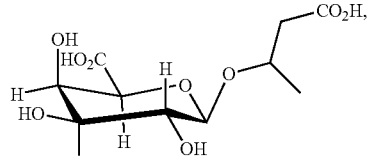
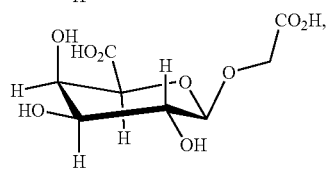
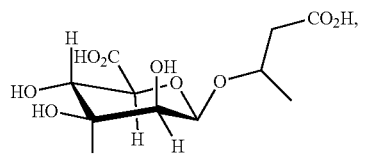
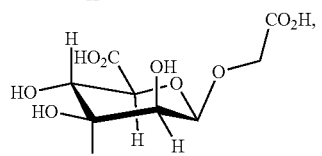
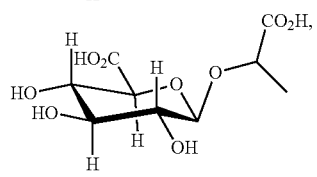
-continued
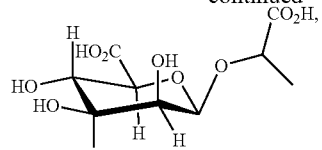
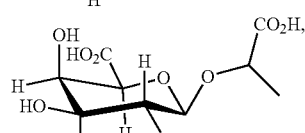
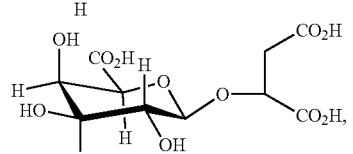
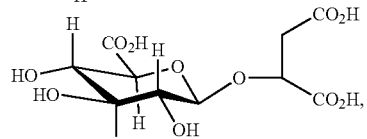
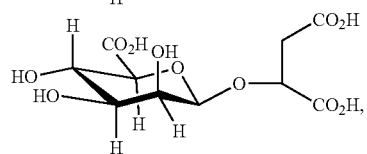
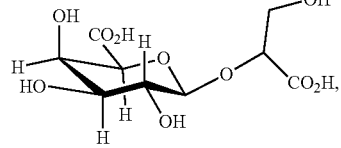
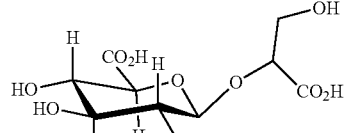
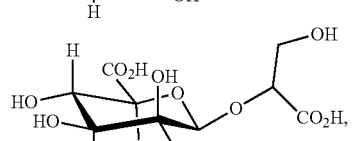 or
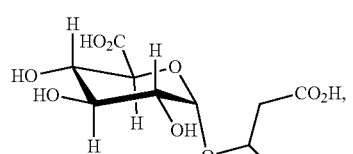
or a salt thereof.
In some embodiments the compound having the structure:
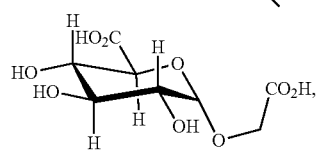

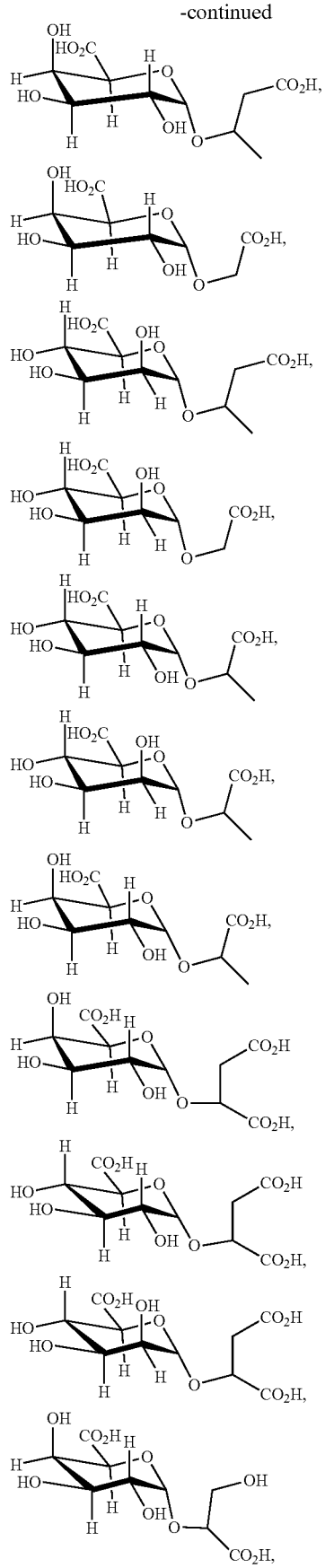
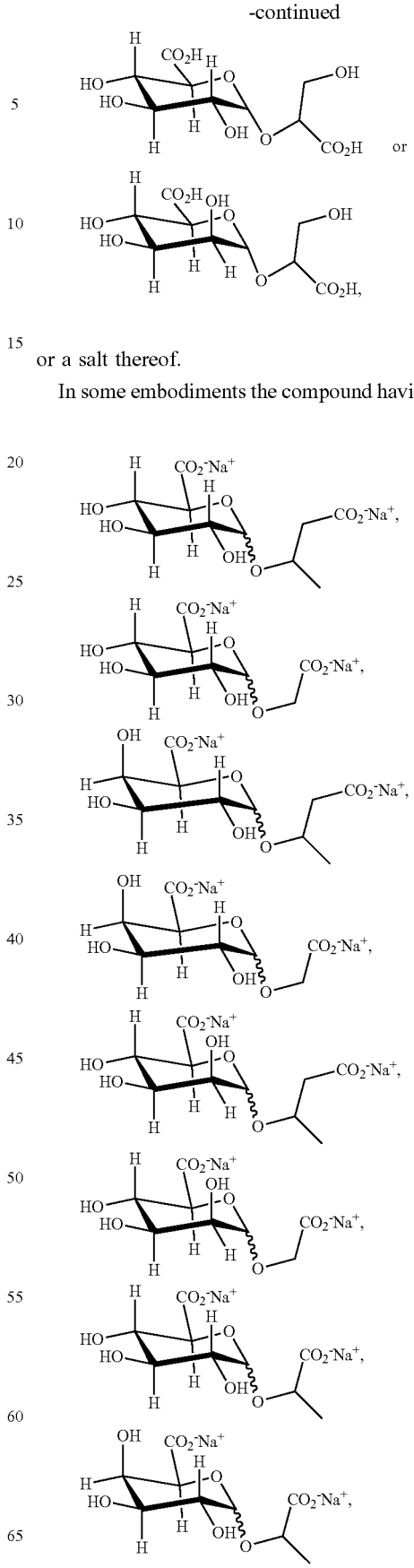
or a salt thereof.
In some embodiments the compound having the structure:
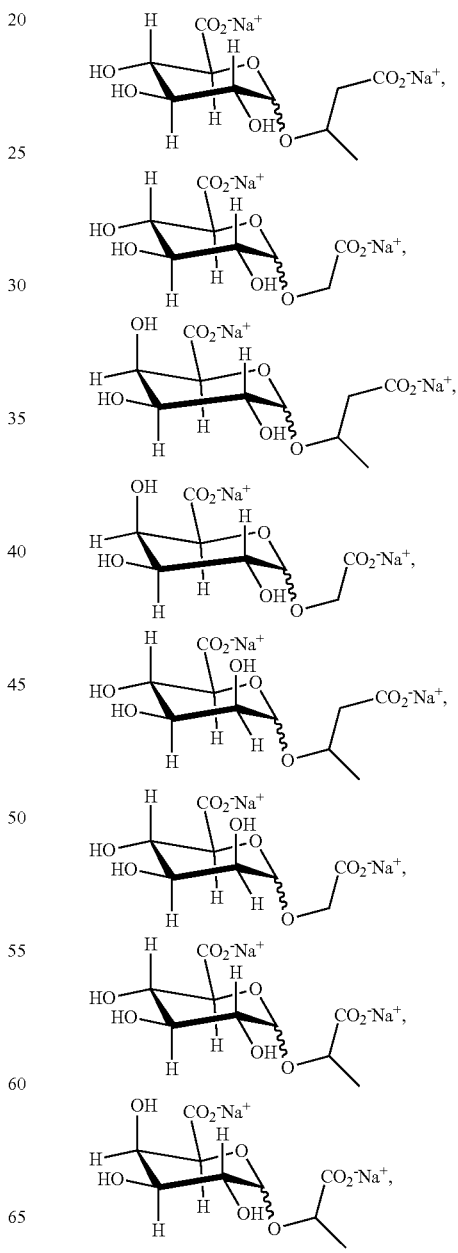

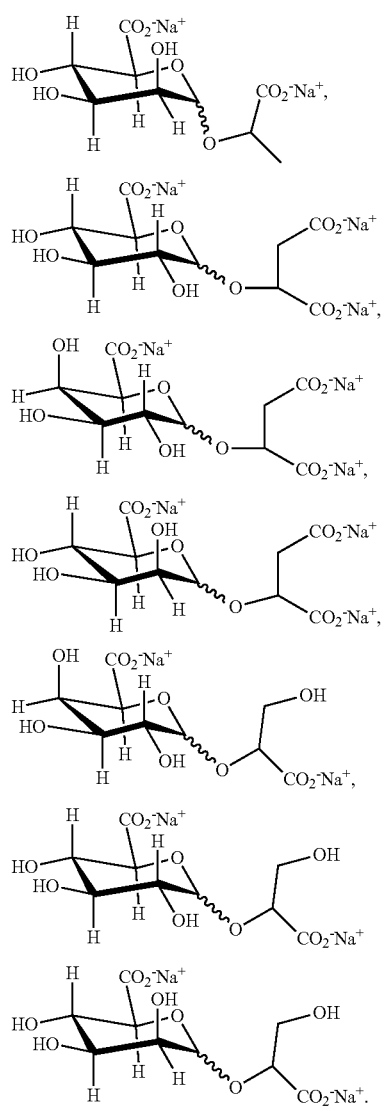
In some embodiments the compound having the structure:
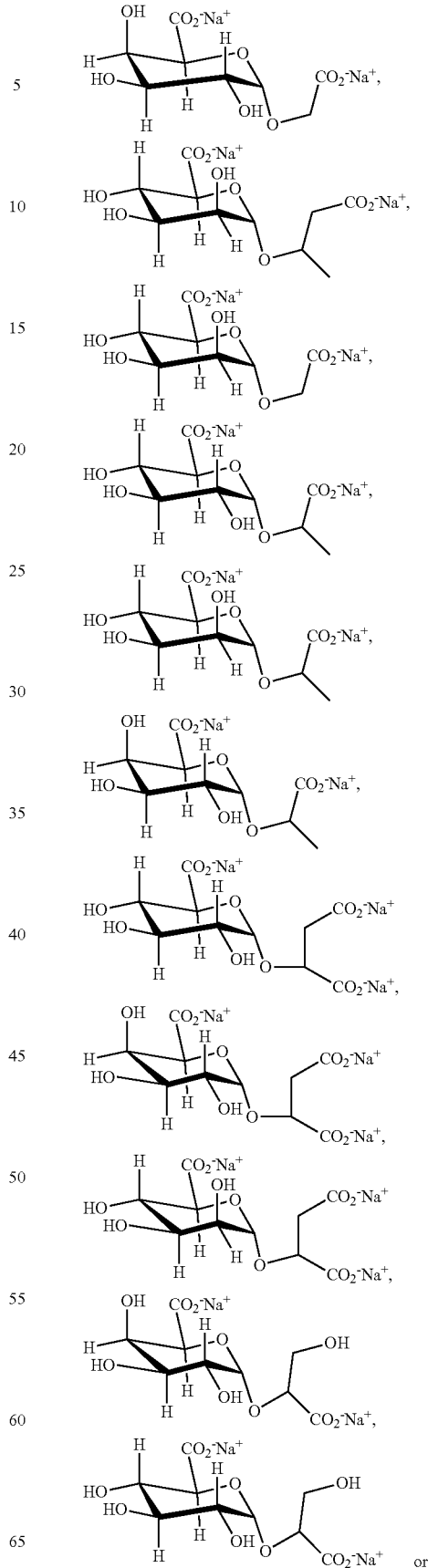

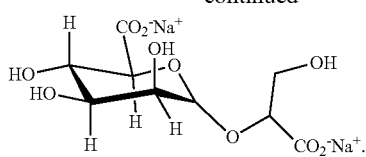

In some embodiments the compound having the structure:

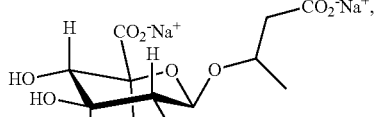

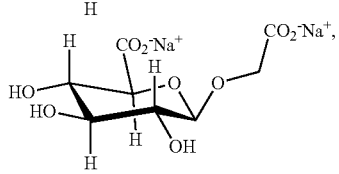

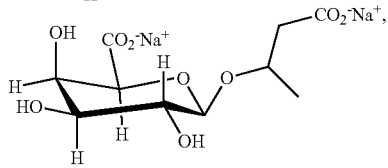

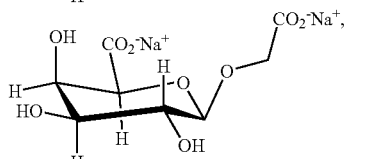

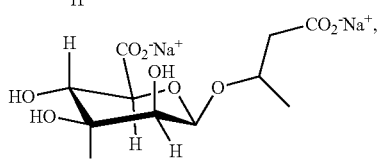

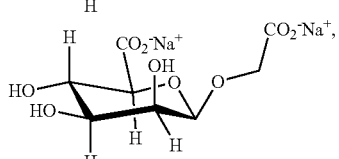

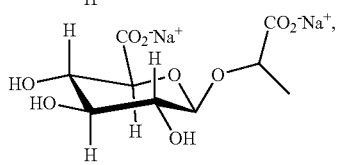

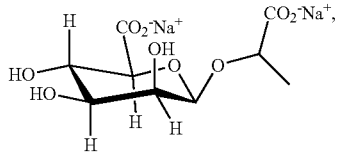

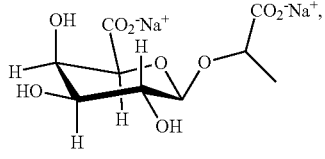

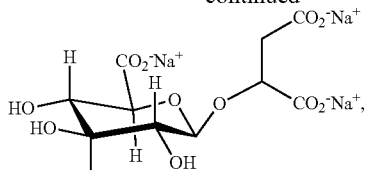

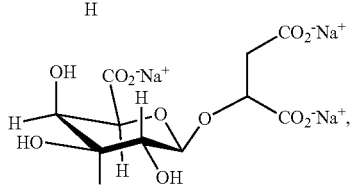

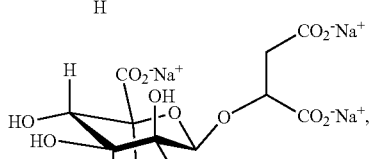

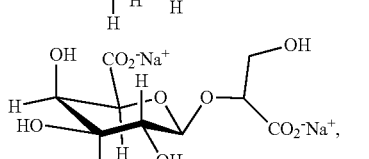

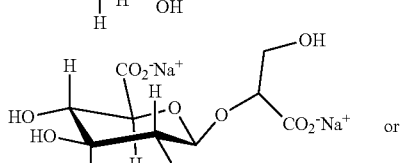

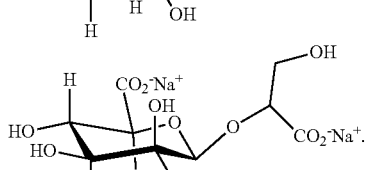

or

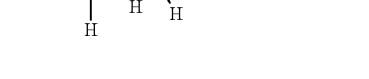

In some embodiments, wherein the compound is a potassium salt, calcium salt or magnesium salt.

In some embodiments, wherein the compound is a sodium salt.

In some embodiments the compound having the structure:

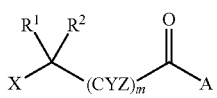

wherein

X is a uronic acid amide group selected from the group consisting of Glucuronamide, mannuronamide, galacturonamide, alluronamide, altruronamide, guluronamide, iduronamide and taluronamide;

each of $R^1$ and $R^2$ is independently H, halogen, OH, O-alkyl, $CONH_2$, $CO_2H$, $CO_2$-alkyl, or optionally substituted alkyl;

each of Y and Z is independently H, OH, O-alkyl or optionally substituted alkyl;

m is 0, 1 or 2; and $A=NR_3R_4$, wherein
each of $R^3$ and $R^4$ is independently H, OH, O-alkyl or optionally substituted alkyl;
or a salt thereof.

In some embodiments the compound having the structure:

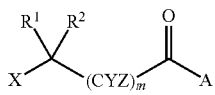

wherein
X is a uronic acid amide group selected from the group consisting of glucuronamide, mannuronamide, galacturonamide, alluronamide, altruronamide, guluronamide, iduronamide and taluronamide;
each of $R^1$ and $R^2$ is independently H, $CONH_2$, $CO_2H$, $CO_2$-alkyl, alkyl-OH or unsubstituted alkyl;
each of Y and Z is H;
m is 0, 1 or 2; and
$A = NR_3R_4$,
wherein
each of $R^3$ and $R^4$ is independently H, OH, O-alkyl or optionally substituted alkyl;
or a salt thereof.

In some embodiments, wherein X is a uronic acid amide group selected from the group consisting of glucuronamide, mannuronamide, galacturonamide.

In some embodiments, wherein each of Y and Z is H.

In some embodiments, wherein each of $R^1$ and $R^2$ is H, or $R^1$ is $CH_3$ and $R^2$ is H, or $R^1$ is $CONH_2$ and $R^2$ is H.

In some embodiments, wherein each of $R^3$ and $R^4$ are each H.

In some embodiments the compound having the structure:

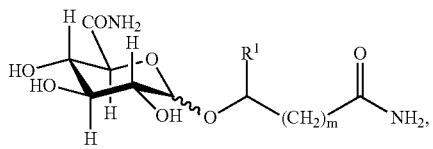

wherein $R^1$ is H, optionally substituted alkyl, or $CONH_2$ and m is 0, 1 or 2.

In some embodiments the compound having the structure:

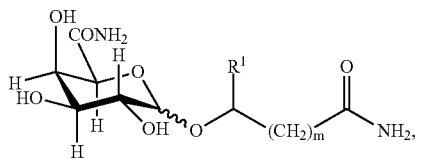

wherein $R^1$ is H, optionally substituted alkyl, or $CONH_2$ and m is 0, 1 or 2.

In some embodiments the compound having the structure:

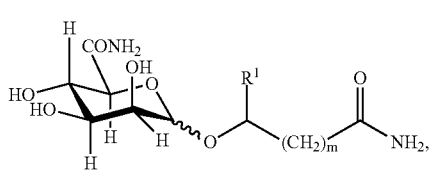

wherein $R^1$ is H, optionally substituted alkyl, or $CONH_2$ and m is 0, 1 or 2.

In some embodiments of the above compounds, $R^1$ is H, hydroxylalkyl, or $CONH_2$, and m is 0, 1 or 2.

In some embodiments, wherein m is 0.
In some embodiments, wherein m is 1.

In some embodiments, wherein the uronic acid amide group is an alpha-anomer. In some embodiments, wherein the uronic acid amide group is a beta-anomer. In some embodiments, wherein the uronic acid amide group is a D-uronic acid amide. In some embodiments, wherein the uronic acid amide group is an L-uronic acid amide. In some embodiments, wherein the uronic acid amide group is a mix of D and L.

In some embodiments the compound having the structure:

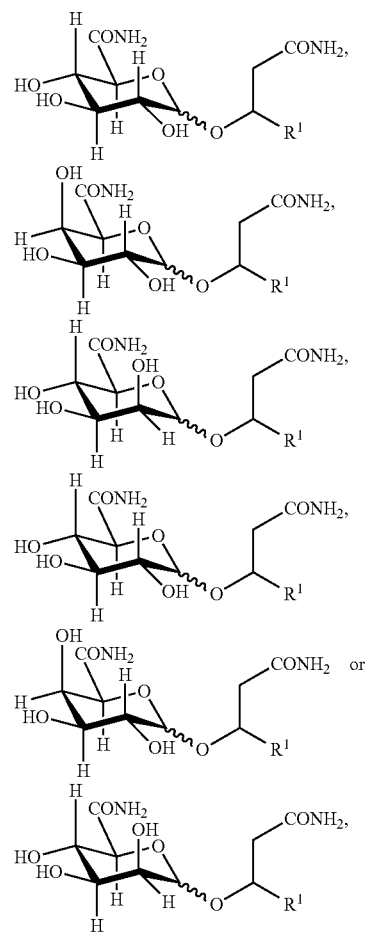

wherein $R^1$ is H, optionally substituted alkyl or $CONH_2$;
or a salt thereof.

In some embodiments the compound having the structure:

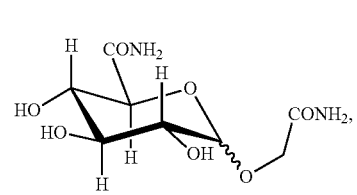

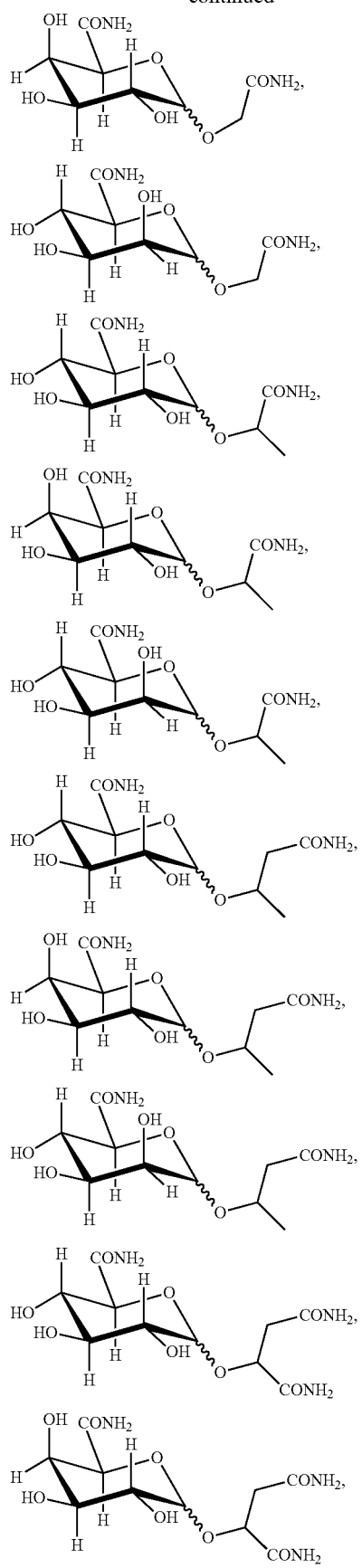
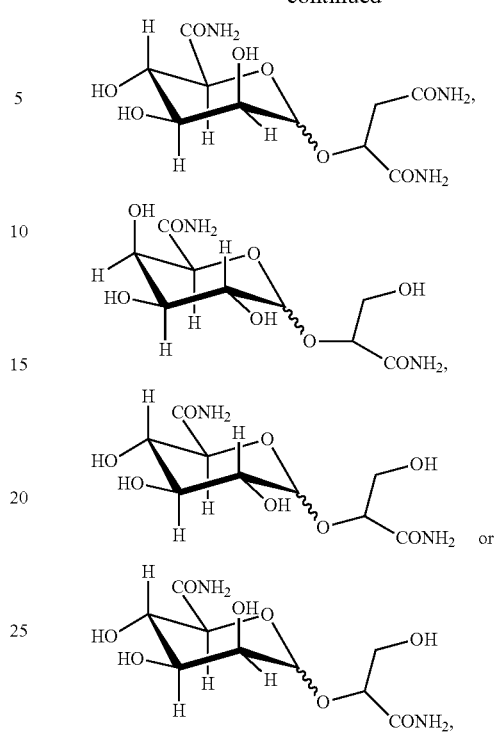
or salt thereof.
In some embodiments the compound having the structure:
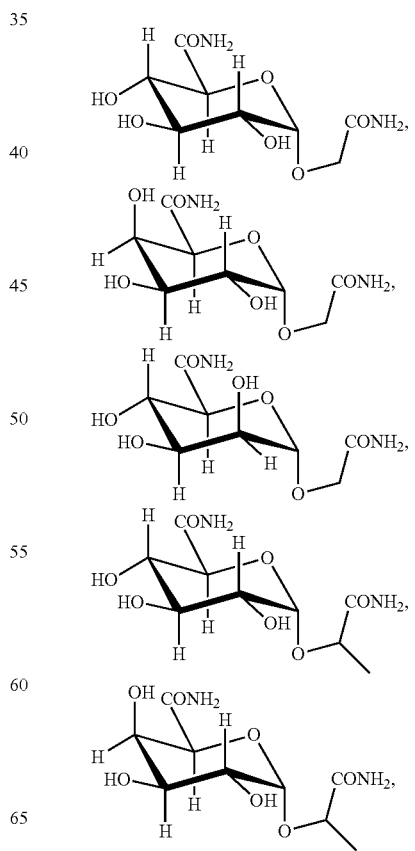

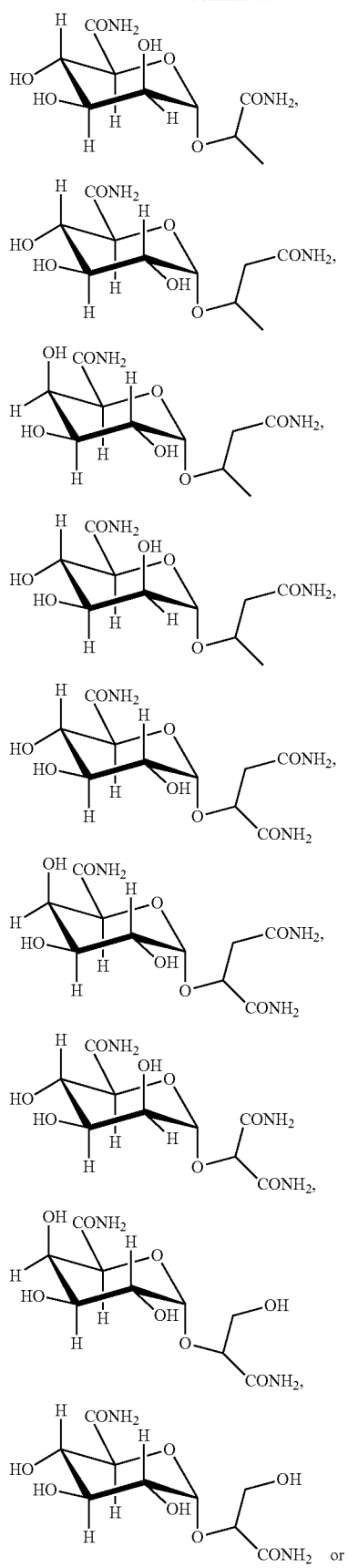
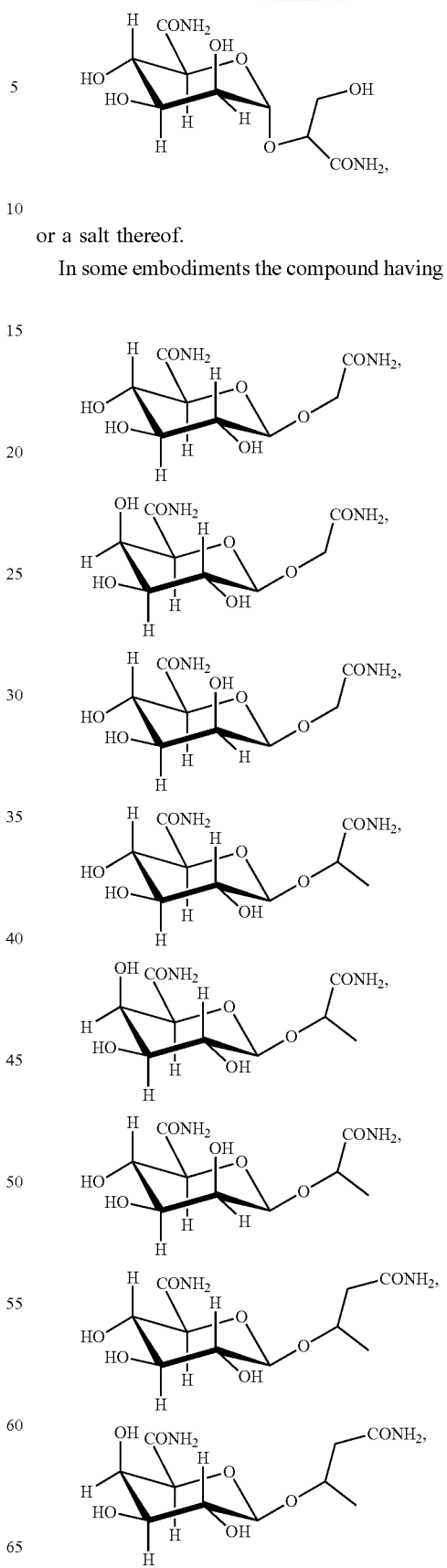
or a salt thereof.
In some embodiments the compound having the structure:

-continued

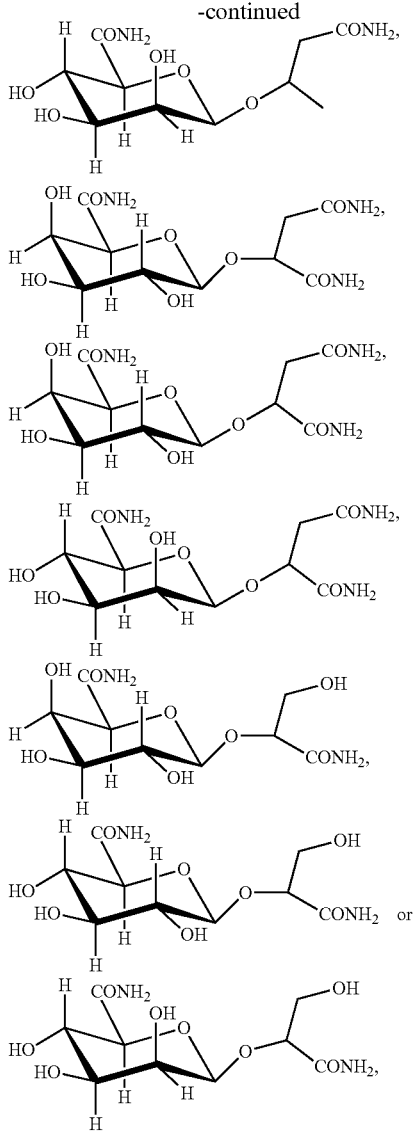

or a salt thereof.

In some embodiments, a composition comprising a biological molecule and at least one compound of the present invention.

In some embodiments, a composition comprising a biological molecule and a compound having the structure:

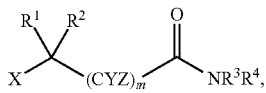

wherein
X is a hexosyl group selected from the group consisting of glucosyl, mannosyl and galactosyl,
each of $R^1$ and $R^2$ is independently H, halogen, OH, O-alkyl, $CONH_2$, or optionally substituted alkyl,
each of $R^3$ and $R^4$ is independently H, OH, O-alkyl or optionally substituted alkyl,
each of Y and Z is independently H, OH, O-alkyl or optionally substituted alkyl,
m is 0, 1 or 2.

In some embodiments, a composition comprising a biological molecule and a compound having the structure:

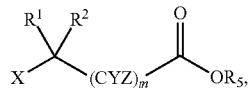

wherein
X is an uronic acid group selected from the group consisting of glucuronic acid, mannuronic acid and a galacturonic acid,
each of $R^1$ and $R^2$ is independently H, halogen, OH, O-alkyl, $CONH_2$, $CO_2H$, $CO_2$-alkyl, or optionally substituted alkyl;
each of Y and Z is independently H, OH, O-alkyl or optionally substituted alkyl,
$R^3$ is independently H or optionally substituted alkyl, and
m is 0, 1 or 2;
or a salt thereof.

In some embodiments, a composition comprising a biological molecule and a compound having the structure:

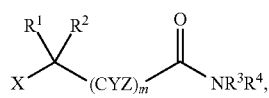

wherein
X is a uronic acid amide group selected from the group consisting of glucuronamide, mannuronamide and galacturonamide;
each of $R^1$ and $R^2$ is independently H, halogen, OH, O-alkyl, $CONH_2$, $CO_2H$, $CO_2$-alkyl, or optionally substituted alkyl;
each of $R^3$ and $R^4$ is independently H, OH, O-alkyl or optionally substituted alkyl,
each of Y and Z is independently H, OH, O-alkyl or optionally substituted alkyl;
m is 0, 1 or 2.

In some embodiments of the composition, wherein the biological molecule is a biopharmaceutical, protein, nucleotide, polypeptide or antibody.

In some embodiments of the composition, wherein the biological molecule has therapeutic activity.

In some embodiments of the composition, wherein the biological molecule is Insulin; Humulin; Novolin; Insulin human inhalation; Exubera; Insulin aspart; Novolog (aspart); Insulin glulisine; Apidra (glulisine); Insulin lispro; Humalog (lispro); Isophane insulin; NPH; Insulin detemir; Levemir (detemir); Insulin glargine; Lantus (glargine); Insulin zinc extended; Lente; Ultralente; Pramlintide acetate; Symlin; Growth hormone (GH); somatotropin; genotropin; humatrope; norditropin; NorlVitropin; Nutropin; Omnitrope; Protropin; Siazen; Serostim; Valtropin; Mecasermin; Increlex; Mecasermin rinfabate; IPlex; Factor VIII; Bioclate; Helixate; Kogenate; Recominate; ReFacto; Factor IX; Benefix; Antithromin III (AT-III); Thrombate III; Protein C concentrate; Ceprotin; β-Glucocerebrosidase; Cerezyme; β-Glucocerebrosidase; Ceredase (purified from pooled human placenta); Alglucosidase-α; Myozyme; Laronidase (α-1-iduronidase); Aldurazyme; Idursulphase (Iduronate-2-sulphatase); Elaprase; Galsulphase; Naglazyme; Agalsidase-R (human α-galactosidase A); Fabrazyme; α-1-Proteinase inhibitor; Aralast; Prolastin; Lactase; Lactaid;

Pancreatic enzymes (lipase, amylase, protease); Arco-Lase, Cotazym, Creon, Donnazyme, Pancrease, Viokase, Zymase, Adenosine deaminase (pegademase bovine, PEG-ADA); Adagen; Pooled immunoglobulins; Octagam; Human albumin; Albumarc; Albumin; Albuminar; AlbuRx; Albutein; Flexbumin; Buminate; Plasbumin; Erythropoietin; Epoetin-α; Epogen; Procrit; Darbepoetin-α; Aranesp; Filgrastim (granulocyte colony stimulating factor; G-CSF); Neupogen; Pegfilgrastim (Peg-G-CSF); Neulasta; Sargramostim (granulocytemacrophage colony stimulating factor; GM-CSF); Leukine; Oprelvekin (interleukinll; IL11); Neumega; Human follicle-stimulating hormone (FSH); Gonal-F; Follistim; Human chorionic gonadotropin (HCG); Ovidrel; Luveris; Type I alpha-interferon; interferon alfacon 1; consensus interferon; Infergen; Interferon-α2a (IFNα2a); Roferon-A; PegInterferon-α2a; Pegasys; Interferon-α2b (IFNα2b); Intron A; PegInterferon-α2b; Peg-Intron; Interferon-αn3 (IFNαn3); Alferon N; Interferon-β1a (rIFN-β); Avonex; Rebif; Interferon-β1b (rIFN-β); Betaseron; Interferon-γ1b (IFNγ); Actimmune; Aldesleukin (interleukin 2 (IL2); epidermal thymocyte activating factor; ETAF); Proleukin; Alteplase (tissue plasminogen activator; tPA); Activase; Reteplase (deletion mutein of tPA); Retavase; Tenecteplase; TNKase; Urokinase; Abbokinase; Factor VIIa; NovoSeven; Drotrecogin-α (activated protein C); Xigris; Salmon calcitonin; Fortical; Miacalcin; Teriparatide (human parathyroid hormone residues 1-34); Forteo; Exenatide; Byetta; Octreotide; Sandostatin; Dibotermin-α (recombinant human bone morphogenic protein 2; rhBMP2); Infuse; Recombinant human bone morphogenic protein 7 (rhBMP7); Osteogenic protein 1; Histrelin acetate (gonadotropin releasing hormone; GnRH); Supprelin LA; Vantas; Palifermin (keratinocyte growth factor KGF); kepivance; Becaplermin (platelet-derived growth factor; PDGF); Regranex; Trypsin; Granulex; Nesiritide; Natrecor; Botulinum toxin type A; Botox; Botulinum toxin type B; Myoblock; Collagenase; Santyl; Human deoxy-ribonuclease I; dornase-α; pulmozyme; Hyaluronidase (bovine, ovine); Amphadase (bovine); hydase (bovine); Vitrase (ovine); Hyaluronidase (recombinant human); hylenex; Papain; accuzyme; panafil; L-asparaginase; ELSPAR; Peg-asparaginase; Oncaspar; Rasburicase; Elitek; Lepirudin; Refludan; Bivalirudin; Angiomax; Streptokinase; Streptase; Anistreplase (anisoylated plasminogen streptokinase activator complex; APSAC); Eminase; Bevacizumab; Avastin; Cetuximab; Erbitux; Panitumumab; Vectibix; Alemtuzumab; Campath; Rituximab; Rituxan; Trastuzumab; Herceptin; Abatacept; Orencia; Anakinra; Antril; Kineret; Abalimumab; Humira; Etanercept; Enbrel; Infliximab; Remicade; Alefacept; Amevive; Natalizumab; Tysabri; Eculizumab; Soliris; Antithymocyte globulin (rabbit); Thymoglobulin; Basiliximab; Simulect; Daclizumab; Zenapax; Muromonab-CD3; Orthoclone; OKT3; Omalizumab; Xolair; Palivizumab; Synagis; Enfuvirtide; Fuzeon; Abciximab; ReoPro; Pegvisomant; Somavert; Crotalidae polyvalent immune Fab (ovine); Crofab; Digoxin immune serum Fab (ovine); Digifab; Ranibizumab; Lucentis; Denileukin; Diftitox; Ontak; Ibritumomab; Tiuxetan; Zevalin; Gemtuzumab; Ozogamicin; Mylotarg; Tositumomab and I-tositumomab; Bexxar; Bexxar I-131; Hepatitis B surface antigen (HBsAg); Engerix; Recombivax HB; HPV vaccine; Gardasil; OspA; LYMErix; Anti-Rhesus (Rh) immunoglobulin G; Rhophylac; Recombinant purified protein derivative (DPPD); Glucagon; GlucaGen; Growth hormone releasing hormone (GHRH); Geref; Secretin; ChiRhoStim (human peptide), SecreFlo (porcine peptide); Thyroid stimulating hormone (TSH); thyrotropin; Capromab pendetide; ProstaScint; Indium-111-octreotide; OctreoScan; Satumomab pendetide; OncoScint; Arcitumomab; CEA-scan; Nofetumomab; Verluma; Apcitide; Acutect; Imciromab pentetate; Myoscint; Technetium fanolesomab; NeutroSpec; HIV antigens; Enzyme immunoassay; OraQuick; Uni-Gold; Hepatitis C antigens; or Recombinant immunoblot assay (RI BA).

In some embodiments of the composition, wherein the biological molecule is lysozyme, adlimumab (Humira®), ubiquitin or Factor IX.

In some embodiments of the composition, further comprising a buffer.

In some embodiments of the composition, wherein the composition is acidic.

In some embodiments of the composition, having a pH less than 6.8.

In some embodiments of the composition, having a pH less than 4.

In some embodiments of the composition, having a pH around 3.

In some embodiments of the composition, having a pH between 5 and 7.

In some embodiments of the composition, wherein the composition is basic.

In some embodiments of the composition, having a pH more than 7.2.

In some embodiments of the composition, having a pH more than 10.

In some embodiments of the composition, having a pH around 12.

In some embodiments of the composition, having a pH between 7 and 8.

In some embodiments of the composition, having a pH less than 12.

In some embodiments of the composition, having a pH greater than 3.

In some embodiments of the composition, having a pH greater than 3 and less than 12.

In some embodiments of the composition, wherein the composition is freeze dried, lyophilized, a solution, a liquid, a solid or a suspension.

In some embodiments of the composition, wherein the compound is present at a concentration between 0.1 mM to about 5 M.

In some embodiments of the composition, wherein the compound is present at a concentration between about 0.01 M to about 1M.

The present invention also provides a composition comprising any compound of the present invention.

The present invention also provides a pharmaceutical composition comprising the compound of the present invention.

The present invention also provides a pharmaceutical composition comprising the compound of the present invention and at least one pharmaceutically acceptable carrier.

The present invention also provides a method of stabilizing a biological molecule comprising treating the biological molecule with an effective amount of the compound of the present invention, so as to thereby stabilize the biological molecule.

In some embodiments, the method wherein the biological molecule is a protein, nucleotide, polypeptide or antibody.

In some embodiments, the method wherein the biological molecule has therapeutic activity.

In some embodiments, the method wherein the biological molecule is a biopharmaceutical.

In some embodiments, the method wherein the biological molecule is Insulin; Humulin; Novolin; Insulin human inhalation; Exubera; Insulin aspart; Novolog (aspart); Insulin glulisine; Apidra (glulisine); Insulin lispro; Humalog (lispro); Isophane insulin; NPH; Insulin detemir; Levemir (detemir); Insulin glargine; Lantus (glargine); Insulin zinc extended; Lente; Ultralente; Pramlintide acetate; Symlin; Growth hormone (GH); somatotropin; genotropin; humatrope; norditropin; NorlVitropin; Nutropin; Omnitrope; Protropin; Siazen; Serostim; Valtropin; Mecasermin; Increlex; Mecasermin rinfabate; IPlex; Factor VIII; Bioclate; Helixate; Kogenate; Recominate; ReFacto; Factor IX; Benefix; Antithromin III (AT-III); Thrombate III; Protein C concentrate; Ceprotin; β-Glucocerebrosidase; Cerezyme; β-Glucocerebrosidase; Ceredase (purified from pooled human placenta); Alglucosidase-α; Myozyme; Laronidase (α-1-iduronidase); Aldurazyme; Idursulphase (Iduronate-2-sulphatase); Elaprase; Galsulphase; Naglazyme; Agalsidase-3 (human α-galactosidase A); Fabrazyme; α-1-Proteinase inhibitor; Aralast; Prolastin; Lactase; Lactaid; Pancreatic enzymes (lipase, amylase, protease); Arco-Lase, Cotazym, Creon, Donnazyme, Pancrease, Viokase, Zymase, Adenosine deaminase (pegademase bovine, PEG-ADA); Adagen; Pooled immunoglobulins; Octagam; Human albumin; Albumarc; Albumin; Albuminar; AlbuRx; Albutein; Flexbumin; Buminate; Plasbumin; Erythropoietin; Epoetin-α; Epogen; Procrit; Darbepoetin-α; Aranesp; Filgrastim (granulocyte colony stimulating factor; G-CSF); Neupogen; Pegfilgrastim (Peg-G-CSF); Neulasta; Sargramostim (granulocytemacrophage colony stimulating factor; GM-CSF); Leukine; Oprelvekin (interleukinll; IL11); Neumega; Human follicle-stimulating hormone (FSH); Gonal-F; Follistim; Human chorionic gonadotropin (HCG); Ovidrel; Luveris; Type I alpha-interferon; interferon alfacon 1; consensus interferon; Infergen; Interferon-α2a (IFNα2a); Roferon-A; PegInterferon-α2a; Pegasys; Interferon-α2b (IFNα2b); Intron A; PegInterferon-α2b; Peg-Intron; Interferon-αn3 (IFNαn3); Alferon N; Interferon-β1a (rIFN-β); Avonex; Rebif; Interferon-β1b (rIFN-β); Betaseron; Interferon-γ1b (IFNγ); Actimmune; Aldesleukin (interleukin 2 (TL2); epidermal thymocyte activating factor; ETAF); Proleukin; Alteplase (tissue plasminogen activator; tPA); Activase; Reteplase (deletion mutein of tPA); Retavase; Tenecteplase; TNKase; Urokinase; Abbokinase; Factor VIIa; NovoSeven; Drotrecogin-α (activated protein C); Xigris; Salmon calcitonin; Fortical; Miacalcin; Teriparatide (human parathyroid hormone residues 1-34); Forteo; Exenatide; Byetta; Octreotide; Sandostatin; Dibotermin-α (recombinant human bone morphogenic protein 2; rhBMP2); Infuse; Recombinant human bone morphogenic protein 7 (rhBMP7); Osteogenic protein 1; Histrelin acetate (gonadotropin releasing hormone; GnRH); Supprelin LA; Vantas; Palifermin (keratinocyte growth factor KGF); kepivance; Becaplermin (platelet-derived growth factor; PDGF); Regranex; Trypsin; Granulex; Nesiritide; Natrecor; Botulinum toxin type A; Botox; Botulinum toxin type B; Myoblock; Collagenase; Santyl; Human deoxy-ribonuclease I; dornase-α; pulmozyme; Hyaluronidase (bovine, ovine); Amphadase (bovine); hydase (bovine); Vitrase (ovine); Hyaluronidase (recombinant human); hylenex; Papain; accuzyme; panafil; L-asparaginase; ELSPAR; Peg-asparaginase; Oncaspar; Rasuricase; Elitek; Lepirudin; Refludan; Bivalirudin; Angiomax; Streptokinase; Streptase; Anistreplase (anisoylated plasminogen streptokinase activator complex; APSAC); Eminase; Bevacizumab; Avastin; Cetuximab; Erbitux; Panitumumab; Vectibix; Alemtuzumab; Campath; Rituximab; Rituxan; Trastuzumab; Herceptin; Abatacept; Orencia; Anakinra; Antril; Kineret; Abalimumab; Humira; Etanercept; Enbrel; Infliximab; Remicade; Alefacept; Amevive; Natalizumab; Tysabri; Eculizumab; Soliris; Antithymocyte globulin (rabbit); Thymoglobulin; Basiliximab; Simulect; Daclizumab; Zenapax; Muromonab-CD3; Orthoclone; OKT3; Omalizumab; Xolair; Palivizumab; Synagis; Enfuvirtide; Fuzeon; Abciximab; ReoPro; Pegvisomant; Somavert; Crotalidae polyvalent immune Fab (ovine); Crofab; Digoxin immune serum Fab (ovine); Digifab; Ranibizumab; Lucentis; Denileukin; Diftitox; Ontak; Ibritumomab; Tiuxetan; Zevalin; Gemtuzumab; Ozogamicin; Mylotarg; Tositumomab and I-tositumomab; Bexxar; Bexxar I-131; Hepatitis B surface antigen (HBsAg); Engerix; Recombivax HB; HPV vaccine; Gardasil; OspA; LYMErix; Anti-Rhesus (Rh) immunoglobulin G; Rhophylac; Recombinant purified protein derivative (DPPD); Glucagon; GlucaGen; Growth hormone releasing hormone (GHRH); Geref; Secretin; ChiRhoStim (human peptide), SecreFlo (porcine peptide); Thyroid stimulating hormone (TSH); thyrotropin; Capromab pendetide; ProstaScint; Indium-111-octreotide; OctreoScan; Satumomab pendetide; OncoScint; Arcitumomab; CEA-scan; Nofetumomab; Verluma; Apcitide; Acutect; Imciromab pentetate; Myoscint; Technetium fanolesomab; NeutroSpec; HIV antigens; Enzyme immunoassay; OraQuick; Uni-Gold; Hepatitis C antigens; or Recombinant immunoblot assay (RI BA).

In some embodiments, the method wherein the biological molecule is lysozyme, adlimumab (Humira®), ubiquitin or Factor IX.

In some embodiments, the method wherein the biological molecule is stabilized in the presence of pH stress.

In some embodiments, the method wherein the pH stress is an acidic environment.

In some embodiments, the method wherein the acidic environment has a pH less than 6.8. In some embodiments, the method wherein the acidic environment has a pH less than 4. In some embodiments, the method wherein the acidic environment has a pH around 3. In some embodiments, the method wherein the acidic environment has a pH between 5 and 7.

In some embodiments, the method wherein the pH stress is a basic environment.

In some embodiments, the method wherein the basic environment has a more than 7.2. In some embodiments, the method wherein the basic environment has a pH more than 10. In some embodiments, the method wherein the basic environment has a pH around 12.

In some embodiments, the method wherein the biological molecule is treated with the compound prior to being subjected to pH stress.

In some embodiments, the method wherein the biological molecule is stabilized in the presence of thermal stress.

In some embodiments, the method wherein the thermal stress is freeze drying, lyophilization or heating of the biological molecule.

In some embodiments, the method wherein the thermal stress is heating about the glass transition state or melting point of the biological molecule.

In some embodiments, the method wherein the biological molecule is treated with the compound prior to being subjected to thermal stress.

In some embodiments, the method wherein the biological molecule is treated with the compound at a concentration between 0.1 mM to about 5 M.

In some embodiments, the method wherein the biological molecule is treated with the compound at a concentration between 0.1 M to about 1 M.

In some embodiments, any compound of the present inventions or mixture thereof for use in any method of the present invention.

In some embodiments, a composition or pharmaceutical composition comprising any compound of the present inventions or mixture thereof.

The compounds of the present invention include neutral glycosylated amides (neutral amide-type) and dianionic glucuronidated acids (dionic uronic acid-type). Preferably, the neutral amide-type stabilizers contain only non-ionizable functional groups, e.g., amide and hydroxyl functional groups whereas the dianionic uronic acid-type stabilizers contain two ionizable carboxylic acid functional groups, one which is at C-6 of the hexose moiety and one which is linked to the hexose via the glycosidic bond. The dianionic uronic acid-type stabilizers of the present invention includes stabilizers, containing two ionizable acid groups, which are in their neutral form as well as the salts derived from their monoanionic and dianionic forms, e.g., as monosodium salt, disodium salt, monopotassium salt, dipotassium salt, calcium salt, magnesium salt, etc. In specific embodiments, the compound is a dipotassium salt.

The compounds of the present invention include all hydrates, solvates, and complexes of the compounds used by this invention. If a chiral center or another form of an isomeric center is present in a compound of the present invention, all forms of such isomer or isomers, including enantiomers and diastereomers, are intended to be covered herein. Compounds containing a chiral center may be used as a racemic mixture, an enantiomerically enriched mixture, or the racemic mixture may be separated using well-known techniques and an individual enantiomer may be used alone. The enantiomers can be separated using known techniques, such as those described in Pure and Applied Chemistry 69, 1469-1474, (1997) IUPAC.

Except where otherwise specified, if the structure of a compound of this invention includes an asymmetric carbon atom, it is understood that the compound occurs as a racemate, racemic mixture, and isolated single enantiomer. All such isomeric forms of these compounds are expressly included in this invention. Except where otherwise specified, each stereogenic carbon may be of the R or S configuration. It is to be understood accordingly that the isomers arising from such asymmetry (e.g., all enantiomers and diastereomers) are included within the scope of this invention, unless indicated otherwise. Such isomers can be obtained in substantially pure form by classical separation techniques and by stereochemically controlled synthesis, such as those described in "Enantiomers, Racemates and Resolutions" by J. Jacques, A. Collet and S. Wilen, Pub. John Wiley & Sons, N Y, 1981. For example, the resolution may be carried out by preparative chromatography on a chiral column.

The compounds of the subject invention may have spontaneous tautomeric forms. In cases wherein compounds may exist in tautomeric forms, such as keto-enol tautomers, each tautomeric form is contemplated as being included within this invention whether existing in equilibrium or predominantly in one form.

In the compound structures depicted herein, hydrogen atoms are not shown for carbon atoms having less than four bonds to non-hydrogen atoms. However, it is understood that enough hydrogen atoms exist on said carbon atoms to satisfy the octet rule.

It is understood that where a numerical range is recited herein, the present invention contemplates each integer between, and including, the upper and lower limits, unless otherwise stated.

This invention also provides isotopic variants of the compounds disclosed herein. Accordingly, in the compounds provided herein hydrogen can be enriched in the deuterium isotope. It will be noted that any notation of a carbon in structures throughout this application, when used without further notation, are intended to represent all isotopes of carbon, such as $^{12}C$, $^{13}C$, or $^{14}C$. Furthermore, any compounds containing $^{13}C$ or $^{11}C$ may specifically have the structure of any of the compounds disclosed herein. It will also be noted that any notation of a hydrogen in structures throughout this application, when used without further notation, are intended to represent all isotopes of hydrogen, such as $^{1}H$, $^{2}H$, or $^{3}H$. Furthermore, any compounds containing $^{2}H$ or $^{3}H$ may specifically have the structure of any of the compounds disclosed herein. Isotopically-labeled compounds can generally be prepared by conventional techniques known to those skilled in the art using appropriate isotopically-labeled reagents in place of the non-labeled reagents employed. It is to be understood that the invention encompasses all such isotopic forms.

It is understood that substituents and substitution patterns on the compounds used in the method of the present invention can be selected by one of ordinary skill in the art to provide compounds that are chemically stable and that can be readily synthesized by techniques known in the art from readily available starting materials. If a substituent is itself substituted with more than one group, it is understood that these multiple groups may be on the same carbon or on different carbons, so long as a stable structure results.

As used herein, "alkyl" is intended to include both branched, straight-chain and cycloalkyl saturated aliphatic hydrocarbon groups having the specified number of carbon atoms. Thus, alkyl specifically includes methyl, ethyl, propyl, cyclopropyl, isopropyl, butyl, pentyl, hexyl, heptyl, isopropyl, isobutyl, sec-butyl and so on. An embodiment can be $C_1$-$C_{12}$ alkyl, $C_1$-$C_3$ alkyl, $C_2$-$C_{12}$ alkyl, $C_3$-$C_{12}$ alkyl, $C_4$-$C_{12}$ alkyl and so on. Neighboring alkyl substituents may be linked so as to form a saturated carbocyclic ring. As herein, "cycloalkyl" shall mean cyclic rings of alkanes of three to eight total carbon atoms, or any number within this range (i.e., cyclopropyl, cyclobutyl, cyclopentyl, cyclohexyl, cycloheptyl or cyclooctyl). Alkyl may be optionally substituted. For example, alkyl may be optionally substituted by oxygen, nitrogen or sulfur atoms. As another example, alkyl may be optionally substituted by a phenyl, an alcohol, a halogen (i.e., F, Cl, Br, and I), an alkoxy group such as methoxy, ethoxy, n-propoxy and isopropoxy, an alkylthio group such as methylthio and ethylthio, a carboxylate or an acetate group.

A "O-alkyl" group means an (oxygen)-R radical where R is alkyl as defined above. For example, O-alkyl may be an oxygen atom bonded to a C1 to C6 straight chain or branched chain alkyl.

A "hexosyl" group is a hexose radical. Hexosyl groups may be, but are not limited to, glucosyl, mannosyl and galactosyl. Other Hexosyl groups include allosyl, altrosyl, gulosyl, idosyl and talosyl. Hexosyl includes unoxidized hexosyl groups but also may include oxidized hexosyl groups such as uronic acid groups. Uronic acid groups are a uronic acid radical which may be, but are not limited to, glucuronsyl, mannuronsyl and galacturonsyl. The hexose or oxidized hexose groups may be a D or L stereoisomer. The hexosyl group may be an alpha- or beta-anomer. The hexosyl group is linked to the parent substrate via an oxygen to C-1, C-2, C-3, C-4 or C-6. The hexosyl group may be an alpha- or beta-anomer.

A "glucosyl" group is a radical of a glucose molecule. The glucose molecule may be D or L mannose. A glucosyl group is linked to the parent substrate via an oxygen to C-1, C-2, C-3, C-4 or C-6. The glucosyl group may be an alpha- or beta-anomer. Unless otherwise specified, a glucosyl group is linked at the oxygen off of the anomeric C-1. For example, glucosyl may be defined as:

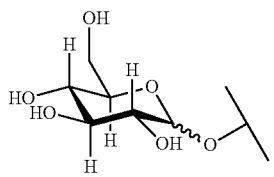

A "galactosyl" group is a radical of a galactose molecule. The galactose molecule may be D or L mannose. A galactosyl group is linked to the parent substrate via an oxygen to C-1, C-2, C-3, C-4 or C-6. The galactosyl group may be an alpha- or beta-anomer. Unless otherwise specified, a galactosyl group is linked at the oxygen off of the anomeric C-1. For example, galactosyl may be defined as:

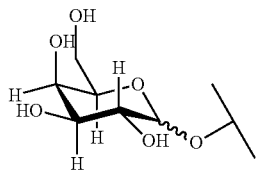

A "mannosyl" group is a radical of a mannose molecule. The mannose molecule may be D or L mannose. A mannosyl group is linked to the parent substrate via an oxygen to C-1, C-2, C-3, C-4 or C-6. The mannosyl group may be an alpha- or beta-anomer. Unless otherwise specified, a mannosyl group is linked at the oxygen off of the anomeric C-1. For example, mannosyl may be defined as:

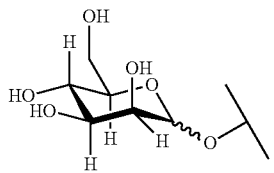

A "glucuronosyl" or "glucuronic acid group" is a radical of a glucuronic acid molecule. The glucuronic acid group may be D or L glucuronic acid.

A glucuronic acid group is linked to the parent substrate via an oxygen to C-1, C-2, C-3, C-4 or C-6. The glucuronic acid group may be an alpha- or beta-anomer. Unless otherwise specified, a glucuronic acid group is linked at the oxygen off of the anomeric C-1. For example, glucuronic acid group may be defined as:

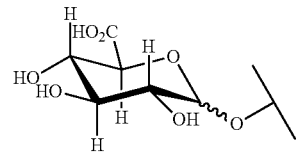

A "galacturonosyl" or "galacturonic acid group" is a radical of a galacturonic acid molecule. The galacturonic acid group may be D or L galacturonic acid. A galacturonic acid group is linked to the parent substrate via an oxygen to C-1, C-2, C-3, C-4 or C-6. The galacturonic acid group may be an alpha- or beta-anomer. Unless otherwise specified, a galacturonic acid group is linked at the oxygen off of the anomeric C-1. For example, galacturonic acid group may be defined as:

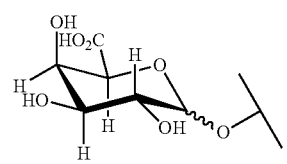

A "mannuronosyl" or "mannuronic acid group" is a radical of a mannuronic acid molecule. The mannuronic acid group may be D or L mannuronic acid. A mannuronic acid group is linked to the parent substrate via an oxygen to C-1, C-2, C-3, C-4 or C-6. The mannuronic acid group may be an alpha- or beta-anomer. Unless otherwise specified, a mannuronic acid group is linked at the oxygen off of the anomeric C-1. For example, mannuronic acid group may be defined as:

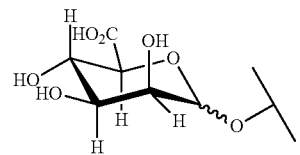

As used herein, the term "halogen" refers to F, Cl, Br, and I.

An "optionally substituted" group refers to a functional group in which one or more bonds to a hydrogen atom contained therein are replaced by a bond to non-hydrogen or non-carbon atoms, provided that normal valencies are maintained and that the substitution results in a stable compound. Substituted groups also include groups in which one or more bonds to a carbon(s) or hydrogen(s) atom are replaced by one or more bonds, including double or triple bonds, to a heteroatom. Examples of substituent groups include halogens (i.e., F, Cl, Br, and I); alkyl groups, such as methyl, ethyl, n-propyl, isopropryl, n-butyl, tert-butyl, and trifluoromethyl; hydroxyl; alkoxy groups, such as methoxy, ethoxy, n-propoxy, and isopropoxy; aryloxy groups, such as phenoxy; arylalkyloxy, such as benzyloxy (phenylmethoxy) and p-trifluoromethylbenzyloxy (4-trifluoromethylphenylmethoxy); heteroaryloxy groups; sulfonyl groups, such as trifluoromethanesulfonyl, methanesulfonyl, and p-toluenesulfonyl; nitro, nitrosyl; mercapto; sulfanyl groups, such as methylsulfanyl, ethylsulfanyl and propylsulfanyl; cyano; amino groups, such as amino, methylamino, dimethylamino, ethylamino, and diethylamino; and carboxyl. Where multiple substituent moieties are disclosed or claimed, the substituted compound can be independently substituted by one or more of the disclosed or claimed substituent moieties, singly or pluraly. By independently substituted, it is meant that the (two or more) substituents can be the same or different.

The compounds of the present invention also include any of the compounds disclosed herein modified by common protecting groups. For example, the compounds of the present invention include glycosylated amides as described herein but modified where the amide is protected by an amide protecting group, e.g., BOC, and the hydroxyl groups are protected by a hydroxyl protecting group, e.g., benzyl. As another example, the compounds of the present invention include glucuronidated acids where the carboxylic acid moiety is protected as an ester. Common protecting groups are known to a person of ordinary skill in the art as set forth in Greene's Protective Groups in Organic Synthesis (Wuts (2006)).

In choosing the compounds of the present invention, one of ordinary skill in the art will recognize that the various substituents are to be chosen in conformity with well-known principles of chemical structure connectivity.

The compounds used in the method of the present invention may be in a salt form. As used herein, a "salt" is a salt of the instant compounds which has been modified by making acid or base salts of the compounds. In the case of compounds used to stabilize a therapeutic biological molecule, the salt may be a pharmaceutically acceptable salt. Examples of pharmaceutically acceptable salts include, but are not limited to, mineral or organic acid salts of basic residues such as amines; alkali or organic salts of acidic residues such as carboxylic acids. The salts can be made using an organic or inorganic acid. Such salts include, but are not limited to, alkali metals and alkaline earth metal salts such as lithium sodium, potassium, beryllium, magnesium and calcium salts. Salts also include alkyl ammonium salts, ammonium salts and salts derived from amino acids. The term "pharmaceutically acceptable salt" in this respect, refers to the relatively non-toxic, inorganic and organic acid or base addition salts of compounds of the present invention. These salts can be prepared in situ during the final isolation and purification of the compounds of the invention, or by separately reacting a purified compound of the invention in its free base or free acid form with a suitable organic or inorganic acid or base, and isolating the salt thus formed. (See, e.g., Berge et al. (1977) "Pharmaceutical Salts", *J. Pharm. Sci.* 66:1-19).

The compounds of the present invention may be used in a pharmaceutical composition comprising a therapeutic biological molecule in admixture with suitable pharmaceutical diluents, extenders, excipients or carriers.

A "biological molecule" is a protein, nucleotide, polypeptide, antibody including monoclonal antibody, enzyme, or a fragment or mixture of any of the preceding. A biological molecule may also be a fragment of a cell, virus, liposome or tissue. In alternative embodiments, the biological molecule has therapeutic activity or it has no therapeutic activity.

In embodiments of the subject invention, the therapeutic biological molecule may be one of: Insulin; Humulin; Novolin; Insulin human inhalation; Exubera; Insulin aspart; Novolog (aspart); Insulin glulisine; Apidra (glulisine); Insulin lispro; Humalog (lispro); Isophane insulin; NPH; Insulin detemir; Levemir (detemir); Insulin glargine; Lantus (glargine); Insulin zinc extended; Lente; Ultralente; Pramlintide acetate; Symlin; Growth hormone (GH); somatotropin; genotropin; humatrope; norditropin; NorIVitropin; Nutropin; Omnitrope; Protropin; Siazen; Serostim; Valtropin; Mecasermin; Increlex; Mecasermin rinfabate; IPlex; Factor VIII; Bioclate; Helixate; Kogenate; Recominate; ReFacto; Factor IX; Benefix; Antithromin III (AT-III); Thrombate III; Protein C concentrate; Ceprotin; β-Glucocerebrosidase; Cerezyme; β-Glucocerebrosidase; Ceredase (purified from pooled human placenta); Alglucosidase-α; Myozyme; Laronidase (α-1-iduronidase); Aldurazyme; Idursulphase (Iduronate-2-sulphatase); Elaprase; Galsulphase; Naglazyme; Agalsidase-β (human α-galactosidase A); Fabrazyme; α-1-Proteinase inhibitor; Aralast; Prolastin; Lactase; Lactaid; Pancreatic enzymes (lipase, amylase, protease); Arco-Lase, Cotazym, Creon, Donnazyme, Pancrease, Viokase, Zymase, Adenosine deaminase (pegademase bovine, PEG-ADA); Adagen; Pooled immunoglobulins; Octagam; Human albumin; Albumarc; Albumin; Albuminar; AlbuRx; Albutein; Flexbumin; Buminate; Plasbumin; Erythropoietin; Epoetin-α; Epogen; Procrit; Darbepoetin-α; Aranesp; Filgrastim (granulocyte colony stimulating factor; G-CSF); Neupogen; Pegfilgrastim (Peg-G-CSF); Neulasta; Sargramostim (granulocytemacrophage colony stimulating factor; GM-CSF); Leukine; Oprelvekin (interleukinll; IL11); Neumega; Human follicle-stimulating hormone (FSH); Gonal-F; Follistim; Human chorionic gonadotropin (HCG); Ovidrel; Luveris; Type I alpha-interferon; interferon alfacon 1; consensus interferon; Infergen; Interferon-α2a (IFNα2a); Roferon-A; PegInterferon-α2a; Pegasys; Interferon-α2b (IFNα2b); Intron A; PegInterferon-α2b; Peg-Intron; Interferon-αn3 (IFNαn3); Alferon N; Interferon-β1a (rIFN-β); Avonex; Rebif; Interferon-β1b (rIFN-β); Betaseron; Interferon-γ1b (IFNγ); Actimmune; Aldesleukin (interleukin 2 (IL2); epidermal thymocyte activating factor; ETAF); Proleukin; Alteplase (tissue plasminogen activator; tPA); Activase; Reteplase (deletion mutein of tPA); Retavase; Tenecteplase; TNKase; Urokinase; Abbokinase; Factor VIIa; NovoSeven; Drotrecogin-α (activated protein C); Xigris; Salmon calcitonin; Fortical; Miacalcin; Teriparatide (human parathyroid hormone residues 1-34) Forteo; Exenatide; Byetta; Octreotide; Sandostatin; Dibotermin-α (recombinant human bone morphogenic protein 2; rhBMP2); Infuse; Recombinant human bone morphogenic protein 7 (rhBMP7); Osteogenic protein 1; Histrelin acetate (gonadotropin releasing hormone; GnRH); Supprelin LA; Vantas; Palifermin (keratinocyte growth factor KGF); kepivance; Becaplermin (platelet-derived growth factor; PDGF); Regranex; Trypsin; Granulex; Nesiritide; Natrecor; Botulinum toxin type A; Botox; Botulinum toxin type B; Myoblock; Collagenase; Santyl; Human deoxy-ribonuclease I; dornase-α; pulmozyme; Hyaluronidase (bovine, ovine); Amphadase (bovine); hydase (bovine); Vitrase (ovine); Hyaluronidase (recombinant human); hylenex; Papain; accuzyme; panafil; L-asparaginase; ELSPAR; Peg-asparaginase; Oncaspar; Rasburicase; Elitek; Lepirudin; Refludan; Bivalirudin; Angiomax; Streptokinase; Streptase; Anistreplase (anisoylated plasminogen streptokinase activator complex; APSAC); Eminase; Bevacizumab; Avastin; Cetuximab; Erbitux; Panitumumab; Vectibix; Alemtuzumab; Campath; Rituximab; Rituxan; Trastuzumab; Herceptin; Abatacept; Orencia; Anakinra; Antril; Kineret; Abalimumab; Humira; Etanercept; Enbrel; Infliximab; Remicade; Alefacept; Amevive; Natalizumab; Tysabri; Eculizumab; Soliris; Antithymocyte globulin (rabbit); Thymoglobulin; Basiliximab; Simulect; Daclizumab; Zenapax; Muromonab-CD3; Orthoclone; OKT3; Omalizumab; Xolair; Palivizumab; Synagis; Enfuvirtide; Fuzeon; Abciximab; ReoPro;

Pegvisomant; Somavert; Crotalidae polyvalent immune Fab (ovine); Crofab; Digoxin immune serum Fab (ovine); Digifab; Ranibizumab; Lucentis; Denileukin; Diftitox; Ontak; Ibritumomab; Tiuxetan; Zevalin; Gemtuzumab; Ozogamicin; Mylotarg; Tositumomab and I-tositumomab; Bexxar; Bexxar I-131; Hepatitis B surface antigen (HBsAg); Engerix; Recombivax HB; HPV vaccine; Gardasil; OspA; LYMErix; Anti-Rhesus (Rh) immunoglobulin G; Rhophylac; Recombinant purified protein derivative (DPPD); Glucagon; GlucaGen; Growth hormone releasing hormone (GHRH); Geref; Secretin; ChiRhoStim (human peptide), SecreFlo (porcine peptide); Thyroid stimulating hormone (TSH); thyrotropin; Capromab pendetide; ProstaScint; Indium-111-octreotide; OctreoScan; Satumomab pendetide; OncoScint; Arcitumomab; CEA-scan; Nofetumomab; Verluma; Apcitide; Acutect; Imciromab pentetate; Myoscint; Technetium fanolesomab; NeutroSpec; HIV antigens; Enzyme immunoassay; OraQuick; Uni-Gold; Hepatitis C antigens; oRecombinant immunoblot assay (RI BA).

As used herein, "degradation" of a biological molecule includes, but is not limited to, aggregation, denaturation, misfolding and precipitation of the biological molecule. The degradation may be induced by physical stress or it may be induced by chemical stress. Physical stress includes high temperature, low temperature, heating above the thermal unfolding temperature, freezing, agitation, shaking, surfaces and pressure. Chemical stress includes low pH, high pH, pH divergent from the ideal pH environment of the natively-folded protein (e.g., divergent by a pH of 1, 2, 3, 4 or 5), dehydration, organic solvents and the presence of impurities such as detergents or chaeotropic agents.

A stabilized biological molecule retains its native structure and activity for longer period of time or across a broader range of conditions than an unstabilized biological molecule. Additionally or alternatively, a stabilized biological molecule does not degrade under conditions which degrade an unstabilized form of the same biological molecule. A stabilized biological molecule has a higher melting temperature than an unstabilized biological molecule.

Techniques and compositions for making such compositions are described in the following references: 7 Modern Pharmaceutics, Chapters 9 and 10 (Banker & Rhodes, Editors, 1979); Pharmaceutical Dosage Forms: Tablets (Lieberman et al., 1981); Ansel, Introduction to Pharmaceutical Dosage Forms 2nd Edition (1976); Remington's Pharmaceutical Sciences, 17th ed. (Mack Publishing Company, Easton, Pa., 1985); Advances in Pharmaceutical Sciences (David Ganderton, Trevor Jones, Eds., 1992); Advances in Pharmaceutical Sciences Vol. 7. (David Ganderton, Trevor Jones, James McGinity, Eds., 1995); Aqueous Polymeric Coatings for Pharmaceutical Dosage Forms (Drugs and the Pharmaceutical Sciences, Series 36 (James McGinity, Ed., 1989); Pharmaceutical Particulate Carriers: Therapeutic Applications: Drugs and the Pharmaceutical Sciences, Vol 61 (Alain Rolland, Ed., 1993); Drug Delivery to the Gastrointestinal Tract (Ellis Horwood Books in the Biological Sciences. Series in Pharmaceutical Technology; J. G. Hardy, S. S. Davis, Clive G. Wilson, Eds.); Modem Pharmaceutics Drugs and the Pharmaceutical Sciences, Vol 40 (Gilbert S. Banker, Christopher T. Rhodes, Eds.). All of the aforementioned publications are incorporated by reference herein.

The present invention also includes embodiments where a glucosyl, mannosyl, or galactosyl group is replaced with allosyl, altrosyl, gulosyl, idosyl or talosyl, or any of the corresponding uronic acids.

Each embodiment disclosed herein is contemplated as being applicable to each of the other disclosed embodiments. Thus, all combinations of the various elements described herein are within the scope of the invention.

This invention will be better understood by reference to the Experimental Details which follow, but those skilled in the art will readily appreciate that the specific experiments detailed are only illustrative of the invention as described more fully in the claims which follow thereafter.

Compound Name Abbreviations

Abbreviations for the compounds of the present invention are as follows:
MglyA—mannosyl-glycolamide
MLA—mannosyl-lactamide
GBA—3-glucosyl-butanamide
GaBA—3-galactosyl-butanamide
GGlyA—glucosyl-glycolamide
GaGlyA—galactosyl-glycolamide
GLA—glucosyl-lactamide
GaLA—galactosyl-lactamide
b-GGlyA—beta-glucosyl-glycolamide
b-GLA—beta-glucosyl-lactamide
b-GaGlyA—beta-galactosyl-glycolamide
b-GBA—beta-3-glucosyl-butanamide
a-MglyA—alpha-mannosyl-glycolamide
a-MLA—alpha-mannosyl-lactamide
b-GGly—beta-glucosyl-glycolate
b-GL—beta-glucosyl-lactate
b-GB—beta-3-glucosyl-butyrate
b-GaGly—beta-galactosyl-glicolate
b-GaL—beta-galactosyl-lactate Synthesis of the Compounds In general, compounds of the present invention may be prepared using a number of methods known in the chemical arts, particularly in light of the description contained herein, in combination with the knowledge of the skilled artisan. Various starting materials, intermediates, and reagents may be purchased from commercial sources or made according to literature methods or adaptations thereof. Although other reagents, compounds or methods can be used in practice or testing, generalized methods for the preparation of the compounds of the present invention are illustrated by the following descriptions and reaction Schemes. The methods disclosed herein, including those outlined in the Schemes, descriptions, and Examples are for intended for illustrative purposes and are not to be construed in any manner as limitations thereon. Various changes and modifications will be obvious to those of skill in the art given the benefit of the present disclosure and are deemed to be within the spirit and scope of the present disclosure as further defined in the appended claims.

Although specific embodiments of various aspects of the invention will be described with reference to the Schemes, Preparations and/or Examples, it should be understood that such embodiments are by way of example only and are merely illustrative of a small number of the many possible specific embodiments which can represent applications of the principles of the present disclosure. The starting materials used for the synthesis of compounds described herein can be obtained from commercial sources, such as Aldrich Chemical Co. (Milwaukee, Wis.), Sigma Chemical Co. (St. Louis, Mo.), or the starting materials can be synthesized. The compounds described herein, and other related compounds having different substituents can be synthesized using techniques and materials known to those of skill in the art, such as described, for example, in March's Advanced Organic Chemistry: Reactions, Mechanisms, and Structure (Smith (2013)), Design and Strategy in Organic Synthesis (Hanessian (2013)) Greene's Protective Groups in Organic Synthesis (Wuts (2006)) and Fiesers' Reagents for Organic Synthesis (Volumes 1-27) (Ho (2013)), each of which are incorporated by reference in their entirety.

General methods for the preparation of the compounds as disclosed herein may be derived from known reactions in the field, and the reactions may be modified by the use of appropriate reagents and conditions, as would be recognized by the skilled person, for the introduction of the various moieties found in the formulae as provided herein. (Trombotto et al. 2000; Matsumura et al. 1997; Krajewski et al. 1997; Faria et al. 2008; Xue et al. 2009; Moynihan et al. 2013; WO 2008/007153 A2; WO 2012/109263 A1; and WO 2015/137838)

The intermediate products described can be recovered by extraction, evaporation, or other techniques known in the art. The crude materials may then be optionally purified by chromatography, HPLC, recrystallization, trituration, distillation, or other techniques known in the art.

As would be appreciated by those skilled in the art, some of the methods useful for the preparation of such compounds, as discussed above, may require protection of a particular functionality, e.g., to prevent interference by such functionality in reactions at other sites within the molecule or to preserve the integrity of such functionality. The need for, and type of, such protection is readily determined by one skilled in the art, and will vary depending on, for example, the nature of the functionality and the conditions of the selected preparation method. Methods of introducing and removing protecting groups are well known to those of ordinary skill in the art and are described in Greene's Protective Groups in Organic Synthesis (Wuts (2006)). Alternate reagents, starting materials, as well as methods for optimizing or adapting the procedures described herein would also be readily determined by one skilled in the art.

Preparation of Neutral Gycosylated Amides

Amides from gluco-, manno- and galactosides were prepared in quantitative yields by reaction with ammonia in methanol. Due to the presence of the amide group and hydroxyl groups, the resulting stabilizers are devoid of charge similar to trehalose and saccharose.

Synthesis of Methyl 2-O-(α-D-mannopyranosyl)acetate (5)

Synthesis of compound 5 was carried out according to the procedure described in literature: *Carbohydrate Research* 343 (2008), 3025-3033.

Synthesis of Methyl (2S)-2-O-(α-D-mannopyranosyl)-3-propanoate (11)

Synthesis of compound 11 was carried out according to the procedure described in literature: *Carbohydrate Research* 343 (2008), 3025-3033.

Scheme 1.

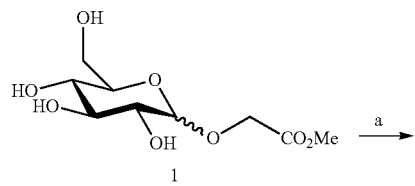
1

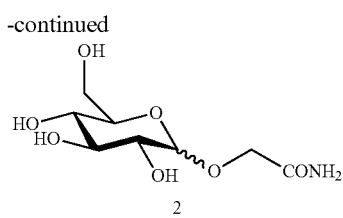
2
GGlyA

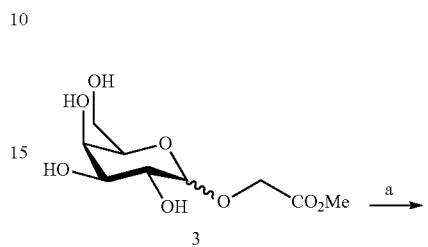
3

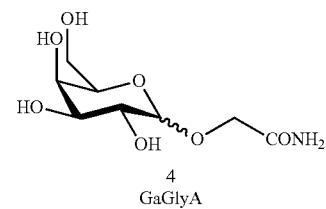
4
GaGlyA

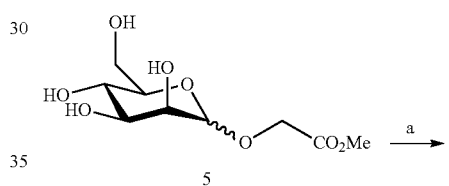
5

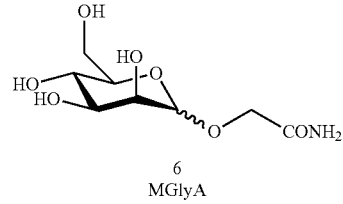
6
MGlyA

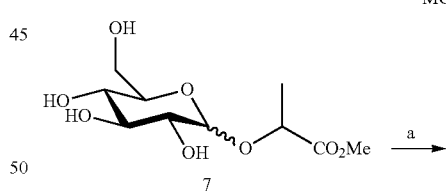
7

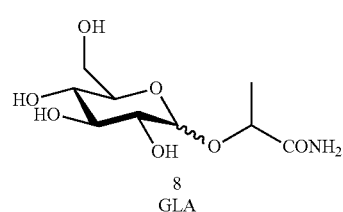
8
GLA

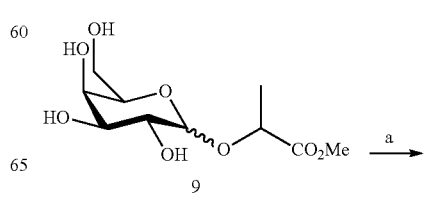
9

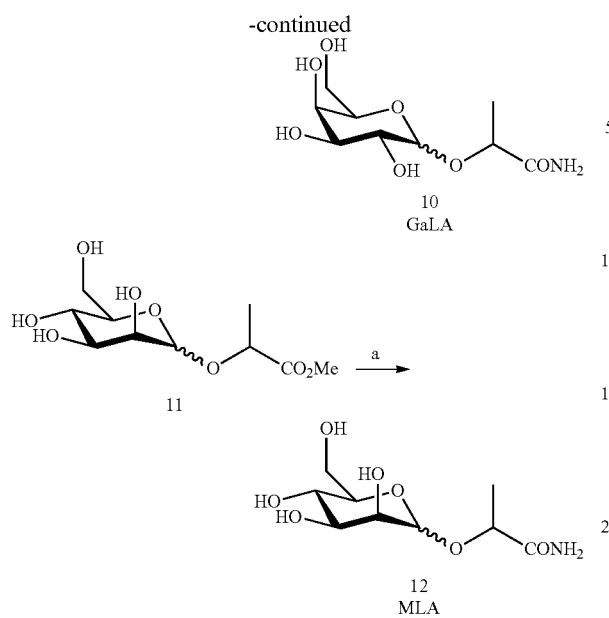

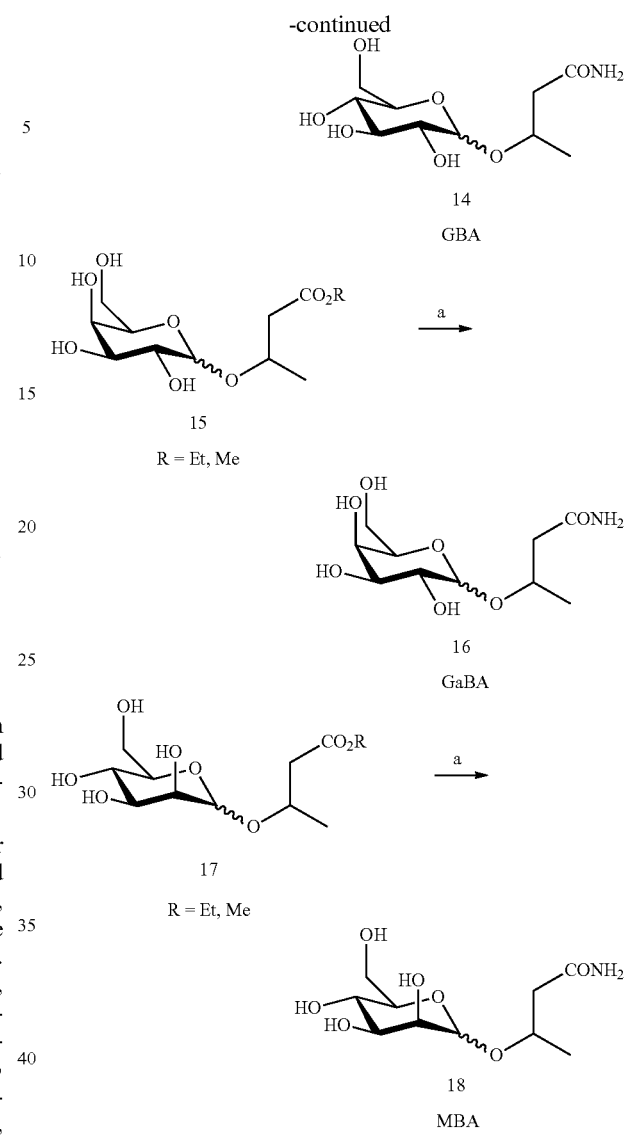

a) NH₃, MeOH, -78° C./rt, ≥99%

Each starting material was treated with ammonium in methanol at -78° C. and warmed to room temperature and produced the desired product via ester amidolysis at quantitative or near-quantitiatve yield (≥99%).

The starting materials (1, 3, 5, 7, 9 and 11) and other related compounds may be synthesized using techniques and materials known to those of skill in the art. Additionally, starting materials in Scheme 1 have been reported in the literature and thus may be accessed as previously described. Compound 1 was reported in Carbohydrate Res. 2009, 344, 1646 (beta-anomer); J. Org. Chem. 2003, 68, 6672; Tetrahedron Lett. 2000, 41, 8273. (alpha-anomer). The beta-anomer of Compound 3 was reported in WO 2008/007153 A2 and WO 2015/137838 A1. The alpha-anomer of Compound 5 was reported in Carbohydrate Res. 2008, 343, 3025, WO 2015/137838 A1 and WO 2012/109283 A1. The starting materials (7, 9 and 11) in Scheme 2 have been prepared in the literature and are thus are available at least by the same methods previously described. Compound 7 was reported in WO 2015/137838 A1 (both configurations). The beta-anomer of Compound 9 was reported in WO 2008/007153 A2. The alpha-anomer of Compound 11 was reported in Carbohydrate Res. 2008, 343, 3025. The beta-anomer of amide 2 (b-GGlyA) was disclosed in Carbohydrate Res. 2013, 374, 29 and its structure was studied but, importantly, no particular function or effect of the compound was disclosed.

Scheme 2.

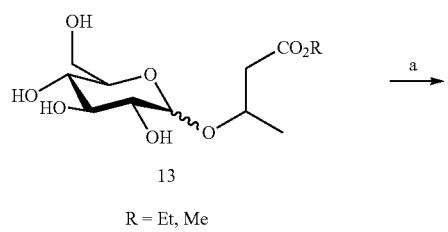

Each starting material, as either ethyl or methyl ester, is treated with ammonium in methanol at -78° C. and warmed to room temperature to produce the desired amide product via ester amidolysis at quantitative or near-quantitiatve yield. Compound 14 was produced in 99% yield from starting material 13.

The starting materials (13, 15 and 17) and other related compounds may be synthesized using techniques and materials known to those of skill in the art. Additionally, starting materials in Scheme 2 have been reported in the literature and thus may be accessed as previously described. Compound 13 (as ethyl ester) was reported in Phytochemistry 1997, 45 and Biotechnol. Lett., 1995, 17, 1169. Compound 15 (as ethyl and methyl esters) was reported in Biotechnol. Lett. 1997, 19, 583. The alpha-anomer of Compound 17 (as ethyl ester) was reported in WO 2015/137838 A1.

Preparation of Dianionic Glucuronidated Acids

Gluco-, galacto- and mannuronic acids (Compounds 37-42) are prepared as described in Scheme 3. Due to the presence of the two carboxylic acid moieties, the resulting stabilizers are ionizable in two positions in contrast to trehaolse and saccharose which are devoid of charge.

Scheme 3.

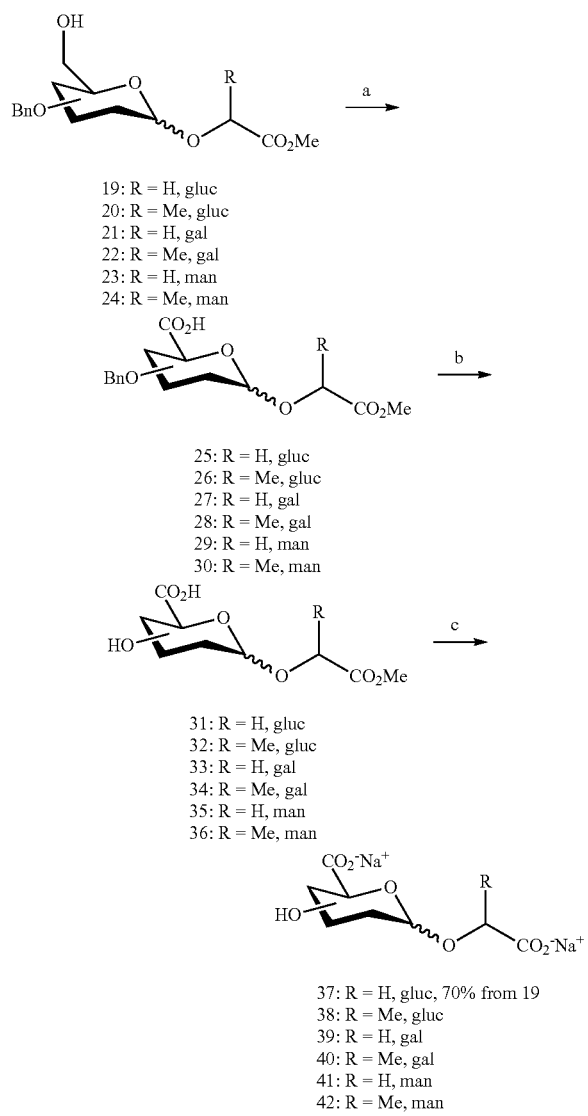

19: R = H, gluc
20: R = Me, gluc
21: R = H, gal
22: R = Me, gal
23: R = H, man
24: R = Me, man 25: R = H, gluc
26: R = Me, gluc
27: R = H, gal
28: R = Me, gal
29: R = H, man
30: R = Me, man 31: R = H, gluc
32: R = Me, gluc
33: R = H, gal
34: R = Me, gal
35: R = H, man
36: R = Me, man 37: R = H, gluc, 70% from 19
38: R = Me, gluc
39: R = H, gal
40: R = Me, gal
41: R = H, man
42: R = Me, man a) BAIB/TEMPO, CH$_2$Cl$_2$/H$_2$O
b) H$_2$, Pd/C, 50 Psi, AcOEt,
c) NaOH, H$_2$O The C-6 primary hydroxyl group is efficiently oxidized to the corresponding carboxylic acid with a BAIB/Tempo reagent combination. The benzyl ether protecting groups is next removed with Pd/C and H$_2$ at 50 psi. Hydrolysis of the methyl ester with NaOH in water affords the sodium salts of the final products in quantitative yields. The final compounds under basic conditions presented two charges, derived from the two carboxylic acid functional groups. The disodium salt 37 was prepared at 70% overall yield from starting material 19. The disodium salt 38 was prepared at 66% overall yield from starting material 20.

The starting materials (19-24) and other related compounds may be synthesized using techniques and materials known to those of skill in the art. Additionally, starting materials in Scheme 2 have been reported in the literature and thus may be accessed as previously described. Compounds 19-22 were reported in WO 2015/137838 A1. The disodium salt 37 was previously disclosed in Carbohydrate Res. 1967, 5, 453 but no particular function or effect of the compound was disclosed.

Gluco-, galacto- and mannuronic acids (Compounds 37-42) are prepared as described in Scheme 3. Due to the presence of the two carboxylic acid moieties, the resulting stabilizers are ionizable in two positions in contrast to trehaolse and saccharose which are devoid of charge.

Preparation of Diamido Gluco-, Manno- and Galactosides

Diamides from gluco-, manno- and galactosides 46-48 were prepared in by reaction of 43-45 with ammonia in methanol.

Scheme 4.

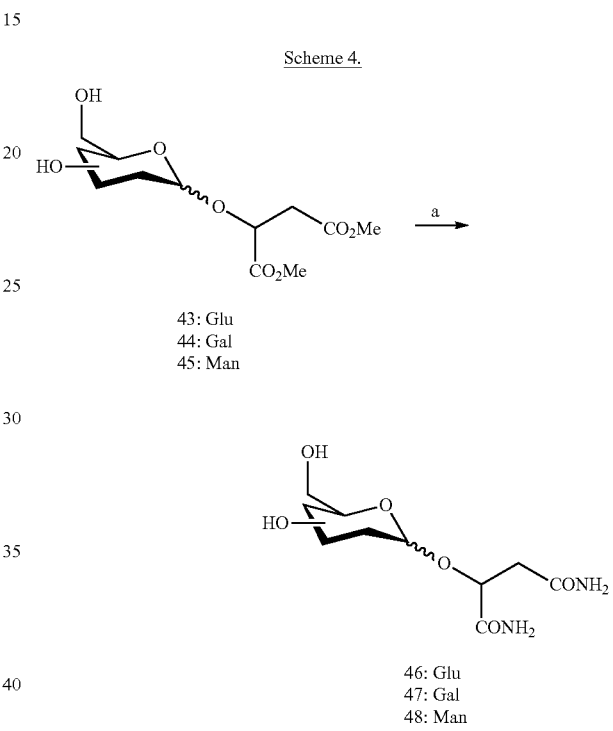

43: Glu
44: Gal
45: Man

46: Glu
47: Gal
48: Man a) NH$_3$, MeOH, -78° C. - r.t.

Preparation of Additional Dianionic Glucuronidated Acids

Gluco-, galacto- and mannuronic acids (Compounds 55-60) are prepared as described in Scheme 5.

Scheme 5.

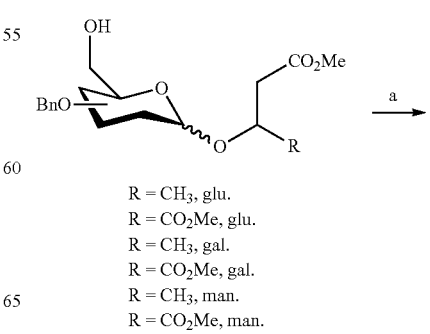

R = CH$_3$, glu.
R = CO$_2$Me, glu.
R = CH$_3$, gal.
R = CO$_2$Me, gal.
R = CH$_3$, man.
R = CO$_2$Me, man.

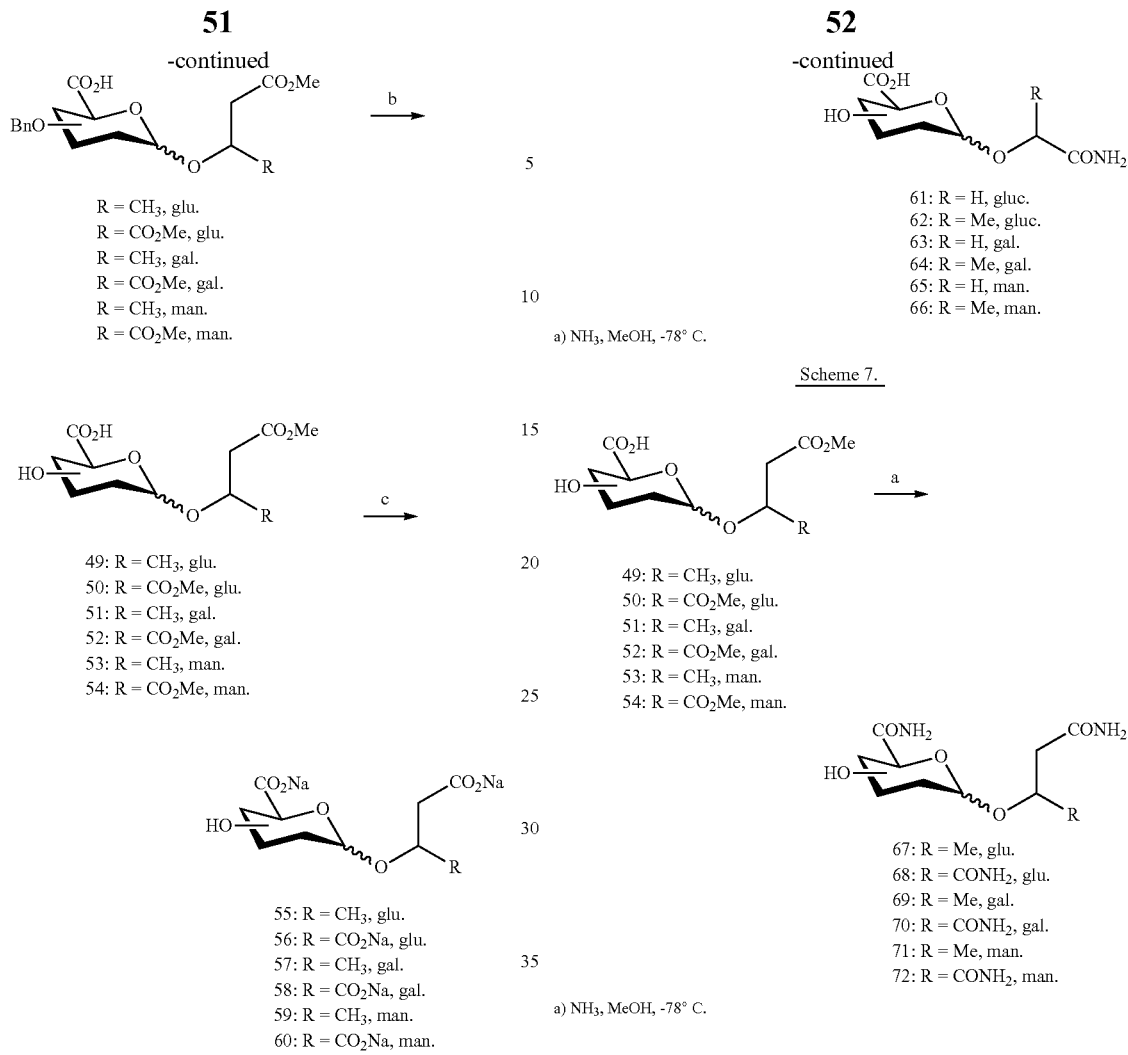

Scheme 6.

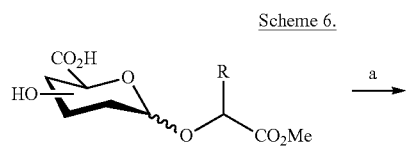

31: R = H, gluc.
32: R = Me, gluc.
33: R = H, gal.
34: R = Me, gal.
35: R = H, man.
36: R = Me, man.

Preparation of Uronic Acid Amides

Gluco-, galacto- and mannuronic acid amides (Compounds 61-66 and 67-72) were prepared as described in Schemes 6 and 7. Uronic acid amides 61-66 were prepared in by reaction of 31-36 with ammonia in methanol. Uronic acid amides 67-72 were prepared in by reaction of 49-54 with ammonia in methanol.

Synthesis and Characterization of Compounds

General Procedures $^1$H NMR spectra were obtained at 400 MHz in CDCl$_3$ with chemical shift values (δ) in ppm downfield from tetramethylsilane, and $^{13}$C NMR spectra were obtained at 100.61 MHz in CDCl$_3$. Medium pressure preparative column chromatography: Silica Gel Merck 60 H. Analytical TLC: Aluminium-backed Silica Gel Merck 60 F254. Reagents and solvents were purified and dried according to W. L. F. Armarego, C. L. L. Chai, Purification of Laboratory Chemicals, 5th ed.; 2003 Elsevier. Specific rotations ([α]D20): were measured by using a Perkin-Elmer D241 automatic polarimeter. All the reactions were carried out under an inert atmosphere (argon), except for the reactions in water.

Experiment 1. Synthesis of 2-O-(α-D-mannopyranosyl)acetamide (6)

A solution of 5 (3.01 g, 11.9 mmol) in MeOH (15 mL), in a sealed tube, was saturated with NH$_3$ at −78° C. The reaction mixture was stirred for 3 days at r.t. The excess of NH$_3$ was allowed to evaporate and after concentration, the product 6 was obtained as a white foam (quantitative yield). $^1$H NMR (D$_2$O, 400 MHz): δ4.85 (d, J=1.8 Hz, 1H), 4.17 (d, J=15.7 Hz, 1H), 4.05 (d, J=15.7 Hz, 1H), 4.00 (dd, J=3.5, 1.7 Hz, 1H), 3.84-3.81 (m, 2H), 3.69 (dd, J=12.2, 5.7 Hz, 1H), 3.64-3.57 (m, 2H) ppm. $^{13}$C NMR (D$_2$O, 100.61 MHz): δ 178.5, 99.9, 73.2, 70.3, 69.7, 66.6, 65.4, 60.8 ppm.

Experiment 2. Synthesis of (2S)-2-O-(α-D-mannopyranosyl)-3-propanamide (12)

The procedure of experiment 1 was applied to compound 11 (2.10 g, 7.9 mmol) affording compound 12 as a white foam (quantitative yield). $^1$H NMR (D$_2$O, 400 MHz): δ4.94 (d, J=1.6 Hz, 1H), 4.20 (q, J=6.8 Hz, 1H), 3.93 (dd, J=3.4, 1.7 Hz, 1H), 3.83 (dd, J=9.4, 3.4 Hz, 1H), 3.76 (dd, J=12.3, 2.4 Hz, 1H), 3.70-3.60 (m, 2H), 3.55 (m, J=10.0, 5.3, 2.4 Hz, 1H), 1.34 (d, J=6.8 Hz, 3H) ppm. $^{13}$C NMR (D$_2$O, 100.61 MHz): 3178.2, 98.7, 73.5, 72.7, 70.4, 70.1, 66.5, 60.7, 17.0 ppm.

Experiment 3. Synthesis of 2-(α/β-D-glucopyranosyl)acetamide (2)

The procedure of experiment 1 was applied to compound 1 (0.676 g, 2.68 mmol) affording compound 2 as a white foam (quantitative yield). 1H NMR (D$_2$O, 400 MHz): δ4.91 (d, J=3.8 Hz), 4.45 (d, J=7.9 Hz), 4.31 (d, J=16.0 Hz), 4.19 (d, J=15.9 Hz), 4.03 (d, J=15.9 Hz), 3.86-3.59 (m), 3.54 (dd, J=9.9, 3.8 Hz), 3.47-3.28 (m) ppm. $^{13}$C NMR (D$_2$O, 100.61 MHz): δ 174.9, 102.4, 98.6, 76.0, 75.5, 72.93, 72.79, 72.2, 71.1, 69.45, 69.38, 67.7, 65.9, 60.56, 60.40 ppm.

Experiment 4. Synthesis of (2S)-2-(α/β-D-glucopyranosyl)propanamide (8)

The procedure of experiment 1 was applied to compound 7 affording product 8 as a white foam (quantitative yield, a/3=11:1). $^1$H NMR (D$_2$O, 400 MHz): δ 5.01 (d, J=3.9 Hz), 4.45 (d, J=8.0 Hz), 4.38 (q, J=7.0 Hz), 4.18 (q, J=6.8 Hz), 3.87-3.77 (m), 3.75-3.65 (m), 3.62-3.55 (m), 3.54-3.49 (m), 3.48-3.32 (m), 1.38 (d, J=7.0 Hz), 1.35 (d, J=6.8 Hz) ppm. $^{13}$C NMR (D$_2$O, 100.61 MHz): δ 178.3, 101.6, 96.9, 76.1, 75.6, 75.2, 73.0, 72.8, 72.5, 71.6, 71.20, 71.03, 69.5, 69.3, 60.6, 60.2, 18.7, 16.9 ppm.

Experiment 5. Synthesis of 2-(α/β-D-galactopyranosyl)acetamide (4)

The procedure of experiment 1 was applied to compound 3 affording product 4 as a white foam (quantitative yield, α/β=2:1). $^1$H NMR (CDCl$_3$, 400 MHz): δ4.93 (d, J=3.8 Hz), 4.38 (d, J=7.6 Hz), 4.30 (d, J=16.0 Hz), 4.20-4.15 (m), 4.02 (d, J=15.9 Hz), 3.92-3.91 (m), 3.86 (dt, J=10.7, 4.3 Hz), 3.79 (dd, J=10.3, 3.8 Hz), 3.74-3.57 (m), 3.52 (dd, J=9.9, 7.6 Hz) ppm. $^{13}$C NMR (CDCl$_3$, 100.61 MHz): δ175.0, 102.9, 98.7, 75.3, 72.5, 71.4, 70.6, 69.19, 69.12, 68.5, 68.0, 67.7, 65.9, 61.1, 60.9 ppm.

Experiment 6. Synthesis of (2S)-2-(α/β-D-galactopyranosyl)propanamide (10)

The procedure of experiment 1 was applied to compound 9 affording product 10 as a white foam (quantitative yield, α/β=3:1). $^1$H NMR (CDCl$_3$, 400 MHz): 5.02 (d, J=3.9 Hz), 4.40-4.35 (m), 4.18 (q, J=6.8 Hz), 3.92 (d, J=3.1 Hz), 3.84 (dd, J=10.3, 3.3 Hz), 3.76 (dt, J=10.0, 4.8 Hz), 3.72-3.56 (m), 3.50 (dd, J=10.0, 7.8 Hz), 1.37 (d, J=7.0 Hz), 1.33 (d, J=6.8 Hz) ppm.

Experiment 7. Synthesis of 3-O-(α/β-D-glucopyranosyl)-3-hydroxybutyramide (14)

The procedure of experiment 1 was applied to compound 13 (0.396 g, 1.35 mmol) affording product 14 as a white foam (0.291 g, 82%). $^1$H NMR (CDCl$_3$, 400 MHz): δ 4.95 (d, J=3.8 Hz) 4.47 (d, J=7.9 Hz), 4.46 (d, J=7.9 Hz), 4.21-4.03 (m), 3.81-3.28 (m), 3.18-3.12 (m), 2.65-2.36 (m), 1.23-1.15 (m) ppm.

Experiment 8. Synthesis of 3-O-(β-D-galactopyranosyl)-3-hydroxybutyramide (16)

The procedure of experiment 1 was applied to compound 15 (0.820 g, 2.8 mmol) affording product 16 as a white foam (0.677 g, 90%). $^1$H NMR (CDCl$_3$, 400 MHz): δ 4.41 (d, J=7.9 Hz), 4.40 (d, J=7.9 Hz), 4.27-4.18 (m), 3.84-3.83 (bs), 3.73-3.55 (m), 3.42-3.38 (m), 2.53-2.38 (m), 1.24 (d, J=6.4 Hz), 1.18 (d, J=6.3 Hz) ppm. $^{13}$C NMR (CDCl$_3$, 100.61 MHz): δ176.6, 176.5, 102.0, 101.0, 75.2, 75.0, 73.9, 72.7, 72.7, 72.5, 70.8, 70.7, 68.6, 68.5, 60.9, 60.8, 42.7, 41.9, 20.4, 18.8 ppm.

Experiment 9. Synthesis of 3-O-(α-D-mannopyranosyl)-3-hydroxybutyramide (18)

The procedure of experiment 1 was applied to compound 17 (1.15 g, 3.9 mmol) affording product 18 as a white foam (0.711 g, 69%). $^1$H NMR (CDCl$_3$, 400 MHz): δ4.91 (d, J=1.4 Hz), 4.86 (d, J=1.7 Hz), 4.19-4.08 (m), 3.83-3.76 (m), 3.73-3.60 (m), 3.58-3.51 (m), 2.45-2.33 (m), 1.22 (d), 1.16 (d) ppm. $^{13}$C NMR (CDCl$_3$, 100.61 MHz): δ176.7, 99.9, 96.4, 73.0, 72.8, 72.7, 70.6, 70.5, 70.4, 70.2, 69.3, 66.8, 66.4, 60.9, 60.6, 42.9, 42.4, 20.6, 17.7 ppm.

Experiment 10. Synthesis of Disodium 2-(α/β-D-glucopyranosiduronic)acetate (37)

To a vigorously stirred solution of 19 (1.44 g, 2.76 mmol) in 9.2 mL DCM and 9.2 mL H$_2$O was added TEMPO (0.178 g, 0.55 mmol) and BAIB (1.08 g, 6.91 mmol). After complete conversion of the starting material the reaction mixture was quenched with 10% solution of Na$_2$S$_2$O$_3$ (20 mL), followed by extraction with EtOAc (3×20 mL). The combined organic layers were dried with MgSO4, filtered and concentrated. Flash column chromatography using (70:30, EtOAc/Hex) afforded the product 25 as a colourless viscous foam (1.185 g, 80%). A solution of 25 in EtOAc was hydrogenated at 50 psi in the presence of Pd/C 10% (0.25 equiv). After 5 hours, the reaction mixture was filtered and the solvent was evaporated to afford 31 as a very viscous colourless foam. A solution of 1M NaOH (2 eq.) was added to a stirred solution of compound 31 in H$_2$O (2 mL). After all of the starting material had been consumed, the pH was adjusted to 7 with 10% HCl and the solvent was evaporated to afford 37 as a viscous colorless foam (70%, 4 steps overall yield). $^1$H NMR (CDCl$_3$, 400 MHz): δ4.98 (d, J=3.9 Hz), 4.40 (d, J=7.9 Hz), 4.26 (q, J=7.0 Hz), 4.03 (q, J=6.8 Hz), 3.96 (d, J=10.1 Hz), 3.77 (t, J=9.5 Hz), 3.73-3.69 (m), 3.65-3.63 (m), 3.58 (dd, J=11.7, 4.3 Hz), 3.51 (dd, J=9.8, 3.9 Hz), 3.46-3.44 (m), 3.40 (t, J=9.6 Hz, 1H), 3.32-3.28 (m), 1.34 (d, J=6.9 Hz), 1.29 (d, J=6.8 Hz) ppm. $^{13}$C NMR (CDCl$_3$, 100.61 MHz): δ180.9, 176.8, 101.7, 96.5, 76.7, 76.2, 75.6, 74.6, 73.2, 72.8, 72.4, 72.2, 71.7, 71.2, 18.9, 17.3 ppm.

Experiment 11. Synthesis of Disodium
(2S)-2-(α/β-D-glucopyranosiduronic) Propanoate
(38)

The procedure of experiment 10 was applied to compound 20 affording product 38 as a viscous colorless gum (66%, 4 steps overall yield). $^1$H NMR (CDCl$_3$, 400 MHz): δ4.90 (d, J=3.7 Hz), 4.43 (d, J=7.8 Hz), 4.26 (d, J=15.5 Hz), 4.09 (d, J=15.5 Hz), 3.89 (dd, J=12.9, 2.4 Hz), 3.78-3.62 (m), 3.57-3.33 (m) ppm. $^{13}$C NMR (CDCl$_3$, 100.61 MHz): δ177.4, 176.6, 102.1, 98.3, 73.1, 72.9, 72.3, 71.96, 71.76, 71.46, 71.26, 69.5, 66.86, 66.78 ppm.

Stabilization Studies

The ability of the new compounds to stabilise several proteins including enzymes and monoclonal antibodies was assessed using DSF and high performance size exclusion chromatography (HPSEC), under thermal and/or pH stresses (See, FIGS. 1 to 5). HPSEC can be used to assess the ability of compounds of stabilize biological molecules in the absence of thermal stress. The proteins used in the stabilisation assays were lysozyme, adalimumab (Humira®), ubiquitin and factor IX.

Differential Scanning Fluorimetry (DSF) Assay

The protein melting temperature (Tm) determination was performed by monitoring protein unfolding with the fluoroprobe SYPRO Orange dye (Molecular Probes), which although completely quenched in aqueous environment, emits fluorescence upon binding to protein hydrophobic patches. Such increase in fluorescence can be measured as a function of temperature. The thermal shift assay was performed on an iCycle iQ5 Real Time PCR Detection System (Bio-Rad), equipped with a charge-coupled device (CCD) camera and a Cy3 filter with excitation and emission wavelengths of 490 and 575 nm, respectively. This equipment can simultaneously detect the fluorescence changes in 96-well plates (low profile plate, Bio-Rad) and thus can be used for parallel thermal stability assays. The 96-well plates are sealed with optical quality sealing tape (Bio-Rad) and centrifuged at 2500 g for 1 minutes immediately before the assay to remove possible air bubbles. The plates are subsequently heated from 20 to 90° C. with stepwise increments of 1° C. with 60 seconds equilibration time, followed by the fluorescence read out. Fluorescence intensities versus temperature are used to calculate the protein melting temperature (Tm) by determining the first derivative (d(Rfu)/dT) and extract the exact transition inflection point. Delta T$_M$ values (DT$_M$) for the various conditions were calculated by subtracting the T$_M$ value obtained for the reference from the T$_M$ value obtained for each condition.

In a typical assay with a total volume of 20 μL, a protein concentration from 0.1-0.5 mg/mL and a dye concentration of 5 fold were used to guarantee the best signal to noise ratio. The protein stock solutions were prepared in their corresponding buffers before performing the DSF experiments. Stabiliser solutions and dyes were prepared according to each assay specific conditions. The assay was prepared by adding 1-2 μL of protein to 8-9 μL of dye buffer solution, and 10 μL of compound solution. Controls were prepared by replacing the volume of stabilisers by the correspondent buffer.

High Performance Size Exclusion Chromatography (HPSEC) Assay

HP-SEC was performed with Waters 515 pump, a Waters 2487 Dual Absorbance Detector (Waters, USA) and a Rheodyme 77251 injector (Waters, USA). A TSK Gel G3000 SWXL column (300 mm×7.8 mm) (Tosoh Biosep, Germany) was used. The volume of injection was adjusted according to each sample concentration in order to inject 50 mg sample of biological molecule, and separation was performed at a flow rate of 1.0 mL/min or adjusted as appropriate. A suitable running buffer was used, e.g., 100 mM sodium sulfate, 100 mM sodium phosphate dibasic pH 6.8 for Humira® samples. UV detection was performed at a wavelength suitable to detect the biological molecule, e.g., 280 nm. No thermal stress was applied and assay was performed at room temperature. Absorbance was measured to determine the concentration of biological molecule and thus determine amount of degradation of the biological molecule.

Experiment 10—Stabilization of Lysozyme Measured by DSF

The stabilization of lysozyme in the presence of several stabilisers at 0.25 M concentration and at pH 3.6 and pH 12 was studied using DSF (FIG. 1). At higher pH (12) lysozyme was less stable and showed a decrease in its melting temperature. The stabilization effect of The neutral amide-containing glycosides, namely, mannosyl-glycolamide (MglyA), mannosyl-lactamide (MLA) 3-glucosyl-butanamide (GBA), galactosyl-glycolamide (GaGlyA), galactosyl-lactamide (GaLA), beta-glucosyl-glycolamide (b-GGlyA), beta-glucosyl-lactamide (b-GLA), beta-galactosyl-glycolamide (b-GaGlyA), beta-3-galactosyl-butanamide (b-GaBA) and beta-galactosyl-lactamide (b-GaLA) described hereinabove, showed a stabilization effect. The stabilization effect was higher for GBA, GaGlyA, b-GGlyA, b-GaLA, b-GaGlyA, and b-GaBA at the higher pH (pH 12). All new compounds are able to stabilise lysozyme under both stress conditions.

Experiment 11—Stabilization Assay of Adalimumab (Humira®) Measured by HPSEC

Figure 2:
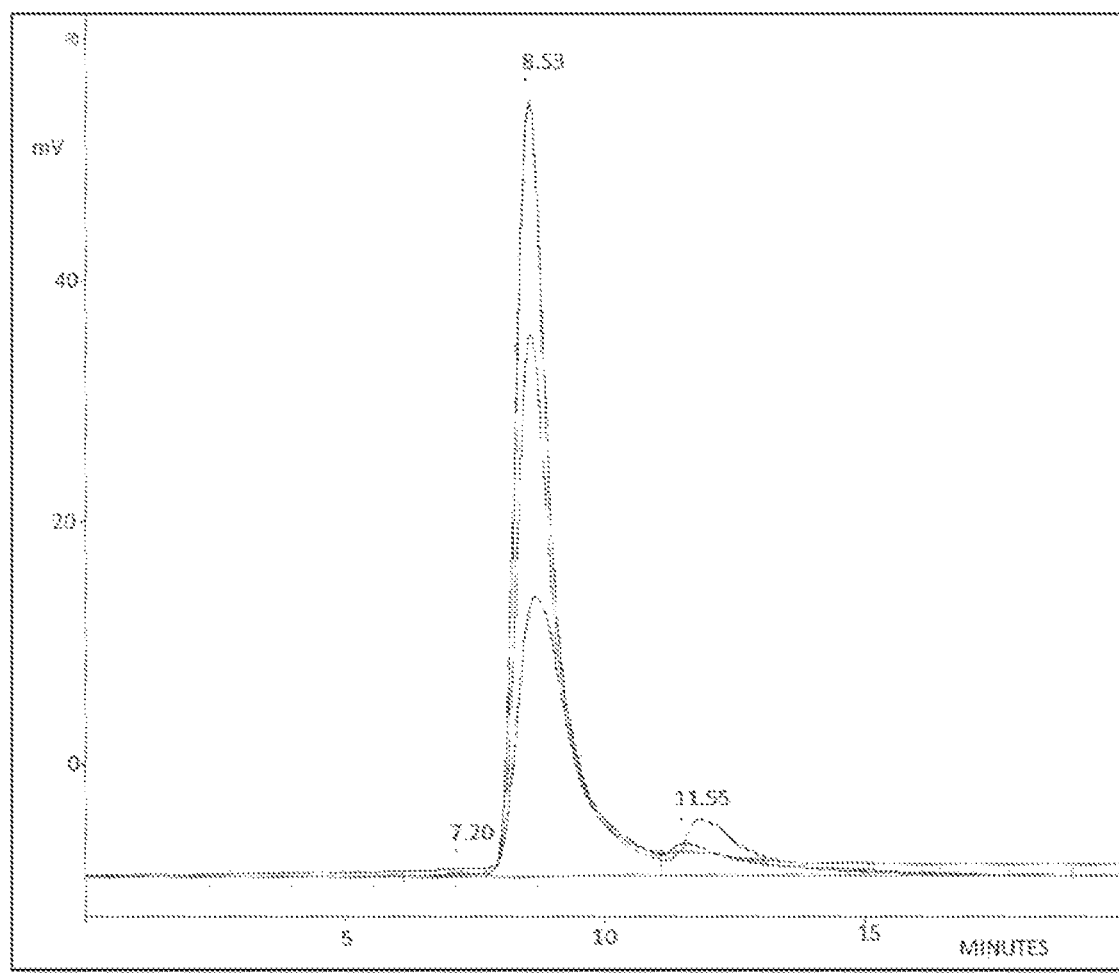
FIG. 2 shows HP-SEC chromatograms of Humira® samples at 0.4 mg/ml under low pH (stress). The line with the highest peak corresponds to a control sample: fresh Humira® (T=0h) in pH 5.5 citrate buffer. The line with the second highest peak corresponds to the Humira® at pH 3.2 in the presence of GaGlyA over twelve hours and the line with the third highest peak corresponds to Humira® at pH 3.2 without GaGlyA over twelve hours.

A pH titration of adalimumab (Humira®) to pH 3.2 was performed either in the absence and presence of stabiliser GaGlyA 0.5 M, and the results were analysed by HPSEC (FIG. 2). The volume of injection was adjusted according to each sample concentration in order to inject 50 mg of Humira, and separation was performed at a flow rate of 1.0 mL/min. The running buffer was composed of 100 mM sodium sulfate, 100 mM sodium phosphate dibasic pH 6.8. UV detection was performed at 280 nm. This assay was performed at room temperature, no thermal stress was applied, contrary to the DSF assays. Absorbance was measured to determine the concentration of biological molecule and thus determine amount of degradation of the biological molecule. Adalimumab degrades after 12 hours at pH 3.2 (FIG. 2, line C), however in the presence of GaGlyA this degradation is much reduced (FIG. 2, line B).

Experiment 12—Stabilization Assay of Adalimumab Measured by DSF

Figure 3:
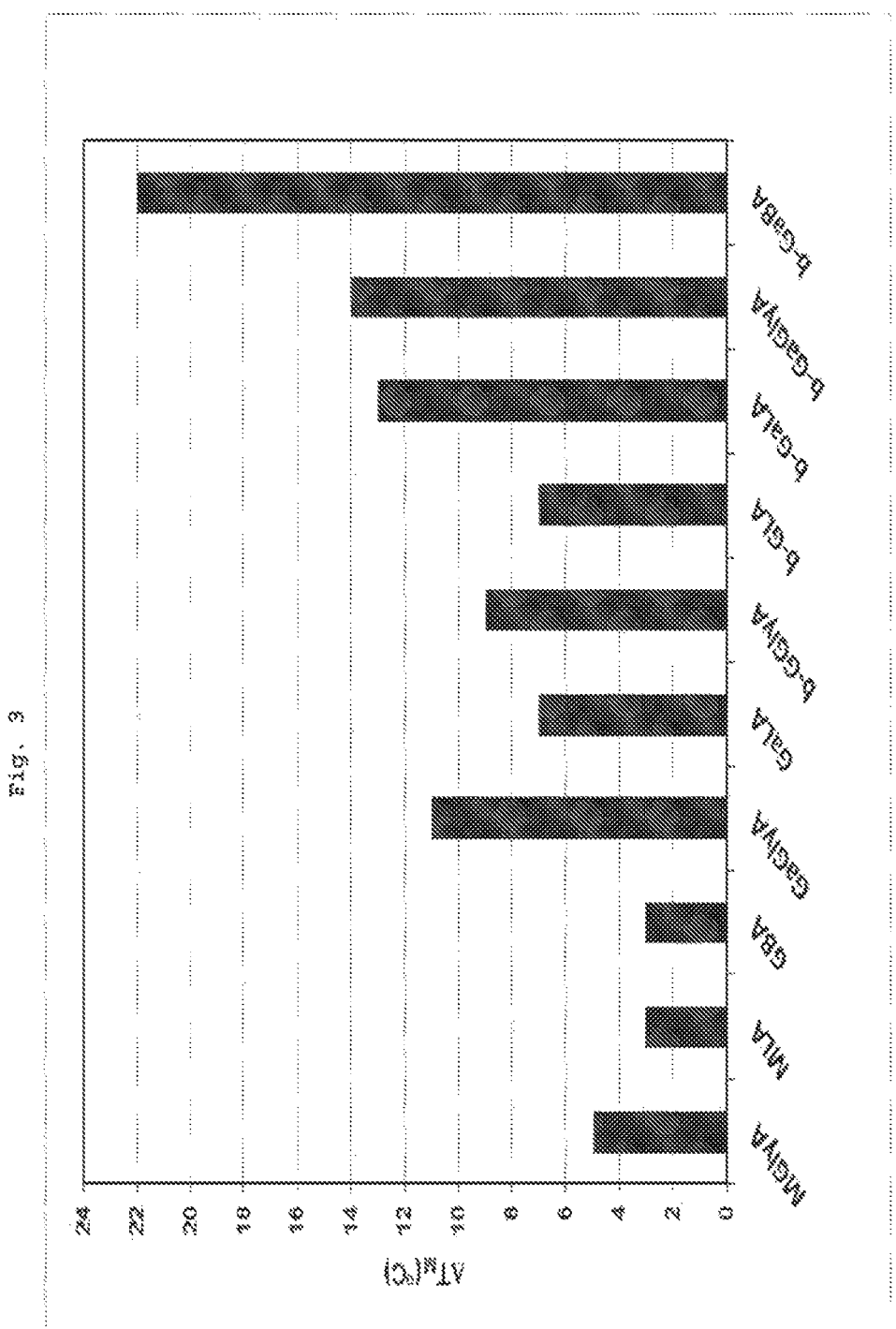
FIG. 3 shows the increase of the melting temperature (Tm) of Humira® in the presence of 0.25 mM of various compounds (MGlyA, MLA, GBA, GaGlyA, GaLA, b-GGlyA, b-GLA, b-GaLA, b-GaGlyA, b-GaBA from left to right) in phosphate buffer at pH 12. The melting temperature (Tm) of Humira® in the absence of compounds was 41° C. in phosphate buffer.

The stabilisation of adalimumab was also assessed in the presence of 0.25 M of several stabilisers at pH 12, using DSF (FIG. 3). All the tested compounds stabilised adalimumab, and a higher stabilisation was obtained with beta-3-galactosyl-butanamide (b-GaBA), with a 22° C. increase of the melting temperature of the monoclonal antibody.

Experiment 13—Stabilization Assay of Ubiquitin Measured by DSF

Figure 4:
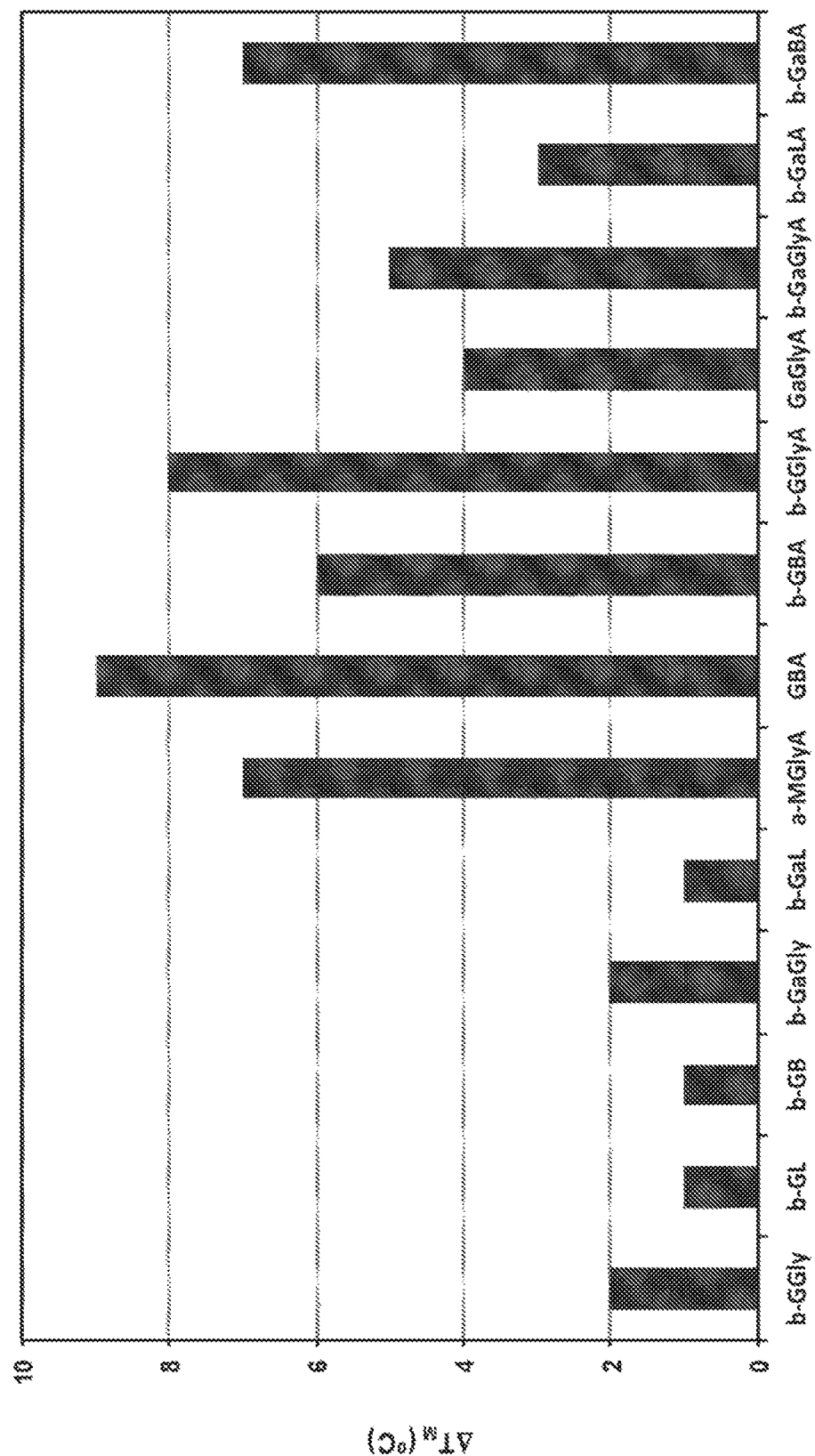
FIG. 4 shows the increase of the melting temperature (Tm) of ubiquitin in the presence of 0.25 M of various compounds (b-GGly, b-GL, b-GB, b-GaGly, b-GaL, a-MGlyA, GBA, b-GBA, b-GGlyA, b-GaGlyA, GaLA, b-GaLA, b-GaBA from left to right) in phosphate buffer at pH 12. The melting temperature (Tm) of ubiquitin in the absence of compounds was 72° C. in phosphate buffer.

Stabilization of ubiquitin using neutral amide-containing glycosides of the present invention as well as using charged glycosides were measured using DSF. Ubiquitin was equally stabilised in the presence of several new compounds at 0.25 M, at pH 12 (FIG. 4). In comparison to the charged glycosides, namely, beta-glucosyl-glycolate (b-Ggly), beta-glucosyl-lactate (b-GL), beta-3-glucosyl-butyrate (b-GB), beta-galactosyl-glicolate (b-GaGly); and beta-galactosyl-lactate (b-GaL), the neutral amide-containing glycosides resulted in significantly better stabilization of ubiquitin at pH 12. For the charged glycosides, the best results were an increase of the melting temperature of only 2° C., while neutral amide-containing glycoside, for example, 3-glucosyl-butanamide (GBA), was able to increase the melting temperature of ubiquitin as much as 9° C. (FIG. 4). The neutral amide-containing glycosides were better stabilisers than the carboxylic acid containing glycosides as shown in FIG. 4.

Experiment 14—Stabilization Assay of Factor IX Measured by DSF

Figure 5:
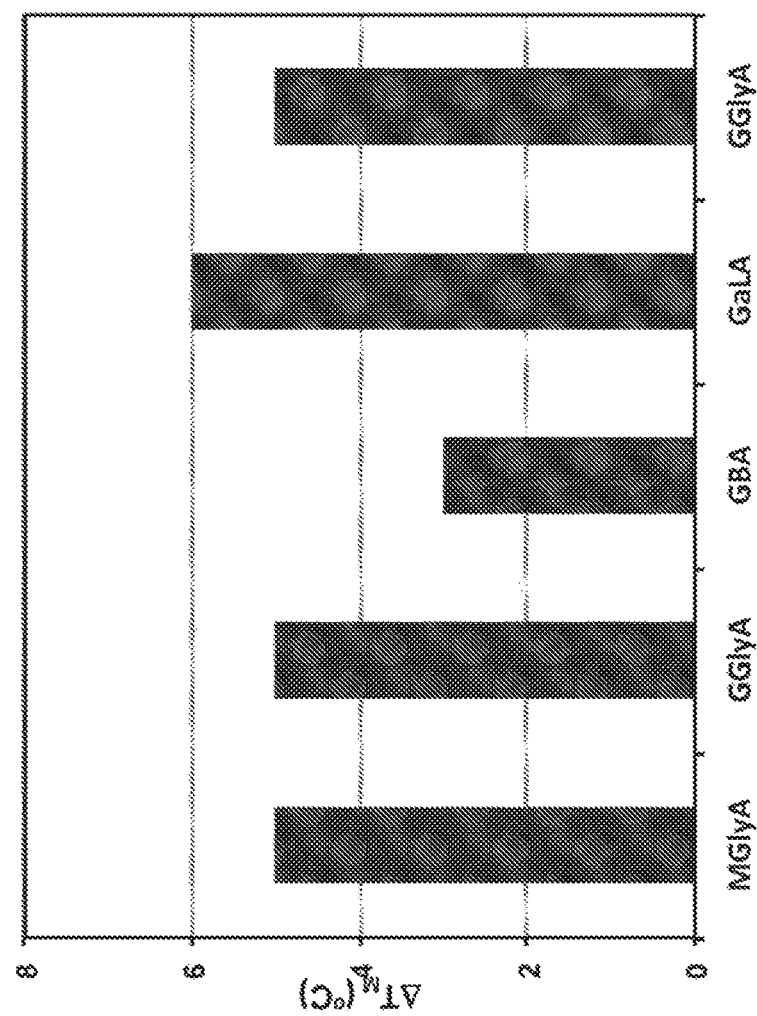
FIG. 5 shows the increase of the melting temperature (Tm) of Factor IX in the presence of 0.25 M of various compounds (MGlyA, GGlyA, GBA, GaLA, GGlyA from left to right) in water. The melting temperature (Tm) of Factor IX in the absence of compounds was 50° C. in water. The pH of assays in the presence of the compounds was between pH 7 and 8.

Stabilization of Factor IX using neutral amide-containing glycosides of the present invention were measured using DSF. The new stabilizers increased the melting temperature of factor IX at a 0.25 M concentration in water and at pH 7-8, as shown in FIG. 5. Mannosyl-glycolamide (MglyA), glucosyl-glycolamide (GGlyA), 3-glucosyl-butanamide (GBA) and galactosyl-lactamide (GaLA) showed stabilization of factor IX.

Experiment 15—Hydroxymethyl Derivatives

The hydroxymethyl amide derivatives are prepared from glycosylation of the glycosyl donor (manno-, gluco-, galactopyranose) with the corresponding glycosyl acceptor using methods described in literature (Carbohydrate Research 343 (2008), 3025-3033) and by further reaction of the unprotected sugar with ammonia in methanol.

The hydroxymethyl uronic derivatives are prepared from glycosylation of the glycosyl donor (manno-, gluco-, galactopyranose) with the corresponding glycosyl acceptor using methods described in literature (Carbohydrate Research 343 (2008), 3025-3033) and by further oxidation of the C-6 primary hydroxyl group to the corresponding carboxylic acid with a BAIB/Tempo reagent combination.

The hydroxymethyl diamide derivatives are prepared from the respective hydroxymethyl uronic derivatives (mann-, gluc-, galacturonic) by further reaction of the unprotected sugar with ammonia in methanol.

DISCUSSION

There is a major need for new stabilizers of biological molecules. The assays above show that the compounds of the present invention stabilize biological molecules under a variety of conditions. The results of the DFS studies (Experiments 10, 12, 13 and 14) show that the neutral glycosylated amides stabilize a wide range of biological molecules under both pH stress and thermal stress. The increased Tm values correspond to greater structural stability of the biological molecule. The results of the HPSEC study (Experiment 11) shows that the neutral glycosylated amides also stabilize biological molecules under pH stress in the absence of thermal stress. The absorbance (mV) values show that the compounds of the present invention have the ability to protect biological molecules from pH induced degradation. The neutral glycosylated amides offer unexpectedly improved protection from pH stress in comparison to prior stabilizers. See, comparative data of Experiment 13 and FIG. 4 which shows that the neutral glycosylated amides stabilize the given biological molecule to a greater effect than charged glycosides as evidenced by the increased melting temperature of the biological molecule.

In summary, new molecules were identified that stabilize biological molecules under both thermal and pH stress. These molecules were shown to stabilize biological molecules from pH induced stress even in the absence of thermal stress. Compared to prior charged glycosides, these compounds have been shown to be superior stabilizers of biological molecules under pH stress.

REFERENCES

1. Chang B S, Yeung B. (2010) Physical Stability Of Protein Pharmaceuticals in Formulation And Process Development Strategies For Manufacturing Biopharmaceuticals (Feroz Jameel and Susan Hershenson eds). John Wiley & Sons Inc. pp. 69-104
2. Ueda T, Nagata M, Imoto T. (2001) Aggregation and chemical reaction in hen lysozyme caused by heating at pH 6 are depressed by osmolytes, sucrose and trehalose. 491-496
3. Kaushik J K, Bhat R. (2003) Why is trehalose an exceptional protein stabilizer? An analysis of the thermal stability of proteins in the presence of the compatible osmolyte trehalose. J Biol Chem 278(29):26458-26465
4. Singer M A, Lindquist S. (1998) Multiple effects of trehalose on protein folding in vitro and in vivo. Mol. Cell 1(5):639-648
5. Lin T Y, Timasheff S N. (1996) On the role of surface tension in the stabilization of globular proteins. Protein Sci 5(2):372-381
6. Reed R H, Borowitzka L J, Mackay M A, Chudek J A, Foster R, Warr SCR, Moore D J, Stewart W D P. (1986) Organic solute accumulation in osmotically stressed cyanobacteria. FEMS Microbiol Rev 39:51-56.
7. Ohtake S, Wang Y J. (2011) Trehalose: Current Use and Future Applications. J. Pharm. Sciences, 100, 2020-2053
8. Lee J C, Timasheff S N. (1981) The stabilization of proteins by sucrose. J Biol Chem. July 25; 256(14):7193-201.
9. Jain N K, Roy I. (2009) Effect of trehalose on protein structure. Protein Sci. 18, 24
10. Andya J D, Hsu C C, Shire S J. (2003) Mechanisms of Aggregate Formation and Carbohydrate Excipient Stabilization of Lyophilized Humanized Monoclonal Antibody Formulations. AAPS PharmSci. 5 (2), article 10.
11. Khan S H, Ahmad N, Ahmad F, Kumar R. (2010) Naturally occurring organic osmolytes: From cell physiology to disease prevention. IUBMB Life, 62, 891-895
12. Rajan R S, Tsumoto K, Tokunaga M, Tokunaga H, Kita Y, Arakawa T. (2011) Chemical and pharmacological chaperones: application for recombinant protein production and protein folding diseases, Curr. Med. Chem., 18, 1-15
13. Stidham S E, Chin S L, Dane E L, Grinstaff M W. (2014) Carboxylated glucuronic poly-amido-saccharides as protein stabilizing agents, J. Am. Chem. Soc., 136, 9544-9547
14. Trombotto S, Danel M, Fitremann J, Bouchu A, Queneau Y. (2003) Straightforward Route for Anchoring a Glucosyl Moiety onto Nucleophilic Species: Reaction of Amines and Alcohols with Carboxymethyl 3,4,6-Tri-O-acetyl-r-D-glucopyranoside 2-O-Lactone. J. Org. Chem. 2003, 68, 6672
15. Trombotto S, Bouchu A, Descotes G, Queneau Y. (2000) Hydrogen peroxide oxidation of palatinose and trehalulose: direct preparation of carboxymethyl a-D-glucopyranoside. Tetrahedron Lett. 2000, 41, 8273-8277
16. Fischer L, Bromann R, Wagner F. (1995) Enantioselective Synthesis of Several 1-O-beta-D-glucoconjugates Using Almond beta-Glucosidase (E.C.3.2.1.21). Biotech. Lett. Vol. 17, No. 11, November 1995, pp. 1169-1174
17. Matsumura S, Yamazaki H, Toshima K. (1997) R-Enantioselective Galactosylation Of Secondary Alcohols Using beta-Galactosidase. Biotech. Lett., Vol. 19, No. 6, June 1997, pp. 583-586
18. Krajewski D, Duque C, Schreier P. (1997) Aliphatic Beta-D-Glucosides From Fruits Of Carica Pubsecens. Phytochemistry, Vol. 45, No. 8, pp. 1627-1630
19. Faria T Q, Mingote A, Siopa F, Ventura R, Maycock C, Santos H (2008) Design of new enzyme stabilizers inspired by glycosides of hyperthermophilic microorganisms. Carbohydrate Res. 2008, 343, 3025-3033.
20. Xue J L, Cecioni S, He L, Vidal S, Praly J P. (2009) Variations on the SnCl4 and CF3CO2Ag-promoted glycosidation of sugar acetates: a direct, versatile and apparently simple method with either alpha or beta stereocontrol. Carbohydrate Res. 2009, 344, 1646
21. Moynihan H A, Hayes J A, Eccles K S, Coles S J, Lawrence S E. (2013) Hydrogen bonding in crystal forms of primary amide functionalized glucose and cellobiose. Carbohydrate Res. 2013, 374, 29
22. PCT International Application Publication No. WO 2008/007153 A2
23. PCT International Application Publication No. WO 2012/109263 A1
24. PCT International Application Publication No. WO 2015/137838 A

What is claimed is:

1. A compound having the structure:

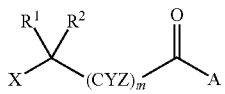

a) wherein
X is a hexosyl group selected from a group consisting of glucosyl, mannosyl, allosyl, altrosyl, gulosyl, idosyl and talosyl;
$R^1$ is H, halogen, OH, O-alkyl, $CONH_2$, $CO_2H$, $CO_2$-alkyl, or optionally substituted alkyl;
$R^2$ is H, halogen, OH, O-alkyl, $CONH_2$, $CO_2H$, or $CO_2$-alkyl;
each of Y and Z is independently H, OH, O-alkyl or optionally substituted alkyl;
m is 0, 1 or 2; and
$A=NR^3R^4$,
wherein each of $R^3$ and $R^4$ is independently H, OH, O-alkyl or optionally substituted alkyl;
wherein
when X is glucosyl, then $R^1$ is optionally substituted alkyl, and
when X is glucosyl, m=0, $R^1$ is -alkyl-OH and $R^2$ is —H, and A is $NH_2$, then the compound is a beta-anomer; and
when X is mannosyl, m=0, $R^1$ is -alkyl-OH and $R^2$ is —H, then A is other than $NH_2$;

or
b) wherein
X is galactosyl;
$R^1$ is halogen, OH, O-alkyl, $CONH_2$, $CO_2H$, $CO_2$-alkyl, or optionally substituted alkyl;
$R^2$ is H, halogen, OH, O-alkyl, $CONH_2$, $CO_2H$, or $CO_2$-alkyl;
each of Y and Z is independently H, OH, O-alkyl or optionally substituted alkyl;
m is 0, 1 or 2; and
$A=NR^3R^4$,
wherein each of $R^3$ and $R^4$ is independently H, OH, O-alkyl or optionally substituted alkyl;
and
wherein in (a) and/or (b), the alkyl is $C_{1-11}$ alkyl or $C_3$-$C_8$ cycloalkyl; and
wherein in (a) and/or (b), the substitution of any optionally substituted alkyl is F, Cl, Br, I, methyl, ethyl, n-propyl, isopropyl, n-butyl, tert-butyl, trifluoromethyl, hydroxyl, methoxy, ethoxy, n-propoxy, isopropoxy, phenoxy, benzyloxy, p-trifluoromethylbenzyloxy, trifluoromethanesulfonyl, methanesulfonyl, p-toluenesulfonyl, nitro, nitrosyl, mercapto, methylsulfanyl, ethylsulfanyl and propylsulfanyl, cyano, methylamino, dimethylamino, ethylamino, or diethylamino;
or a salt thereof.

2. The compound of claim 1 having the structure:

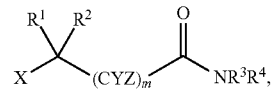

a) wherein
X is a hexosyl group selected from a group consisting of glucosyl and mannosyl;
$R^1$ is H, OH, O-alkyl or optionally substituted alkyl;
$R^2$ is H, halogen, OH, O-alkyl, $CONH_2$, $CO_2H$, or $CO_2$-alkyl;
each of $R^3$ and $R^4$ is independently H, O-alkyl or optionally substituted alkyl;
each of Y and Z is H;
m is 0, 1 or 2, and
when X is glucosyl, then $R^1$ is optionally substituted alkyl,
or
b) wherein
X is galactosyl;
$R^1$ is halogen, OH, O-alkyl, $CONH_2$, $CO_2H$, $CO_2$-alkyl, or optionally substituted alkyl;
$R^2$ is H, halogen, OH, O-alkyl, $CONH_2$, $CO_2H$, or $CO_2$-alkyl;
each of Y and Z is independently H, O-alkyl or optionally substituted alkyl;
m is 0, 1 or 2; and
each of $R^3$ and $R^4$ is independently H, OH, O-alkyl or optionally substituted alkyl.

3. The compound of claim 1, wherein

X is or galactosyl, wherein each of Y and Z is H, wherein $R^1$ is $CH_3$ and $R^2$ is H, or $R^1$ is $CONH_2$ and $R^2$ is H, or $R^1$ is $CO_2CH_3$ and $R^2$ is H, and/or wherein each of $R^3$ and $R^4$ is H.

4. The compound of claim 1 having the structure:

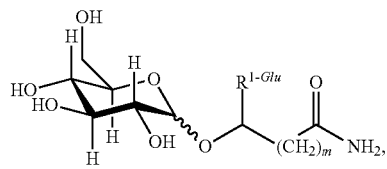

wherein $R^{1\text{-}Glu}$ is an optionally substituted alkyl and m is 1 or 2;

or

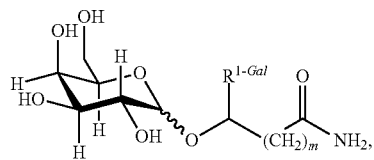

wherein $R^{1\text{-}Gal}$ is optionally substituted alkyl, or $CONH_2$ and m is 0, 1 or 2;

or

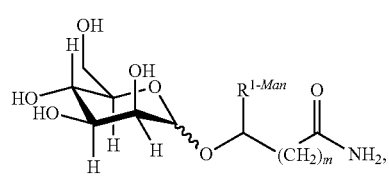

wherein $R^{1\text{-}Man}$ is H, an optionally substituted alkyl, or $CONH_2$ and m is 1 or 2.

5. The compound of claim 1, wherein the hexosyl group is an alpha-anomer; or wherein the hexosyl group is a beta-anomer.

6. The compound of claim 1 having the structure:

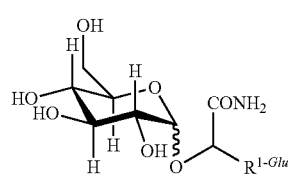

wherein $R^{1\text{-}Glu}$ is optionally substituted alkyl and the compound is a beta-anomer; or

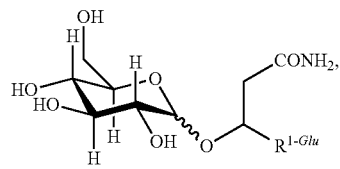

wherein $R^{1\text{-}Glu}$ is optionally substituted alkyl; or

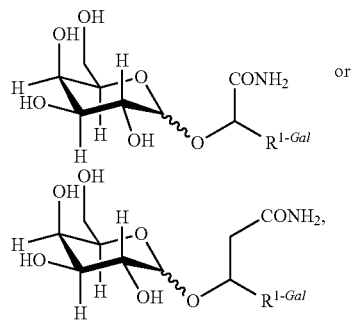

wherein $R^{1\text{-}Gal}$ is optionally substituted alkyl or $CONH_2$; or

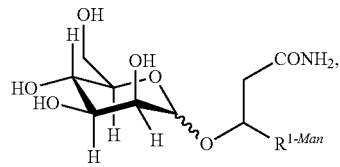

wherein $R^{1\text{-}Man}$ is H, an optionally substituted alkyl, or $CONH_2$.

7. A composition comprising a biological molecule and a compound having the structure

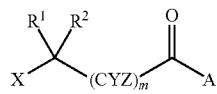

wherein
X is a hexosyl group selected from the group consisting of glucosyl, mannosyl, galactosyl, allosyl, altrosyl, gulosyl, idosyl and talosyl, or a uronic acid group selected from the group consisting of glucuronic acid, mannuronic acid, galacturonic acid, alluronic acid, altruronic acid, guluronic acid, iduronic acid and taluronic acid, or an uronic acid amide group selected from the group consisting of glucuronamide, mannuronamide, galacturonamide, alluronamide, altruronamide, guluronamide, iduronamide and taluronamide;

$R^1$ is H, halogen, OH, O-alkyl, $CONH_2$, $CO_2H$, $CO_2$-alkyl, or optionally substituted alkyl;

$R^2$ is H, halogen, OH, O-alkyl, $CONH_2$, $CO_2H$, or $CO_2$-alkyl;

each of Y and Z is independently H, OH, O-alkyl or optionally substituted alkyl;

m is 0, 1 or 2; and $A=NR^3R^4$ or $OR^5$, wherein
each of $R^3$ and $R^4$ is independently H, OH, O-alkyl or optionally substituted alkyl;
$R^5$ is optionally substituted alkyl;
wherein when X is glucosyl, then $R^1$ is optionally substituted alkyl, when each of $R^1$ and $R^2$ is H and m is 0, then X is other than glucuronic acid,
and
wherein when X is glucosyl or mannosyl, m=0, $R^1$ is -alkyl-OH and $R^2$ is —H, and A is $NH_2$, then the compound is a beta-anomer;
and
wherein the alkyl group of any alkyl is $C_{1-12}$ alkyl or $C_3$-$C_8$ cycloalkyl and
wherein the substitution of any optionally substituted alkyl is F, Cl, Br, I, methyl, ethyl, n-propyl, isopropyl, n-butyl, tert-butyl, trifluoromethyl, hydroxyl, methoxy, ethoxy, n-propoxy, isopropoxy, phenoxy, benzyloxy, p-trifluoromethylbenzyloxy, trifluoromethanesulfonyl, methanesulfonyl, p-toluenesulfonyl, nitro, nitrosyl, mercapto, methylsulfanyl, ethylsulfanyl and propylsulfanyl, cyano, amino, methylamino, dimethylamino, ethylamino, diethylamino, or carboxy, and
wherein the biological molecule is a biopharmaceutical, protein, nucleotide, polypeptide or antibody.

8. The composition of claim 7, wherein the biological molecule is Insulin; Insulin human inhalation; Insulin aspart; Insulin glulisine; Insulin lispro; Isophane insulin; Insulin detemir; Insulin glargine; Insulin zinc extended; Pramlintide acetate; Growth hormone (GH); somatotropin; genotropin; humatrope; norditropin; Mecasermin; Mecasermin rinfabate; Factor VIII; Factor IX; Antithromin III (AT-III); Protein C concentrate; β-Glucocerebrosidase; β-Glucocerebrosidase; Alglucosidase-α; Laronidase (α-1-iduronidase); Idursulphase (Iduronate-2-sulphatase); Galsulphase; Agalsidase-β (human α-galactosidase A); α-1-Proteinase inhibitor; Lactase; Pancreatic enzymes (lipase, amylase, protease); Pooled immunoglobulins; Human albumin; Albumin; Buminate; Erythropoietin; Epoetin-α; Darbepoetin-α; Filgrastim (granulocyte colony stimulating factor; G-CS F); Pegfilgrastim (Peg-G-CSF); Sargramostim (granulocytemacrophage colony stimulating factor; GM-CS F); Oprelvekin (interleukin 11; IL11); Human follicle-stimulating hormone Human chorionic gonadotropin (HCG); Type I alpha-interferon; interferon alfacon 1; consensus interferon; Infergen; Interferon-α2a (IFNα2a); PegInterferon-α2a; Interferon-α2b (IFNα2b); PegInterferon-α2b; Interferon-αn3 (IFNαn3); Interferon-β1a (rIFN-β); Interferon-β1b (rIFN-β); Interferon-γ1b (IFNγ); Aldesleukin (interleukin 2 (IL2); epidermal thymocyte activating factor; ETAF); Alteplase (tissue plasminogen activator; tPA); Reteplase (deletion mutein of tPA); Tenecteplase; Urokinase; Abbokinase; Factor VIIa; Drotrecogin-α (activated protein C); Salmon calcitonin; Teriparatide (human parathyroid hormone residues 1-34); Exenatide; Octreotide; Sandostatin; Dibotermin-α (recombinant human bone morphogenic protein 2; rhBMP2); Recombinant human bone morphogenic protein 7 (rhBMP7); Osteogenic protein 1; Histrelin acetate (gonadotropin releasing hormone; GnRH); Palifermin (keratinocyte growth factor KGF); kepivance; Becaplermin (platelet-derived growth factor; PDGF); Trypsin; Nesiritide; Botulinum toxin type A; Botox; Botulinum toxin type B; Collagenase; Human deoxy-ribonuclease I; dornase-α; Amphadase (bovine); hydase (bovine); Hyaluronidase (recombinant human); Papain; accuzyme; L-asparaginase; Peg-asparaginase; Rasburicase; Lepirudin; Bivalirudin; Streptokinase; Streptase; Anistreplase (anisoylated plasminogen streptokinase activator complex; APSAC); Bevacizumab; Cetuximab; Panitumumab; Alemtuzumab; Rituximab; Trastuzumab; Abatacept; Anakinra; Abalimumab; Etanercept; Infliximab; Remicade; Amevive; Natalizumab; Eculizumab; Antithymocyte globulin (rabbit); Thymoglobulin; Basiliximab; Daclizumab; Muromonab-CD3; OKT3; Omalizumab; Palivizumab; Enfuvirtide; Abciximab; Pegvisomant; Crotalidae polyvalent immune Fab (ovine); Digoxin immune serum Fab (ovine); Ranibizumab; Denileukin; Diftitox; Ibritumomab; Gemtuzumab; Ozogamicin; Tositumomab and I-tositumomab; Hepatitis B surface antigen (HBsAg); HPV vaccine; OspA; Anti-Rhesus (Rh) immunoglobulin G; Recombinant purified protein derivative (DPPD); Glucagon; Growth hormone releasing hormone (GHRH); Secretin; Thyroid stimulating hormone (TSH); thyrotropin; Capromab pendetide; Indium-111-octreotide; Satumomab pendetide; Arcitumomab; Nofetumomab; Apcitide; Imciromab pentetate; Technetium fanolesomab; HIV antigens; Enzyme immunoassay; Hepatitis C antigens; or Recombinant immunoblot assay (RI BA);
or
wherein the biological molecule is lysozyme, adlimumab, ubiquitin or Factor IX.

9. The composition of claim 7, wherein the composition is freeze dried, lyophilized, a solution, a liquid, a solid or a suspension.

10. A method of stabilizing a biological molecule comprising treating the biological molecule with an effective amount of the compound having the structure:

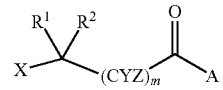

wherein
X is a hexosyl group selected from the group consisting of glucosyl, mannosyl, galactosyl, allosyl, altrosyl, gulosyl, idosyl and talosyl, or a uronic acid group selected from the group consisting of glucuronic acid, mannuronic acid, galacturonic acid, alluronic acid, altruronic acid, guluronic acid, iduronic acid and taluronic acid, or an uronic acid amide group selected from the group consisting of glucuronamide, mannuronamide, galacturonamide, alluronamide, altruronamide, guluronamide, iduronamide and taluronamide;
$R^1$ is H, halogen, OH, O-alkyl, $CONH_2$, $CO_2H$, $CO_2$-alkyl, or optionally substituted alkyl;
$R^2$ is H, halogen, OH, O-alkyl, $CONH_2$, $CO_2H$, or $CO_2$-alkyl;
each of Y and Z is independently H, OH, O-alkyl or optionally substituted alkyl;
m is 0, 1 or 2; and
A=$NR^3R^4$ or $OR^5$,
wherein
each of $R^3$ and $R^4$ is independently H, OH, O-alkyl or optionally substituted alkyl;
$R^5$ is optionally substituted alkyl;
wherein when X is glucosyl, then $R^1$ is optionally substituted alkyl, when each of $R^1$ and $R^2$ is H and m is 0, then X is other than glucuronic acid,
and wherein when X is glucosyl or mannosyl, m=0, $R^1$ is -alkyl-OH and $R^2$ is —H, and A is $NH_2$, then the compound is a beta-anomer;

and wherein the alkyl group of any alkyl is $C_{1-12}$ alkyl or $C_3$-$C_8$ cycloalkyl and wherein the substitution of any optionally substituted alkyl is F, Cl, Br, I, methyl, ethyl, n-propyl, isopropyl, n-butyl, tert-butyl, trifluoromethyl, hydroxyl, methoxy, ethoxy, n-propoxy, iso-propoxy, phenoxy, benzyloxy, p-trifluoromethyl-benzyloxy, trifluoromethanesulfonyl, methanesulfonyl, p-toluenesulfonyl, nitro, nitrosyl, mercapto, methylsulfanyl, ethylsulfanyl and propylsulfanyl, cyano, amino, methylamino, dimethylamino, ethylamino, diethylamino, or carboxy, and wherein the biological molecule is a protein, nucleotide, polypeptide or antibody, so as to thereby stabilize the biological molecule.

11. The compound of claim 1,
wherein the optionally substituted alkyl is $C_{1-8}$ alkyl, $C_{1-12}$ hydroxyalkyl or $C_3$-$C_8$ cycloalkyl.

12. The compound of claim 11,
wherein the optionally substituted alkyl is $C_{1-4}$ alkyl or $C_{1-4}$ hydroxyalkyl.

13. The compound of claim 12 having the structure:

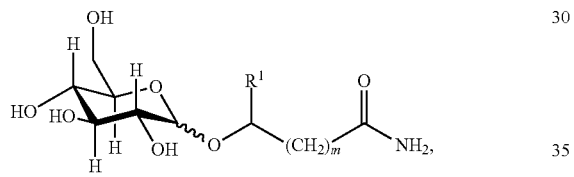

wherein $R^1$ is optionally substituted alkyl and m is 1 or 2;
wherein the optionally substituted alkyl is $C_1$-$C_4$ alkyl or $C_1$-$C_4$ hydroxyalkyl.

14. The compound of claim 12 having the structure:

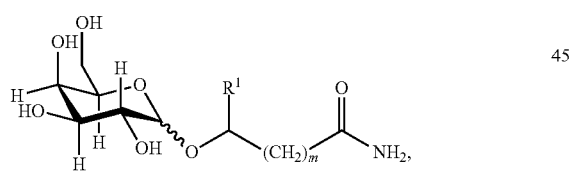

wherein $R^1$ is optionally substituted alkyl or $CONH_2$ and m is 0, 1 or 2;
wherein the optionally substituted alkyl is $C_1$-$C_4$ alkyl or $C_1$-$C_4$ hydroxyalkyl.

15. The compound of claim 12 having the structure:

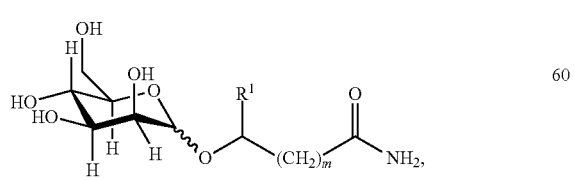

wherein $R^1$ is H, optionally substituted alkyl or $CONH_2$ and m is 1 or 2;

wherein the optionally substituted alkyl is $C_1$-$C_4$ alkyl or $C_1$-$C_4$ hydroxyalkyl.

16. A compound having the structure:

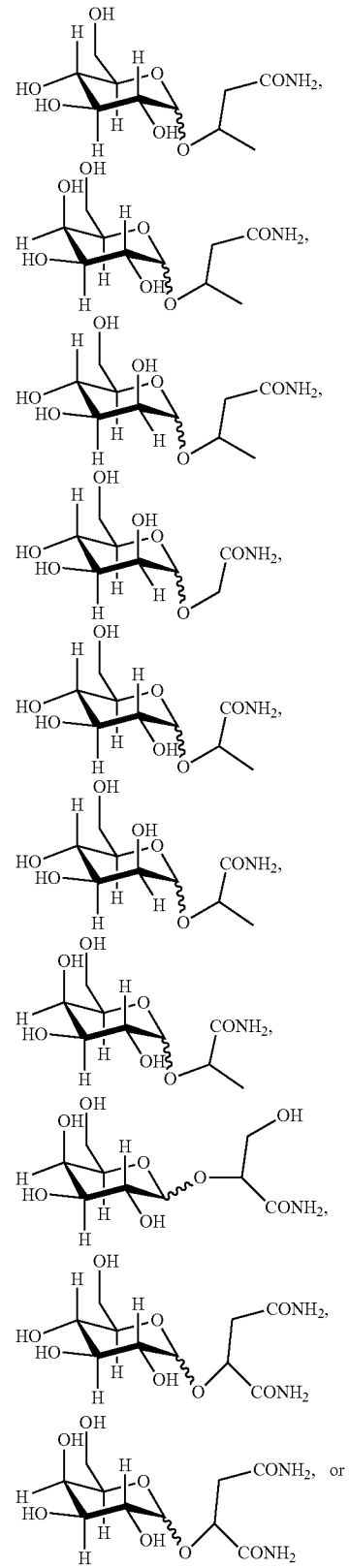

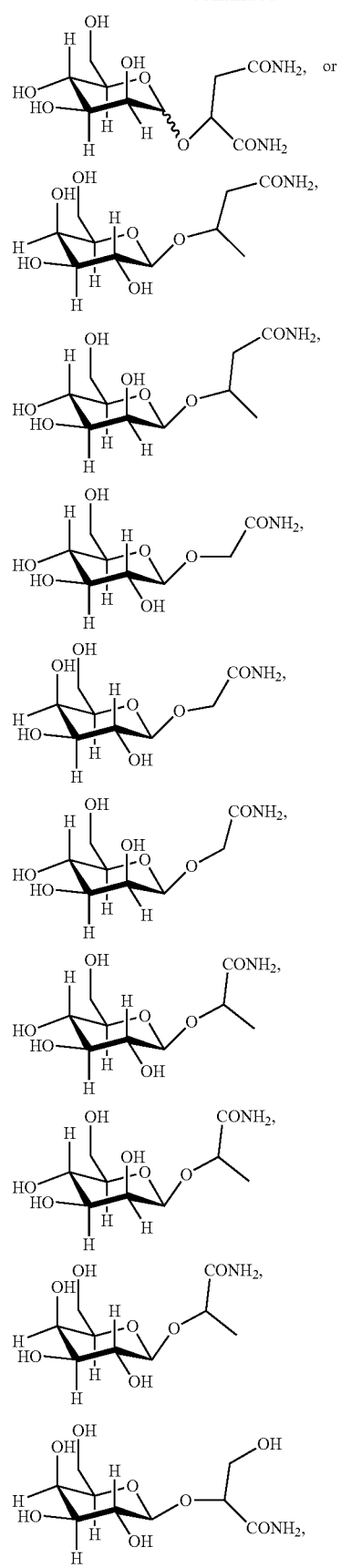
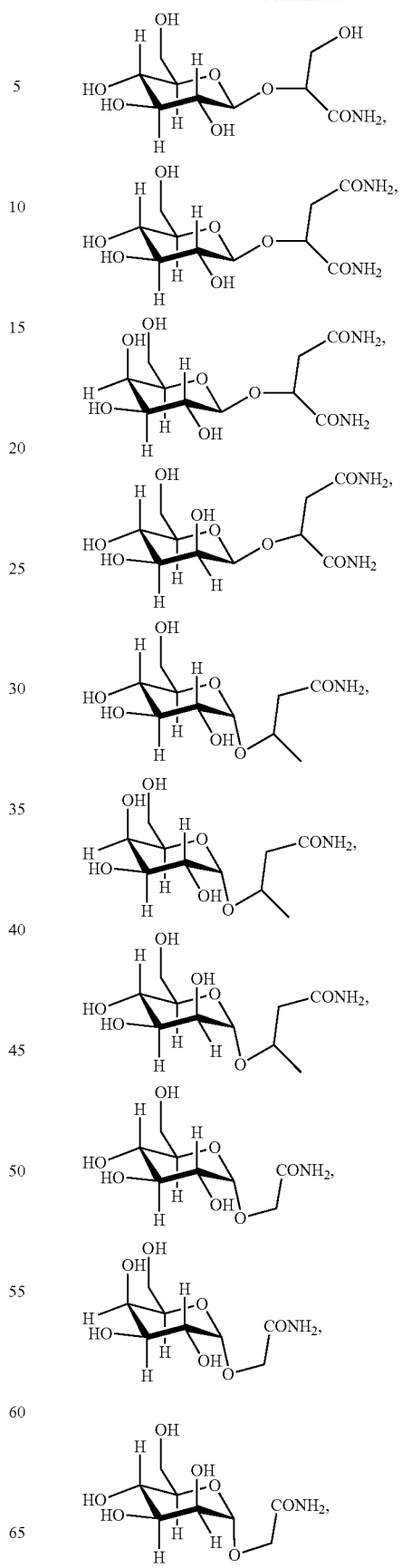

-continued

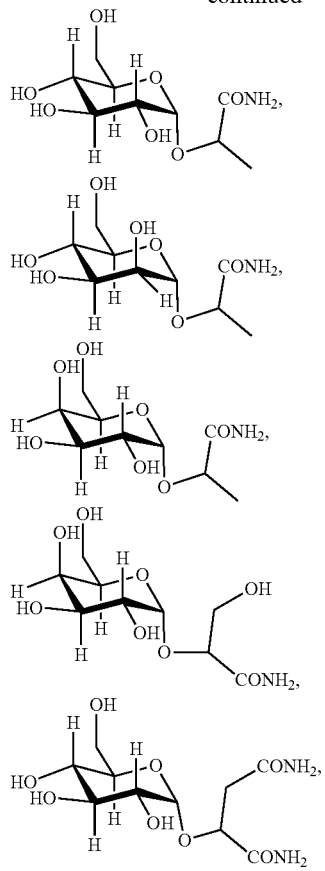

-continued

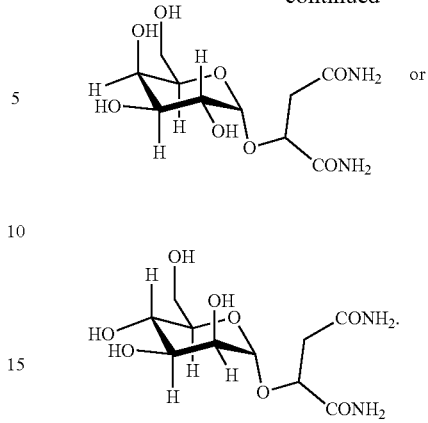

17. The compound of claim 1, wherein

X is glucosyl, wherein each of Y and Z is H, wherein $R^1$ is $CH_3$ and $R^2$ is H, and/or wherein each of $R^3$ and $R^4$ is H.

18. The compound of claim 1, wherein X is a hexosyl group selected from a group consisting of glucosyl and mannosyl; m is 0 or 1.

19. The compound of claim 1, wherein X is galactosyl; m is 0 or 1.

20. The compound of claim 1, wherein in (a) and/or (b), the alkyl is $C_{1-3}$ alkyl.

* * * * *